United States Patent
Koh et al.

(10) Patent No.: US 11,498,962 B2
(45) Date of Patent: Nov. 15, 2022

(54) ANTI-ANGIOPOIETIN-2 ANTIBODIES THAT INDUCE TIE2 ACTIVATION

(71) Applicants: INSTITUTE FOR BASIC SCIENCE, Daejeon (KR); KOREA ADVANCED INSTITUTE OF SCIENCE AND TECHNOLOGY, Daejeon (KR)

(72) Inventors: Gou Young Koh, Daejeon (KR); Jeomil Bae, Daejeon (KR); Mi Jeong Kim, Daejeon (KR); Jin-Sung Park, Daejeon (KR); Su Jin Seo, Daejeon (KR); Jaeryung Kim, Daejeon (KR); Jang Ryul Park, Daejeon (KR); Pilhan Kim, Daejeon (KR); Wangyuhl Oh, Daejeon (KR)

(73) Assignees: Institute for Basic Science, Daejeon (KR); Korea Advanced Institute of Science and Technology, Daejeon (KR)

( * ) Notice: Subject to any disclaimer, the term of this patent is extended or adjusted under 35 U.S.C. 154(b) by 14 days.

(21) Appl. No.: 16/995,707

(22) Filed: Aug. 17, 2020

(65) Prior Publication Data

US 2021/0079083 A1 Mar. 18, 2021

Related U.S. Application Data

(63) Continuation of application No. PCT/KR2019/001983, filed on Feb. 19, 2019.

(60) Provisional application No. 62/633,038, filed on Feb. 20, 2018.

(30) Foreign Application Priority Data

Feb. 18, 2019 (KR) .................. 10-2019-0018769

(51) Int. Cl.
*A61K 39/395* (2006.01)
*C07K 16/22* (2006.01)
*A61P 35/00* (2006.01)
*A61K 45/06* (2006.01)
*A61K 39/00* (2006.01)

(52) U.S. Cl.
CPC .......... *C07K 16/22* (2013.01); *A61K 39/3955* (2013.01); *A61K 45/06* (2013.01); *A61P 35/00* (2018.01); *A61K 2039/505* (2013.01); *C07K 2317/24* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,658,924 B2 | 2/2010 | Oliner et al. | |
| 8,987,420 B2 | 3/2015 | Thurston et al. | |
| 9,505,841 B2 | 11/2016 | Kim et al. | |
| 9,828,422 B2 | 11/2017 | Kim et al. | |
| 10,047,154 B2 | 8/2018 | Kim et al. | |
| 2010/0159587 A1 | 6/2010 | Brinkmann et al. | |
| 2013/0129722 A1 | 5/2013 | Lowy et al. | |
| 2013/0209492 A1 | 8/2013 | Thurston | |
| 2015/0125455 A1 | 5/2015 | Green et al. | |
| 2017/0247441 A1 | 8/2017 | Dengl et al. | |
| 2018/0273613 A1 | 9/2018 | Kim et al. | |

FOREIGN PATENT DOCUMENTS

| EP | 2832746 A1 | 2/2015 |
|---|---|---|
| KR | 1020150032075 A | 3/2015 |

OTHER PUBLICATIONS

Clark (Protein Engineering of Antibody Molecules for Prophylactic and Therapeutic Applications in Man, 1993, pp. 4-5).*
Hansbury, et al., "Production and characterization of a Tie2 agonist monoclonal antibody," Angiogenesis, 2001, 4(1):29-36.
Park et al., "Normalization of Tumor Vessels by TIE2 Activation and Ang2 Inhibition Enhances Drug Delivery and Produces a Favorable Tumor Microenvironment," Cancer Cell, 2016, 30(6):953-967.
Cho et al., "COMP-Ang1: A designed angiopoietin-1 variant with nonleaky angiogenic activity," PNAS, 2004, vol. 101, No. 15, pp. 5547-5552.
David S et al., "Effects of a synthetic PEG-ylated Tie-2 agonist peptide on endotoxemic lung injury and mortality," 2011, Am J Physiol Lung Cell Mol Physiol, 300: L851-L862.
Frye M, "Interfering with VE-PTP stabilizes endothelial junctions in vivo via Tie-2 in the absence of VE-cadherin," J. Exp. Med. 2015 vol. 212 No. 13 2267-2287.
Goel S et al., "Effects of Vascular-Endothelial Protein Tyrosine Phosphatase Inhibition on Breast Cancer Vasculature and Metastatic Progression," 2013, J Natl Cancer Inst, vol. 105, Issue 16, 1188-1201.

(Continued)

*Primary Examiner* — Christine J Saoud
(74) *Attorney, Agent, or Firm* — McNeill Baur PLLC

(57) ABSTRACT

The present invention relates to mouse antibodies that bind to angiopoietin-2 (Ang2), humanized anti-Ang2 antibodies derived therefrom, and the use thereof. The anti-Ang2 antibodies have a dual function of activating the Tie2 receptor together with neutralizing Ang2. The anti-Ang2 antibodies show the property of normalizing abnormal and pathological blood vessels, and thus exhibits therapeutic efficacy against various diseases and disorders associated with abnormal blood vessels. The present invention further provides an angiogenesis inhibitor and a composition for treatment of diseases associated with abnormal Ang2 expression and Tie2 dysregulation, which comprise the antibody as an active ingredient, and a composition for diagnosing diseases associated with Ang2 inhibition and Tie2 activation, which comprises the antibody.

12 Claims, 14 Drawing Sheets

Specification includes a Sequence Listing.

(56) References Cited

OTHER PUBLICATIONS

Marth C et al., "ENGOT-ov-6/TRINOVA-2: Randomised, double-blind, phase 3 study of pegylated liposomal doxorubicin plus trebananib or placebo in women with recurrent partially platinum-sensitive or resistant ovarian cancer," 2017, Eur. J. Cancer, 70:111-121.
Mellberg S et al., "Transcriptional profiling reveals a critical role for tyrosine phosphatase VE-PTP in regulation of VEGFR2 activity and endothelial cell morphogenesis," 2009, FASEB J., vol. 23, 1490-1502.
Saharinen P et al., "Therapeutic targeting of the angiopoietin-TIE pathway," 2017, Nature Review Drug Discovery, vol. 16, 636-661.
Extended European Search Report for EP 19757411.4, dated Jan. 19, 2022, 7 pages.
International Search Report for International Application No. PCT/KR2019/001983 dated May 27, 2019, 14 pages.
Hayashi M, et al., "VE-PTP regulates VEGFR2 activity in stalk cells to establish endothelial cell polarity and lumen formation," Nature Communication, 2013, 4:1-15.

\* cited by examiner

Crystal structure of Human Angiopoietin 2 RBD (PDB : 2GY7)

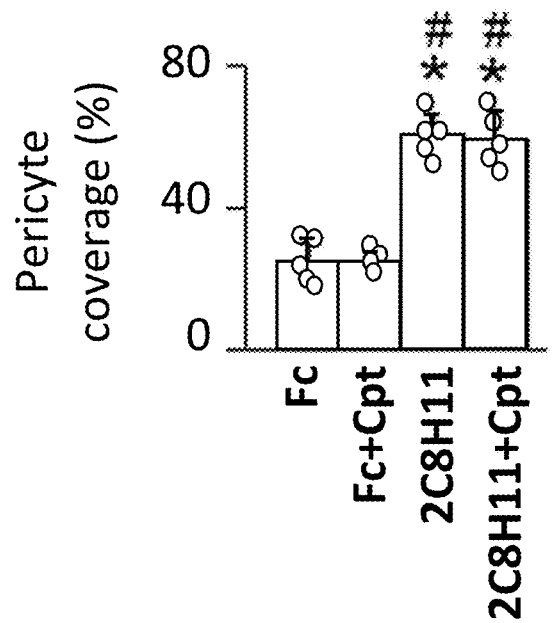
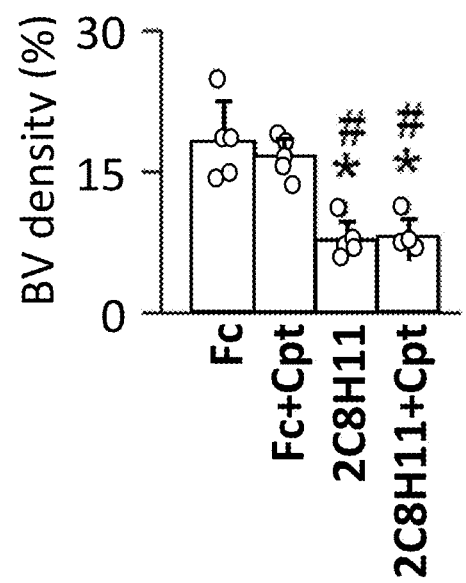
FIG. 10B
FIG. 10C
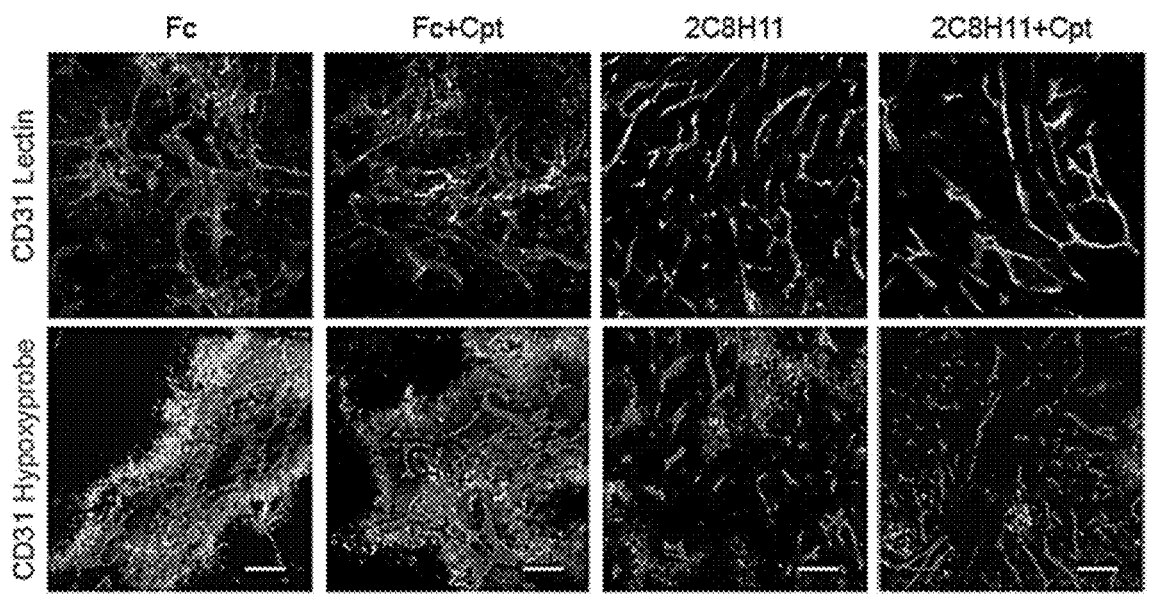
FIG. 11A

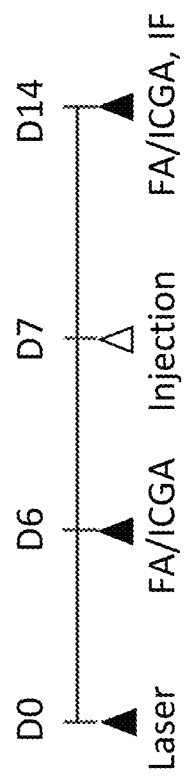
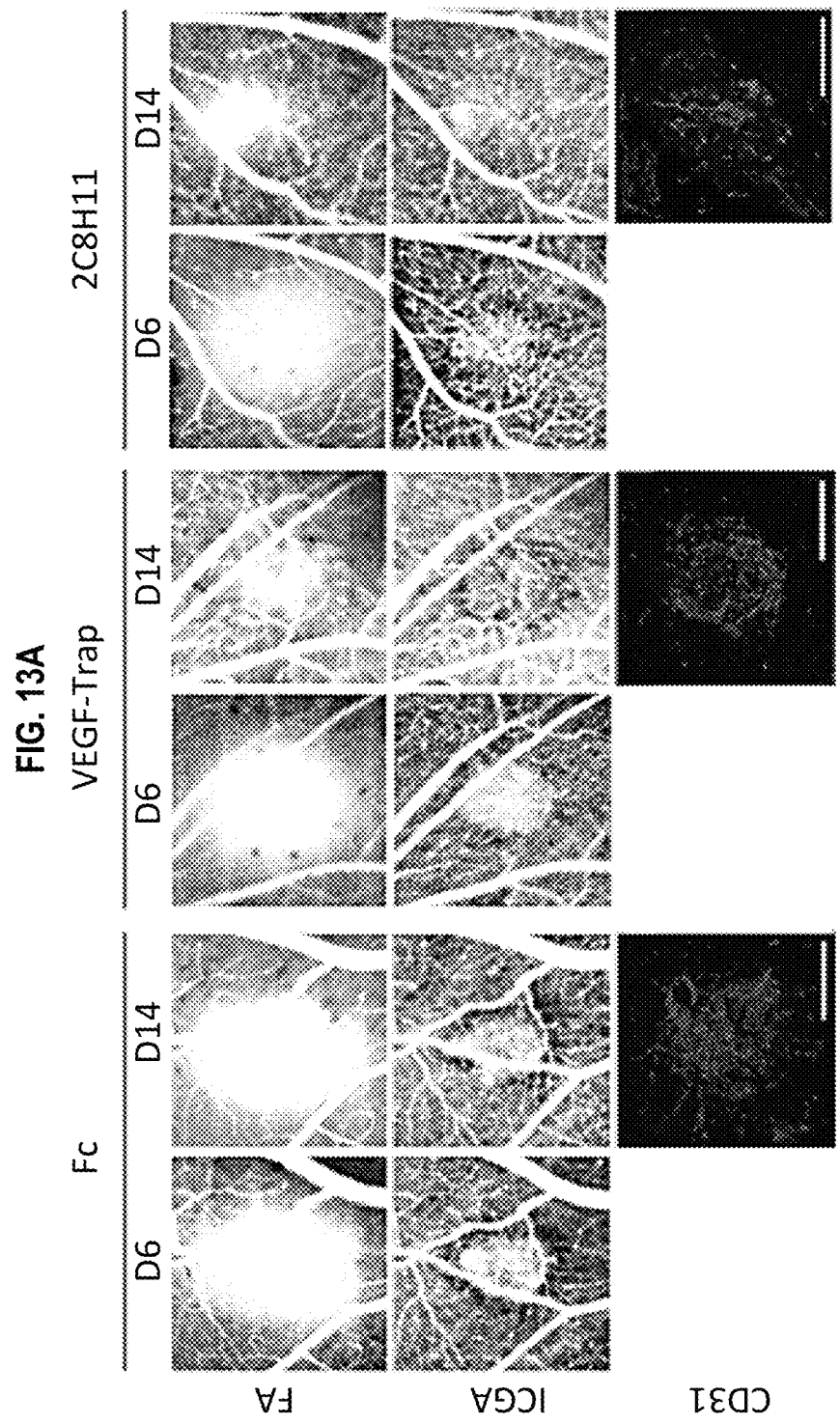
FIG. 13A
FIG. 13B

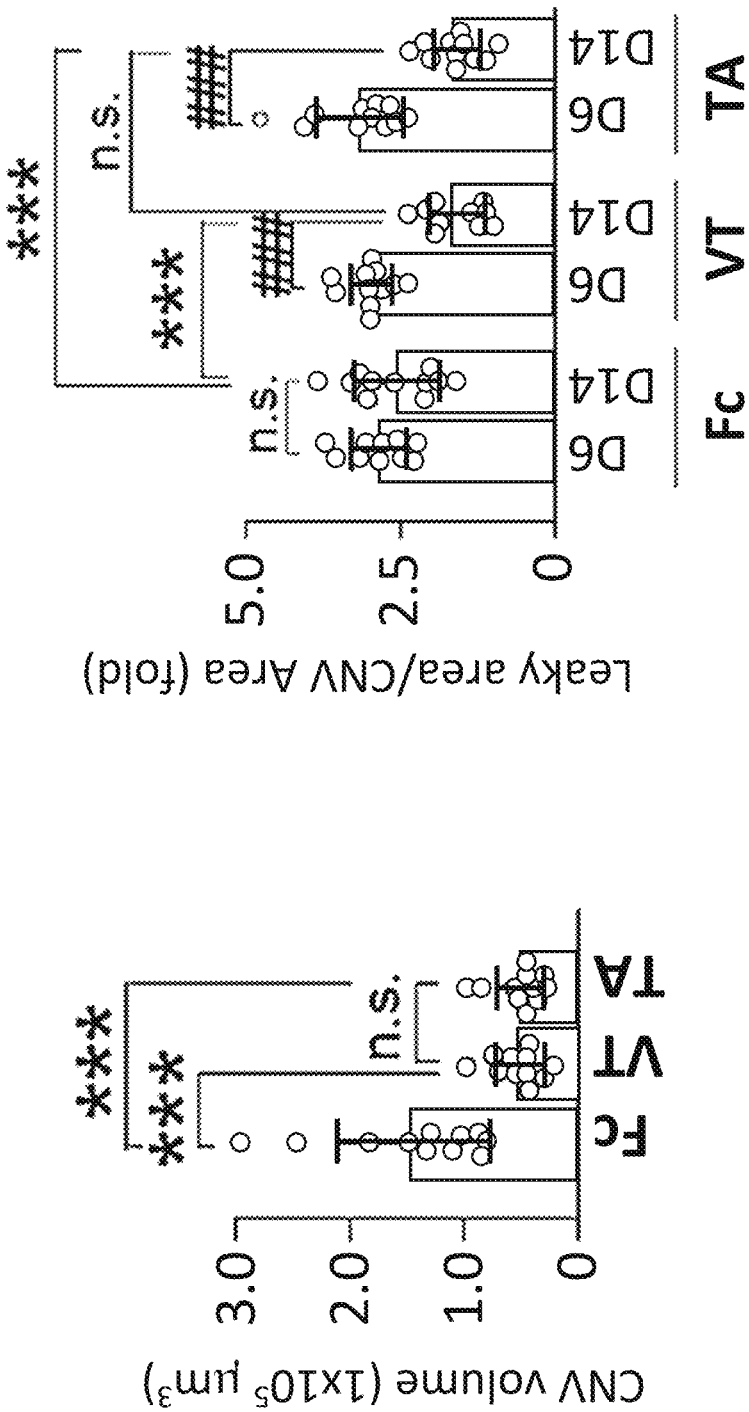
FIG. 13C
FIG. 13D
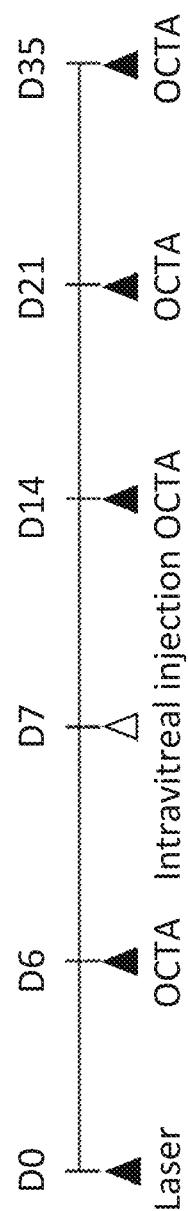
FIG. 14A

SEQUENCE LISTING

<160> NUMBER OF SEQ ID NOS: 117

<210> SEQ ID NO 1
<211> LENGTH: 496
<212> TYPE: PRT
<213> ORGANISM: Artificial Sequence
<220> FEATURE:
<223> OTHER INFORMATION: Human Angiopoietin-2 full-length

<400> SEQUENCE: 1

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
                20                  25                  30

Gln Tyr Gln Val Gln His Gly Ser Cys Ser Tyr Thr Phe Leu Leu Pro
            35                  40                  45

Glu Met Asp Asn Cys Arg Ser Ser Ser Pro Tyr Val Ser Asn Ala
        50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg

-continued

```
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 2
<211> LENGTH: 221
<212> TYPE: PRT
<213> ORGANISM: Artificial Sequence
<220> FEATURE:
<223> OTHER INFORMATION: Human Angiopoietin-2 receptor-binding
      domain(RBD)

<400> SEQUENCE: 2

Glu Glu Gln Ile Ser Phe Arg Asp Cys Ala Glu Val Phe Lys Ser Gly
1               5                   10                  15

His Thr Thr Asn Gly Ile Tyr Thr Leu Thr Phe Pro Asn Ser Thr Glu
            20                  25                  30

Glu Ile Lys Ala Tyr Cys Asp Met Glu Ala Gly Gly Gly Gly Trp Thr
        35                  40                  45

Ile Ile Gln Arg Arg Glu Asp Gly Ser Val Asp Phe Gln Arg Thr Trp
    50                  55                  60

Lys Glu Tyr Lys Val Gly Phe Gly Asn Pro Ser Gly Glu Tyr Trp Leu
65                  70                  75                  80

Gly Asn Glu Phe Val Ser Gln Leu Thr Asn Gln Gln Arg Tyr Val Leu
                85                  90                  95

Lys Ile His Leu Lys Asp Trp Glu Gly Asn Glu Ala Tyr Ser Leu Tyr
            100                 105                 110

Glu His Phe Tyr Leu Ser Ser Glu Glu Leu Asn Tyr Arg Ile His Leu
        115                 120                 125

Lys Gly Leu Thr Gly Thr Ala Gly Lys Ile Ser Ser Ile Ser Gln Pro
    130                 135                 140

Gly Asn Asp Phe Ser Thr Lys Asp Gly Asp Asn Asp Lys Cys Ile Cys
145                 150                 155                 160

Lys Cys Ser Gln Met Leu Thr Gly Gly Trp Trp Phe Asp Ala Cys Gly
                165                 170                 175

Pro Ser Asn Leu Asn Gly Met Tyr Tyr Pro Gln Arg Gln Asn Thr Asn
            180                 185                 190

Lys Phe Asn Gly Ile Lys Trp Tyr Tyr Trp Lys Gly Ser Gly Tyr Ser
        195                 200                 205

Leu Lys Ala Thr Thr Met Met Ile Arg Pro Ala Asp Phe
    210                 215                 220
```

-continued

```
<210> SEQ ID NO 3
<211> LENGTH: 5
<212> TYPE: PRT
<213> ORGANISM: Artificial Sequence
<220> FEATURE:
<223> OTHER INFORMATION: CDRH1

<400> SEQUENCE: 3

Asp Tyr Tyr Met Tyr
1               5

<210> SEQ ID NO 4
<211> LENGTH: 17
<212> TYPE: PRT
<213> ORGANISM: Artificial Sequence
<220> FEATURE:
<223> OTHER INFORMATION: CDRH2

<400> SEQUENCE: 4

Thr Ile Ser Val Gly Gly Ser Phe Thr Tyr Tyr Pro Asp Ser Val Lys
1               5                   10                  15

Gly

<210> SEQ ID NO 5
<211> LENGTH: 10
<212> TYPE: PRT
<213> ORGANISM: Artificial Sequence
<220> FEATURE:
<223> OTHER INFORMATION: CDRH3

<400> SEQUENCE: 5

Asp Trp Gly Leu Arg Pro Trp Phe Val Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: CDRL1

<400> SEQUENCE: 6

Lys Ala Ser Gln Asp Val Ser Thr Ala Val Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: CDRL2

<400> SEQUENCE: 7

Trp Ala Ser Thr Arg His Thr
1               5

<210> SEQ ID NO 8
<211> LENGTH: 9
<212> TYPE: PRT
<213> ORGANISM: Artificial Sequence
<220> FEATURE:
<223> OTHER INFORMATION: CDRL3

<400> SEQUENCE: 8

Gln Gln His Tyr Ser Thr Pro Pro Thr
1               5
```

```
<210> SEQ ID NO 9
<211> LENGTH: 119
<212> TYPE: PRT
<213> ORGANISM: Artificial Sequence
<220> FEATURE:
<223> OTHER INFORMATION: Heavy Chain Variable Region

<400> SEQUENCE: 9

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Val Gly Gly Ser Phe Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Asp Trp Gly Leu Arg Pro Trp Phe Val Tyr Trp Gly Gln Gly
            100                 105                 110

Thr Leu Val Thr Val Ser Ala
        115

<210> SEQ ID NO 10
<211> LENGTH: 357
<212> TYPE: DNA
<213> ORGANISM: Artificial Sequence
<220> FEATURE:
<223> OTHER INFORMATION: Heavy Chain Variable Region

<400> SEQUENCE: 10
gaagtgcagc tggtggagtc tgggggaggc ttagtgaagc ctggagggtc cctgaaactc      60
tcctgtgcag cctctggatt cactttcagt gactattaca tgtattgggt tcgccagact     120
ccggaaaaga ggctggagtg ggtcgcaacc attagtgttg gtggtagttt cacctactat     180
ccagacagtg tgaaggggcg attcaccatc tccagagaca atgccaagaa caacctgtac     240
ctgcaaatga gcagtctgaa gtctgaggac acagccatgt attactgtgc aagagactgg     300
ggattacgac cctggtttgt ttactggggc caagggactc tggtcactgt ctctgca       357

<210> SEQ ID NO 11
<211> LENGTH: 107
<212> TYPE: PRT
<213> ORGANISM: Artificial Sequence
<220> FEATURE:
<223> OTHER INFORMATION: Light Chain Variable Region

<400> SEQUENCE: 11

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60
```

```
Ser Gly Ser Gly Thr Asp Tyr Thr Leu Thr Ile Ser Ser Val Gln Ala
 65                  70                  75                  80

Glu Asp Leu Ala Leu Tyr Tyr Cys Gln Gln His Tyr Ser Thr Pro Pro
                 85                  90                  95

Thr Phe Gly Ser Gly Thr Lys Leu Glu Ile Lys
            100                 105

<210> SEQ ID NO 12
<211> LENGTH: 321
<212> TYPE: DNA
<213> ORGANISM: Artificial Sequence
<220> FEATURE:
<223> OTHER INFORMATION: Light Chain Variable Region

<400> SEQUENCE: 12
gacattgtga tgacccagtc tcacaaattc atgtccacat cagtaggaga cagggtcagc      60
atcacctgca aggccagtca ggatgtgagt actgctgtag cctggtatca acaaaaacca     120
gggcaatctc ctaaactact gatttactgg gcatccaccc ggcacactgg agtccctgat     180
cgcttcacag gcagtggatc tgggacagat tatactctca ccatcagcag tgtgcaggct     240
gaagacctgg cactttatta ctgtcagcaa cattatagca ctcctcccac gttcggctcg     300
gggacaaagt tggaaataaa a                                                321

<210> SEQ ID NO 13
<211> LENGTH: 5
<212> TYPE: PRT
<213> ORGANISM: Artificial Sequence
<220> FEATURE:
<223> OTHER INFORMATION: CDRH1

<400> SEQUENCE: 13

Ser Tyr Trp Met His
1               5

<210> SEQ ID NO 14
<211> LENGTH: 17
<212> TYPE: PRT
<213> ORGANISM: Artificial Sequence
<220> FEATURE:
<223> OTHER INFORMATION: CDRH2

<400> SEQUENCE: 14

Met Ile Asp Pro Ser Asp Ser Glu Thr Arg Leu Asn Gln Lys Phe Lys
1               5                   10                  15

Asp

<210> SEQ ID NO 15
<211> LENGTH: 12
<212> TYPE: PRT
<213> ORGANISM: Artificial Sequence
<220> FEATURE:
<223> OTHER INFORMATION: CDRH3

<400> SEQUENCE: 15

Arg Phe Tyr Tyr Gly Ser Asp Trp Tyr Phe Asp Val
1               5                   10

<210> SEQ ID NO 16
<211> LENGTH: 11
<212> TYPE: PRT
<213> ORGANISM: Artificial Sequence
<220> FEATURE:
<223> OTHER INFORMATION: CDRL1
```

<400> SEQUENCE: 16

Lys Ala Ser Gln Asp Val Gly Thr Ala Val Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: CDRL2

<400> SEQUENCE: 17

Trp Ala Ser Thr Arg His Thr
1               5

<210> SEQ ID NO 18
<211> LENGTH: 9
<212> TYPE: PRT
<213> ORGANISM: Artificial Sequence
<220> FEATURE:
<223> OTHER INFORMATION: CDRL3

<400> SEQUENCE: 18

Gln Gln Tyr Ser Ser Tyr Pro Leu Thr
1               5

<210> SEQ ID NO 19
<211> LENGTH: 121
<212> TYPE: PRT
<213> ORGANISM: Artificial Sequence
<220> FEATURE:
<223> OTHER INFORMATION: Heavy Chain Variable Region

<400> SEQUENCE: 19

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser Tyr
                20                  25                  30

Trp Met His Trp Val Lys Gln Arg Pro Gly Gln Gly Leu Glu Trp Ile
            35                  40                  45

Gly Met Ile Asp Pro Ser Asp Ser Glu Thr Arg Leu Asn Gln Lys Phe
        50                  55                  60

Lys Asp Lys Ala Ser Leu Thr Val Asp Lys Ser Ser Ser Thr Ala Tyr
65                  70                  75                  80

Met Gln Leu Ser Ser Pro Thr Ser Gly Asp Ser Ala Val Tyr Tyr Cys
                85                  90                  95

Ala Arg Arg Phe Tyr Tyr Gly Ser Asp Trp Tyr Phe Asp Val Trp Gly
                100                 105                 110

Ala Gly Ser Thr Val Thr Val Ser Ser
            115                 120

<210> SEQ ID NO 20
<211> LENGTH: 363
<212> TYPE: DNA
<213> ORGANISM: Artificial Sequence
<220> FEATURE:
<223> OTHER INFORMATION: Heavy Chain Variable Region

<400> SEQUENCE: 20
caggtgcaac tgcagcagtc tgggcctcag ctggttaggc ctggggcttc agtgaagata      60
tcctgcaagg cttctggtta ctcattcacc agctactgga tgcactgggt gaagcagagg     120

```
cctggacaag gtcttgagtg gattggcatg attgatcctt ccgatagtga aactaggtta    180
aatcagaagt tcaaggacaa ggcctcattg actgtagaca atcctccag cacagcctac     240 atgcaactca gcagcccgac atctggggac tctgcggtct attactgtgc aagacgtttt    300
tactacgggt cggactggta cttcgatgtc tggggcgcag gtccacggt caccgtctcc     360 tca                                                                  363
```

```
<210> SEQ ID NO 21
<211> LENGTH: 107
<212> TYPE: PRT
<213> ORGANISM: Artificial Sequence
<220> FEATURE:
<223> OTHER INFORMATION: Light Chain Variable Region

<400> SEQUENCE: 21
```

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ser Gly Thr Lys Leu Glu Ile Lys
            100                 105
```

```
<210> SEQ ID NO 22
<211> LENGTH: 321
<212> TYPE: DNA
<213> ORGANISM: Artificial Sequence
<220> FEATURE:
<223> OTHER INFORMATION: Light Chain Variable Region

<400> SEQUENCE: 22
```

```
gacattgtga tgacccagtc tcacaaattc atgtccacat cagtaggaga cagggtcagc    60
atcacctgca aggccagtca ggatgtgggt actgctgtag cctggtatca acagaaacca    120
ggtcaatctc ctaaactact gatttactgg gcatccaccc ggcacactgg agtccctgat    180
cgcttcacag gcagtggatc tgggacagat ttcactctca ccattagcaa tgtgcagtct    240
gaagacttgg cagattattt ctgtcagcaa tatagcagct atcctctcac gttcggctcg    300
gggacaaagt tggaaataaa a                                              321
```

```
<210> SEQ ID NO 23
<211> LENGTH: 5
<212> TYPE: PRT
<213> ORGANISM: Artificial Sequence
<220> FEATURE:
<223> OTHER INFORMATION: CDRH1

<400> SEQUENCE: 23
```

```
Asp Tyr Tyr Met Tyr
1               5
```

```
<210> SEQ ID NO 24
```

```
<211> LENGTH: 17
<212> TYPE: PRT
<213> ORGANISM: Artificial Sequence
<220> FEATURE:
<223> OTHER INFORMATION: CDRH2

<400> SEQUENCE: 24

Thr Ile Asn Asp Gly Gly Ser Tyr Thr Tyr Tyr Pro Asp Ser Val Lys
1               5                   10                  15
Gly

<210> SEQ ID NO 25
<211> LENGTH: 10
<212> TYPE: PRT
<213> ORGANISM: Artificial Sequence
<220> FEATURE:
<223> OTHER INFORMATION: CDRH3

<400> SEQUENCE: 25

Asp Trp Gly Leu Arg Pro Trp Phe Val Tyr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: CDRL1

<400> SEQUENCE: 26

Lys Ala Ser Gln Asp Val Ser Thr Ala Val Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: CDRL2

<400> SEQUENCE: 27

Trp Ala Ser Thr Arg His Thr
1               5

<210> SEQ ID NO 28
<211> LENGTH: 9
<212> TYPE: PRT
<213> ORGANISM: Artificial Sequence
<220> FEATURE:
<223> OTHER INFORMATION: CDRL3

<400> SEQUENCE: 28

Gln Gln His Tyr Thr Thr Pro Pro Thr
1               5

<210> SEQ ID NO 29
<211> LENGTH: 119
<212> TYPE: PRT
<213> ORGANISM: Artificial Sequence
<220> FEATURE:
<223> OTHER INFORMATION: Heavy Chain Variable Region

<400> SEQUENCE: 29

Gln Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
```

```
                    20                  25                  30
Tyr Met Tyr Trp Ile Arg Gln Thr Pro Glu Lys Arg Leu Glu Trp Val
            35                  40                  45

Ala Thr Ile Asn Asp Gly Gly Ser Tyr Thr Tyr Tyr Pro Asp Ser Val
        50                  55                  60

Lys Gly Arg Phe Thr Ile Ser Arg Asp Asn Ala Lys Asn Asn Leu Tyr
 65                 70                  75                  80

Leu Gln Met Ser Ser Leu Lys Ser Glu Asp Thr Ala Met Tyr Tyr Cys
                85                  90                  95

Ala Arg Asp Trp Gly Leu Arg Pro Trp Phe Val Tyr Trp Gly Gln Gly
            100                 105                 110

Thr Leu Val Thr Val Ser Ala
        115
```

<210> SEQ ID NO 30
<211> LENGTH: 357
<212> TYPE: DNA
<213> ORGANISM: Artificial Sequence
<220> FEATURE:
<223> OTHER INFORMATION: Heavy Chain Variable Region

<400> SEQUENCE: 30

```
gaagtgcagc tggtggagtc tgggggaggc ttagtgaagc ctggagggtc cctgaaactc      60
tcctgtgcag cctctggatt cactttcagt gactattaca tgtattggat cgccagact     120 ccggaaaaga ggctggagtg ggtcgcaacc attaatgatg gtggtagtta cacctactat    180
ccagacagtg tgaaggggcg attcaccatc tccagagaca tgccaagaa caacctgtac     240 ctgcaaatga gcagtctgaa gtctgaggac acagccatgt attactgtgc aagagactgg    300
ggattacgac cctggtttgt ttactggggc caagggactc tggtcactgt ctctgca       357
```

<210> SEQ ID NO 31
<211> LENGTH: 107
<212> TYPE: PRT
<213> ORGANISM: Artificial Sequence
<220> FEATURE:
<223> OTHER INFORMATION: Light Chain Variable Region

<400> SEQUENCE: 31

```
Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
 65                 70                  75                  80

Glu Asp Leu Ala Leu Tyr Tyr Cys Gln Gln His Tyr Thr Thr Pro Pro
                85                  90                  95

Thr Phe Gly Ser Gly Thr Lys Leu Glu Ile Lys
            100                 105
```

<210> SEQ ID NO 32
<211> LENGTH: 321
<212> TYPE: DNA
<213> ORGANISM: Artificial Sequence
<220> FEATURE:

<223> OTHER INFORMATION: Light Chain Variable Region

<400> SEQUENCE: 32

```
gacattgtga tgacccagtc tcacaaattc atgtccacat cagtaggaga cagggtcagc    60
atcacctgca aggccagtca ggatgtgagt actgctgtag cctggtatca acaaaaacca   120
gggcaatctc ctaaactact gatttactgg gcatccaccc ggcacactgg agtccctgat   180
cgcttcacag gcagtggatc tgggacagat tatactctca ccatcagcag tgtgcaggct   240
gaagacctgg cactttatta ctgtcagcaa cattatacca ctcctcccac gttcggctcg   300
gggacaaagt tggaaataaa a                                             321
```

<210> SEQ ID NO 33
<211> LENGTH: 5
<212> TYPE: PRT
<213> ORGANISM: Artificial Sequence
<220> FEATURE:
<223> OTHER INFORMATION: CDRH1

<400> SEQUENCE: 33

Gly Tyr Asn Met Asn
1               5

<210> SEQ ID NO 34
<211> LENGTH: 17
<212> TYPE: PRT
<213> ORGANISM: Artificial Sequence
<220> FEATURE:
<223> OTHER INFORMATION: CDRH2

<400> SEQUENCE: 34

Asn Ile Asp Pro Tyr Tyr Gly Gly Thr Ser Tyr Asn Gln Lys Phe Lys
1               5                   10                  15
Gly

<210> SEQ ID NO 35
<211> LENGTH: 7
<212> TYPE: PRT
<213> ORGANISM: Artificial Sequence
<220> FEATURE:
<223> OTHER INFORMATION: CDRH3

<400> SEQUENCE: 35

Tyr Gly Asn Tyr Val Asp Tyr
1               5

<210> SEQ ID NO 36
<211> LENGTH: 11
<212> TYPE: PRT
<213> ORGANISM: Artificial Sequence
<220> FEATURE:
<223> OTHER INFORMATION: CDRL1

<400> SEQUENCE: 36

Lys Ala Ser Gln Asp Val Ser Thr Ala Val Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: CDRL2

<400> SEQUENCE: 37

```
Trp Ala Ser Thr Arg His Thr
1               5

<210> SEQ ID NO 38
<211> LENGTH: 9
<212> TYPE: PRT
<213> ORGANISM: Artificial Sequence
<220> FEATURE:
<223> OTHER INFORMATION: CDRL3

<400> SEQUENCE: 38

Gln Gln His Tyr Asn Thr Pro Pro Thr
1               5

<210> SEQ ID NO 39
<211> LENGTH: 116
<212> TYPE: PRT
<213> ORGANISM: Artificial Sequence
<220> FEATURE:
<223> OTHER INFORMATION: Heavy Chain Variable Region

<400> SEQUENCE: 39

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Val Arg Tyr Gly Asn Tyr Val Asp Tyr Trp Gly Gln Gly Thr Thr Leu
            100                 105                 110

Thr Val Ser Ser
        115

<210> SEQ ID NO 40
<211> LENGTH: 342
<212> TYPE: DNA
<213> ORGANISM: Artificial Sequence
<220> FEATURE:
<223> OTHER INFORMATION: Heavy Chain Variable Region

<400> SEQUENCE: 40
cagctgcagc agtctggacc tgagctggag aagcctggcg cttcagtgaa gatatcctgc      60
aaggcttctg gttactcatt cactggctac aacatgaact gggtgaagca gagcaatgga     120
aagagccttg agtggattgg aaatattgat ccttactatg gtggtactag ctacaaccag     180
aagttcaagg gcaaggccac attgactgta gacaaatcct ccagcacagc ctacatgcag     240
ctcaagagcc tgacatctga ggactctgca gtctattact gtgtaaggta tggtaactac     300
gtggactact ggggccaagg caccactctc acagtctcct ca                        342

<210> SEQ ID NO 41
<211> LENGTH: 107
<212> TYPE: PRT
<213> ORGANISM: Artificial Sequence
<220> FEATURE:
```

<223> OTHER INFORMATION: Light Chain Variable Region

<400> SEQUENCE: 41

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Asn Thr Pro Pro
                85                  90                  95

Thr Phe Gly Ser Gly Thr Lys Leu Glu Ile Lys
            100                 105

<210> SEQ ID NO 42
<211> LENGTH: 321
<212> TYPE: DNA
<213> ORGANISM: Artificial Sequence
<220> FEATURE:
<223> OTHER INFORMATION: Light Chain Variable Region

<400> SEQUENCE: 42
gacattgtga tgacccagtc ccacaaattc atgtccacat cagtaggaga cagggtcagc      60
atcacctgca aggccagtca ggatgtgagt actgctgtag cctggtatca acaaaaacca     120
gggcaatctc ctaaactact gatttactgg gcatccaccc ggcacactgg agtccctgat     180
cgcttcacag gcagtggatc tgggacagat tatactctca ccatcagcag tgtgcaggct     240
gaagacctgg cactttatta ctgtcagcaa cattataaca ctcctcccac gttcggctcg     300
gggacaaagt tggaaataaa a                                               321

<210> SEQ ID NO 43
<211> LENGTH: 119
<212> TYPE: PRT
<213> ORGANISM: Artificial Sequence
<220> FEATURE:
<223> OTHER INFORMATION: VH

<400> SEQUENCE: 43

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Ile Arg Gln Ala Pro Gly Lys Gly Leu Glu Trp Val
        35                  40                  45

Ser Thr Ile Ser Val Gly Gly Ser Phe Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Gly Leu Arg Pro Trp Phe Val Tyr Trp Gly Gln Gly
            100                 105                 110

Thr Leu Val Thr Val Ser Ser

<210> SEQ ID NO 44
<211> LENGTH: 107
<212> TYPE: PRT
<213> ORGANISM: Artificial Sequence
<220> FEATURE:
<223> OTHER INFORMATION: VL

<400> SEQUENCE: 44

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Trp Ala Ser Thr Arg His Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Ser Thr Pro Pro
                85                  90                  95
Thr Phe Gly Gln Gly Thr Lys Val Glu Ile Lys
            100                 105

<210> SEQ ID NO 45
<211> LENGTH: 357
<212> TYPE: DNA
<213> ORGANISM: Artificial Sequence
<220> FEATURE:
<223> OTHER INFORMATION: VH

<400> SEQUENCE: 45
caggtacagc tcgtggagtc tggtggaggc ttggtgaaac ctggagggtc cctgagactt      60
agctgtgcag cttccggctt cacattttca gactattata tgtattggat cagacaggct     120
cccgggaagg gcttggagtg ggtttcaacc attagtgttg gcggatcttt tacttactac     180
ccagacagtg tgaagggag attcacaatc tccaggata acgcgaaaaa cagcctgtat      240
ctccaaatga atagcctgag agccgaagat accgccgtgt actactgcgc cagagactgg     300
ggattacggc ctggttcgt gtactggggc cagggaaccc tggtcaccgt ctcctca         357

<210> SEQ ID NO 46
<211> LENGTH: 321
<212> TYPE: DNA
<213> ORGANISM: Artificial Sequence
<220> FEATURE:
<223> OTHER INFORMATION: VL

<400> SEQUENCE: 46
gacatccaga tgacacagtc cccaagctcc ctgtctgcat ctgtgggaga ccgggtgacc      60
atcacttgta aggcctcaca ggatgttct actgctgtcg catggtacca gcaaaagccg     120
ggtaaagctc ccaagctttt gatatactgg gccagcacca ggcacacagg cgtgccatca     180
agattcagtg gtccggatc cggcacggat tttacactca ctattagctc actgcaacct      240
gaagactttg ccacctatta ctgccagcag cattatagca cccctcccac cttcggtcag     300
ggcactaaag tagaaatcaa a                                                321

<210> SEQ ID NO 47

```
<211> LENGTH: 119
<212> TYPE: PRT
<213> ORGANISM: Artificial Sequence
<220> FEATURE:
<223> OTHER INFORMATION: VH

<400> SEQUENCE: 47

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ser Thr Ile Ser Val Gly Gly Ser Phe Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Gly Leu Arg Pro Trp Phe Val Tyr Trp Gly Gln Gly
            100                 105                 110

Thr Leu Val Thr Val Ser Ser
        115

<210> SEQ ID NO 48
<211> LENGTH: 107
<212> TYPE: PRT
<213> ORGANISM: Artificial Sequence
<220> FEATURE:
<223> OTHER INFORMATION: VL

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Pro
                85                  90                  95

Thr Phe Gly Gln Gly Thr Lys Val Glu Ile Lys
            100                 105

<210> SEQ ID NO 49
<211> LENGTH: 357
<212> TYPE: DNA
<213> ORGANISM: Artificial Sequence
<220> FEATURE:
<223> OTHER INFORMATION: VH

<400> SEQUENCE: 49
caggtccagc tggtggaatc cggcggaggc ttggtgaagc ctggaggcag cctaagactc    60
tcctgtgcag cctctggctt caccttctct gactattaca tgtattgggt ccgccaggct   120
ccagggaaag ggctcgagtg ggtttcaaca attagtgtag gtggaagctt cacctactat   180
```

```
cctgactccg tgaaaggaag atttacgatc tctagggata atgccaagaa ctcactgtac    240
cttcagatga acagcctgag agcggaggac acagccgtgt actactgcgc tagagattgg    300
ggattaagac cctggtttgt ttattggggc agggaaccc tggtcaccgt ctcctca       357
```

```
<210> SEQ ID NO 50
<211> LENGTH: 321
<212> TYPE: DNA
<213> ORGANISM: Artificial Sequence
<220> FEATURE:
<223> OTHER INFORMATION: VL

<400> SEQUENCE: 50
gacatccaga tgacacagtc cccaagctcc ctgtctgcat ctgtgggaga ccgggtgacc     60
atcacttgta aggcctcaca ggatgtttct actgctgtcg catggtacca gcaaaagccg    120
ggtaaagctc ccaagctttt gatatactgg gccagcacca gcacacagg cgtgccatca    180 agattcagtg gtccggatc cggcacggat tttacactca ctattagctc actgcaacct    240
gaagactttg ccacctatta ctgccagcag cattatagca ccctcccac cttcggtcag    300 ggcactaaag tagaaatcaa a                                               321
```

```
<210> SEQ ID NO 51
<211> LENGTH: 119
<212> TYPE: PRT
<213> ORGANISM: Artificial Sequence
<220> FEATURE:
<223> OTHER INFORMATION: VH

<400> SEQUENCE: 51

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Thr Ile Ser Val Gly Gly Ser Phe Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Gly Leu Arg Pro Trp Phe Val Tyr Trp Gly Gln Gly
            100                 105                 110

Thr Leu Val Thr Val Ser Ser
        115
```

```
<210> SEQ ID NO 52
<211> LENGTH: 107
<212> TYPE: PRT
<213> ORGANISM: Artificial Sequence
<220> FEATURE:
<223> OTHER INFORMATION: VL

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
```

```
                 35                  40                  45
Tyr Trp Ala Ser Thr Arg His Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Ser Thr Pro Pro
                 85                  90                  95

Thr Phe Gly Gln Gly Thr Lys Val Glu Ile Lys
            100                 105
```

<210> SEQ ID NO 53
<211> LENGTH: 357
<212> TYPE: DNA
<213> ORGANISM: Artificial Sequence
<220> FEATURE:
<223> OTHER INFORMATION: VH

<400> SEQUENCE: 53

| | | | | | |
|---|---|---|---|---|---|
| caggtgcagc | tggtcgaatc | tggaggaggc | ttggtgaaac | ctggggggtc | cctgagactc | 60 |
| tcttgtgcag | cctccggctt | taccttttct | gactactaca | tgtattgggt | tcgccaggct | 120 |
| cccgtaagg | ggttagagtg | ggtggctacc | attagtgttg | gcggttcatt | tacttattac | 180 |
| ccagatagtg | tgaaaggacg | gttcaccatc | agcagggaca | tgcaaagaa | ctcactctat | 240 |
| ctacaaatga | atagcctgag | agccgaggat | acagcgtgt | attactgcgc | cagagattgg | 300 |
| ggacttcgac | catggttcgt | ctactggggc | cagggaaccc | tggtcaccgt | ctcctca | 357 |

<210> SEQ ID NO 54
<211> LENGTH: 321
<212> TYPE: DNA
<213> ORGANISM: Artificial Sequence
<220> FEATURE:
<223> OTHER INFORMATION: VL

<400> SEQUENCE: 54

| | | | | | |
|---|---|---|---|---|---|
| gacatccaga | tgacacagtc | cccaagctcc | ctgtctgcat | ctgtgggaga | ccgggtgacc | 60 |
| atcacttgta | aggcctcaca | ggatgtttct | actgctgtcg | catggtacca | gcaaaagccg | 120 |
| ggtaaagctc | ccaagctttt | gatatactgg | gccagcacca | ggcacacagg | cgtgccatca | 180 |
| agattcagtg | gtccggatc | cggcacggat | tttacactca | ctattagctc | actgcaacct | 240 |
| gaagactttg | ccacctatta | ctgccagcag | cattatagca | cccctcccac | cttcggtcag | 300 |
| ggcactaaag | tagaaatcaa | a | | | | 321 |

<210> SEQ ID NO 55
<211> LENGTH: 121
<212> TYPE: PRT
<213> ORGANISM: Artificial Sequence
<220> FEATURE:
<223> OTHER INFORMATION: VH

<400> SEQUENCE: 55

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Trp Met His Trp Val Arg Gln Ala Pro Gly Gln Gly Leu Glu Trp Met
             35                  40                  45

Gly Met Ile Asp Pro Ser Asp Ser Glu Thr Arg Leu Asn Gln Lys Phe
         50                  55                  60
```

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
        115                 120

<210> SEQ ID NO 56
<211> LENGTH: 107
<212> TYPE: PRT
<213> ORGANISM: Artificial Sequence
<220> FEATURE:
<223> OTHER INFORMATION: VL

<400> SEQUENCE: 56

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys
            100                 105

<210> SEQ ID NO 57
<211> LENGTH: 363
<212> TYPE: DNA
<213> ORGANISM: Artificial Sequence
<220> FEATURE:
<223> OTHER INFORMATION: VH

<400> SEQUENCE: 57
caggtgcagc tggtgcagag tggagctgag gtaaaaaagc ccggcgccag tgtgaaggtt      60
agttgcaagg cctctggata caccttcaca agctattgga tgcactgggt gcgacaagct     120
cctgggcagg ggcttgagtg gatgggaatg atcgacccat ccgattcaga aactaggctc     180
aaccagaaat tcaagatag agtgactatg accagggaca cctccacgag cacagtctac      240
atggaattgt caagcctgcg ctctgaggac acagccgtgt actattgtgc aagacggttt     300
tactatggta gcgattggta ctttgatgtt tggggccagg aaccctggt caccgtctcc      360 tca                                                                    363

<210> SEQ ID NO 58
<211> LENGTH: 321
<212> TYPE: DNA
<213> ORGANISM: Artificial Sequence
<220> FEATURE:
<223> OTHER INFORMATION: VL

<400> SEQUENCE: 58
gacatacagt tgacccagtc tccttccttc ctgtccgcct ccgtgggcga tagagttacc      60

-continued

```
attacttgca aagctagtca ggacgtgggt accgcagtgg cctggtatca gcagaaacca    120
ggtaaagccc ctaagctcct gatctactgg gcatcaacac ggcacacagg ggtcccaagc    180
aggttttctg gcagcggatc aggaaccgaa tttacactga cgatctcgtc tctgcagccc    240
gaggatttcg ctacttacta ctgtcaacaa tatagtagct atccccctca tttcggtcag    300
ggcactaaag tagaaatcaa a                                              321
```

<210> SEQ ID NO 59
<211> LENGTH: 121
<212> TYPE: PRT
<213> ORGANISM: Artificial Sequence
<220> FEATURE:
<223> OTHER INFORMATION: VH

<400> SEQUENCE: 59

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Arg Gln Ala Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
        115                 120
```

<210> SEQ ID NO 60
<211> LENGTH: 107
<212> TYPE: PRT
<213> ORGANISM: Artificial Sequence
<220> FEATURE:
<223> OTHER INFORMATION: VL

<400> SEQUENCE: 60

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys
            100                 105
```

<210> SEQ ID NO 61
<211> LENGTH: 363

```
<212> TYPE: DNA
<213> ORGANISM: Artificial Sequence
<220> FEATURE:
<223> OTHER INFORMATION: VH

<400> SEQUENCE: 61
caggtgcaac tcgtgcagtc tggagctgaa gtgaagaaac ccggggcctc agtgaaggtg      60
agttgcaaag catctgggta ctcatttacc agctattgga tgcactgggt gcggcaggcc     120
ccaggacaag gcctggagtg gattggcatg atcgacccct ccgatagtga aacgaggctg     180
aaccagaagt ttaaagatcg cgtcaccatg accagggaca aagtacttc tacagtctac      240 atggagttga gcagcctgag atcagaggac acagccgttt actactgtgc tagacgattc     300
tattatggca gcgactggta tttcgatgta tggggccagg aaccctggt caccgtctcc      360 tca                                                                   363

<210> SEQ ID NO 62
<211> LENGTH: 321
<212> TYPE: DNA
<213> ORGANISM: Artificial Sequence
<220> FEATURE:
<223> OTHER INFORMATION: VL

<400> SEQUENCE: 62
gacatacagt tgacccagtc tccttccttc ctgtccgcct ccgtgggcga tagagttacc      60
attacttgca aagctagtca ggacgtgggt accgcagtgg cctggtatca gcagaaacca     120
ggtaaagccc ctaagctcct gatctactgg gcatcaacac ggcacacagg ggtcccaagc     180
aggttttctg gcagcggatc aggaaccgaa tttacactga cgatctcgtc tctgcagccc     240
gaggatttcg ctacttacta ctgtcaacaa tatagtagct atccctcac tttcggtcag      300 ggcactaaag tagaaatcaa a                                               321

<210> SEQ ID NO 63
<211> LENGTH: 121
<212> TYPE: PRT
<213> ORGANISM: Artificial Sequence
<220> FEATURE:
<223> OTHER INFORMATION: VH

<400> SEQUENCE: 63

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Ser Phe Thr Ser Tyr
            20                  25                  30

Trp Met His Trp Val Arg Gln Ala Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Lys Ala Ser Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
        115                 120

<210> SEQ ID NO 64
```

<211> LENGTH: 107
<212> TYPE: PRT
<213> ORGANISM: Artificial Sequence
<220> FEATURE:
<223> OTHER INFORMATION: VL

<400> SEQUENCE: 64

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys
            100                 105
```

<210> SEQ ID NO 65
<211> LENGTH: 363
<212> TYPE: DNA
<213> ORGANISM: Artificial Sequence
<220> FEATURE:
<223> OTHER INFORMATION: VH

<400> SEQUENCE: 65

| caggtgcaac tggtgcagtc tggtgctgag gtgaagaaac caggcgcttc agtcaaggta | 60 |
| agctgcaaag caagtggata tccttcacc tcttattgga tgcactgggt tagacaggcc | 120 |
| cctggtcaag cctcgagtg gattggcatg atcgacccct ctgacagcga aactaggctg | 180 |
| aatcagaaat taaggacaa ggcctccatg acacgggata catccacaag caccgtttac | 240 |
| atggaactga gctcgctgag aagtgaggac actgccgtgt attactgtgc gagacgcttt | 300 |
| tattacgggt cagattggta cttcgatgtg tggggccagg gaaccctggt caccgtctcc | 360 |
| tca | 363 |

<210> SEQ ID NO 66
<211> LENGTH: 321
<212> TYPE: DNA
<213> ORGANISM: Artificial Sequence
<220> FEATURE:
<223> OTHER INFORMATION: VL

<400> SEQUENCE: 66

| gacatacagt tgacccagtc tccttccttc ctgtccgcct ccgtgggcga tagagttacc | 60 |
| attacttgca aagctagtca ggacgtgggt accgcagtgg cctggtatca gcagaaacca | 120 |
| ggtaaagccc ctaagctcct gatctactgg gcatcaacac ggcacacagg ggtcccaagc | 180 |
| aggtttctg gcagcggatc aggaaccgaa tttacactga cgatctcgtc tctgcagccc | 240 |
| gaggatttcg ctacttacta ctgtcaacaa tatagtagct atccgctcac tttcggtcag | 300 |
| ggcactaaag tagaaatcaa a | 321 |

<210> SEQ ID NO 67
<211> LENGTH: 121
<212> TYPE: PRT

<213> ORGANISM: Artificial Sequence
<220> FEATURE:
<223> OTHER INFORMATION: VH

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Lys Gln Ala Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Lys Ala Ser Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
        115                 120

<210> SEQ ID NO 68
<211> LENGTH: 107
<212> TYPE: PRT
<213> ORGANISM: Artificial Sequence
<220> FEATURE:
<223> OTHER INFORMATION: VL

<400> SEQUENCE: 68

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys
            100                 105

<210> SEQ ID NO 69
<211> LENGTH: 363
<212> TYPE: DNA
<213> ORGANISM: Artificial Sequence
<220> FEATURE:
<223> OTHER INFORMATION: VH

<400> SEQUENCE: 69
caggtgcagc tggtgcagtc tggggctgag gtgaaaaagc caggcgcttc cgtcaaagtt     60
tcctgcaagg catctggtta ctcttttaca agctattgga tgcactgggt gaagcaggcc    120
cccggacaag ggctcgagtg gattggcatg atcgatcctt ccgatagtga aacacgcttg    180
aatcagaaat tcaaggacaa ggccagtatg accagggata ctagcacaag cactgtatat    240

```
atggagctta gctcactgag atcagaagac acggccgtgt actactgtgc gagacggttt     300
tactatggct ccgactggta tttcgacgtc tggggccagg aaccctggt caccgtctcc      360 tca                                                                   363
```

<210> SEQ ID NO 70
<211> LENGTH: 321
<212> TYPE: DNA
<213> ORGANISM: Artificial Sequence
<220> FEATURE:
<223> OTHER INFORMATION: VL

<400> SEQUENCE: 70

```
gacatacagt tgacccagtc tccttccttc ctgtccgcct ccgtgggcga tagagttacc      60
attacttgca aagctagtca ggacgtgggt accgcagtgg cctggtatca gcagaaacca    120
ggtaaagccc ctaagctcct gatctactgg gcatcaacac ggcacacagg ggtcccaagc    180
aggttttctg gcagcggatc aggaaccgaa tttacactga cgatctcgtc tctgcagccc    240
gaggatttcg ctacttacta ctgtcaacaa tatagtagct atccccctca cttcggtcag    300
ggcactaaag tagaaatcaa a                                              321
```

<210> SEQ ID NO 71
<211> LENGTH: 121
<212> TYPE: PRT
<213> ORGANISM: Artificial Sequence
<220> FEATURE:
<223> OTHER INFORMATION: VH

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Lys Gln Ala Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Lys Ala Ser Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
        115                 120

<210> SEQ ID NO 72
<211> LENGTH: 107
<212> TYPE: PRT
<213> ORGANISM: Artificial Sequence
<220> FEATURE:
<223> OTHER INFORMATION: VL

<400> SEQUENCE: 72

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile

```
                35                  40                  45
Tyr Trp Ala Ser Thr Arg His Thr Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys
            100                 105

<210> SEQ ID NO 73
<211> LENGTH: 363
<212> TYPE: DNA
<213> ORGANISM: Artificial Sequence
<220> FEATURE:
<223> OTHER INFORMATION: VH

<400> SEQUENCE: 73
caggtgcagc tggtgcagtc tggcgctgag gtgaagaaac tggggcctc agtgaaggtt      60 tcctgtaaag caagtggata ctctttcacc agctactgga tgcactgggt gaaacaggcc    120
cccggccaag ggcttgagtg gattggtatg atcgatccat ccgacagcga aactaggctc    180
aaccagaagt tcaaggataa agcgtccttg acagtagata catccacgag cacagtttat    240
atggagctgt ctagtctgcg gtctgaagac accgccgtgt attattgcgc tagacgcttt    300
tattacggct cggactggta ctttgacgtc tggggccagg gaaccctggt caccgtctcc    360
tca                                                                  363

<210> SEQ ID NO 74
<211> LENGTH: 321
<212> TYPE: DNA
<213> ORGANISM: Artificial Sequence
<220> FEATURE:
<223> OTHER INFORMATION: VL

<400> SEQUENCE: 74
gacatacagt tgacccagtc tccttccttc ctgtccgcct ccgtgggcga tagagttacc      60
attacttgca aagctagtca ggacgtgggt accgcagtgg cctggtatca gcagaaacca    120
ggtaaagccc ctaagctcct gatctactgg gcatcaacac ggcacacagg ggtcccaagc    180
aggttttctg gcagcggatc aggaaccgaa tttacactga cgatctcgtc tctgcagccc    240
gaggatttcg ctacttacta ctgtcaacaa tatagtagct atcccctcac tttcggtcag    300
ggcactaaag tagaaatcaa a                                              321

<210> SEQ ID NO 75
<211> LENGTH: 121
<212> TYPE: PRT
<213> ORGANISM: Artificial Sequence
<220> FEATURE:
<223> OTHER INFORMATION: VH

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45
```

Gly Met Ile Asp Pro Ser Asp Ser Glu Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
                100                 105                 110

Gln Gly Thr Leu Val Thr Val Ser Ser
        115                 120

<210> SEQ ID NO 76
<211> LENGTH: 107
<212> TYPE: PRT
<213> ORGANISM: Artificial Sequence
<220> FEATURE:
<223> OTHER INFORMATION: VL

<400> SEQUENCE: 76

Asp Ile Gln Leu Thr Gln Ser Pro Ser Phe Leu Ser Ala Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Lys Ala Pro Lys Leu Leu Ile
            35                  40                  45

Tyr Trp Ala Ser Thr Arg His Thr Gly Val Pro Asp Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys
                100                 105

<210> SEQ ID NO 77
<211> LENGTH: 363
<212> TYPE: DNA
<213> ORGANISM: Artificial Sequence
<220> FEATURE:
<223> OTHER INFORMATION: VH

<400> SEQUENCE: 77
caggtgcagc tggtgcagag tggagctgag gtaaaaaagc ccggcgccag tgtgaaggtt    60
agttgcaagg cctctggata caccttcaca agctattgga tgcactgggt gcgacaagct   120
cctgggcagg gcttgagtg gatgggaatg atcgacccat ccgattcaga aactaggctc   180
aaccagaaat tcaaagatag agtgactatg accagggaca cctccacgag cacagtctac   240
atggaattgt caagcctgcg ctctgaggac acagccgtgt actattgtgc aagacggttt   300
tactatggta gcgattggta ctttgatgtt tggggccagg aaccctggt caccgtctcc   360 tca                                                                 363

<210> SEQ ID NO 78
<211> LENGTH: 321
<212> TYPE: DNA
<213> ORGANISM: Artificial Sequence
<220> FEATURE:
<223> OTHER INFORMATION: VL

<400> SEQUENCE: 78

```
gatattcaac tcacccagag tccatccttc ctgtctgcct cagtgggcga cagagtgtca      60
atcacatgca aggcaagcca ggatgttggc actgctgtgg cttggtatca gcaaaaacca     120
ggtaaggccc ccaaactgct tatttactgg gcatcaaccc ggcacacggg tgtccccgac     180
aggttcagcg gcagtggatc tgggacagag tttacccctga ctatcagctc cctgcagcct    240
gaagactttg ccacttatta ctgtcagcag tactctagct atcctctcac cttcggtcag     300
ggcactaaag tagaaatcaa a                                                321
```

<210> SEQ ID NO 79
<211> LENGTH: 121
<212> TYPE: PRT
<213> ORGANISM: Artificial Sequence
<220> FEATURE:
<223> OTHER INFORMATION: VH

<400> SEQUENCE: 79

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Trp Met His Trp Val Arg Gln Ala Pro Gly Gln Gly Leu Glu Trp Ile
            35                  40                  45

Gly Met Ile Asp Pro Ser Asp Ser Glu Thr Arg Leu Asn Gln Lys Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
                100                 105                 110

Gln Gly Thr Leu Val Thr Val Ser Ser
            115                 120
```

<210> SEQ ID NO 80
<211> LENGTH: 107
<212> TYPE: PRT
<213> ORGANISM: Artificial Sequence
<220> FEATURE:
<223> OTHER INFORMATION: VL

<400> SEQUENCE: 80

```
Asp Ile Gln Leu Thr Gln Ser Pro Ser Phe Leu Ser Ala Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Lys Ala Pro Lys Leu Leu Ile
            35                  40                  45

Tyr Trp Ala Ser Thr Arg His Thr Gly Val Pro Asp Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys
            100                 105
```

<210> SEQ ID NO 81
<211> LENGTH: 363
<212> TYPE: DNA
<213> ORGANISM: Artificial Sequence
<220> FEATURE:
<223> OTHER INFORMATION: VH

<400> SEQUENCE: 81

```
caggtgcaac tcgtgcagtc tggagctgaa gtgaagaaac cgggggcctc agtgaaggtg      60
agttgcaaag catctgggta ctcatttacc agctattgga tgcactgggt gcggcaggcc    120
ccaggacaag gcctggagtg gattggcatg atcgacccct ccgatagtga acgaggctg     180
aaccagaagt ttaaagatcg cgtcaccatg accaggaca caagtacttc tacagtctac     240
atggagttga gcagcctgag atcagaggac acagccgttt actactgtgc tagacgattc    300
tattatggca cgactggta tttcgatgta tggggccagg aaccctggt caccgtctcc      360
tca                                                                   363
```

<210> SEQ ID NO 82
<211> LENGTH: 321
<212> TYPE: DNA
<213> ORGANISM: Artificial Sequence
<220> FEATURE:
<223> OTHER INFORMATION: VL

<400> SEQUENCE: 82

```
gatattcaac tcacccagag tccatccttc ctgtctgcct cagtgggcga cagagtgtca      60
atcacatgca aggcaagcca ggatgttggc actgctgtgg cttggtatca gcaaaaacca    120
ggtaaggccc ccaaactgct tatttactgg gcatcaaccc ggcacacggg tgtccccgac    180
aggttcagcg gcagtggatc tgggacagag tttacccctga ctatcagctc cctgcagcct   240
gaagactttg ccacttatta ctgtcagcag tactctagct atcctctcac cttcggtcag    300
ggcactaaag tagaaatcaa a                                              321
```

<210> SEQ ID NO 83
<211> LENGTH: 121
<212> TYPE: PRT
<213> ORGANISM: Artificial Sequence
<220> FEATURE:
<223> OTHER INFORMATION: VH

<400> SEQUENCE: 83

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Arg Gln Ala Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Lys Ala Ser Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
        115                 120
```

<210> SEQ ID NO 84
<211> LENGTH: 107
<212> TYPE: PRT
<213> ORGANISM: Artificial Sequence
<220> FEATURE:
<223> OTHER INFORMATION: VL

<400> SEQUENCE: 84

```
Asp Ile Gln Leu Thr Gln Ser Pro Ser Phe Leu Ser Ala Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys
            100                 105
```

<210> SEQ ID NO 85
<211> LENGTH: 363
<212> TYPE: DNA
<213> ORGANISM: Artificial Sequence
<220> FEATURE:
<223> OTHER INFORMATION: VH

<400> SEQUENCE: 85

```
caggtgcaac tggtgcagtc tggtgctgag gtgaagaaac caggcgcttc agtcaaggta      60
agctgcaaag caagtggata ctccttcacc tcttattgga tgcactgggt tagacaggcc     120
cctggtcaag gcctcgagtg gattggcatg atcgacccct ctgacagcga aactaggctg     180
aatcagaaat ttaaggacaa ggcctccatg cacgcggata catccacaag caccgtttac     240
atggaactga gctcgctgag aagtgaggac actgccgtgt attactgtgc gagacgcttt     300
tattacgggt cagattggta cttcgatgtg tggggccagg aaccctggt caccgtctcc     360 tca                                                                   363
```

<210> SEQ ID NO 86
<211> LENGTH: 321
<212> TYPE: DNA
<213> ORGANISM: Artificial Sequence
<220> FEATURE:
<223> OTHER INFORMATION: VL

<400> SEQUENCE: 86

```
gatattcaac tcacccagag tccatccttc ctgtctgcct cagtgggcga cagagtgtca      60
atcacatgca aggcaagcca ggatgttggc actgctgtgg cttggtatca gcaaaaacca     120
ggtaaggccc ccaaactgct tatttactgg gcatcaaccc ggcacacggg tgtccccgac     180
aggttcagcg gcagtggatc tgggacagag tttacccctga ctatcagctc ctgcagcct     240 gaagactttg ccacttatta ctgtcagcag tactctagct atcctctcac cttcggtcag     300
ggcactaaag tagaaatcaa a                                                321
```

<210> SEQ ID NO 87

<211> LENGTH: 121
<212> TYPE: PRT
<213> ORGANISM: Artificial Sequence
<220> FEATURE:
<223> OTHER INFORMATION: VH

<400> SEQUENCE: 87

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Ser Tyr
            20                  25                  30
Trp Met His Trp Val Lys Gln Ala Pro Gly Gln Gly Leu Glu Trp Ile
        35                  40                  45
Gly Met Ile Asp Pro Ser Asp Ser Glu Thr Arg Leu Asn Gln Lys Phe
    50                  55                  60
Lys Asp Lys Ala Ser Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Arg Phe Tyr Tyr Gly Ser Asp Trp Tyr Phe Asp Val Trp Gly
            100                 105                 110
Gln Gly Thr Leu Val Thr Val Ser Ser
        115                 120
```

<210> SEQ ID NO 88
<211> LENGTH: 107
<212> TYPE: PRT
<213> ORGANISM: Artificial Sequence
<220> FEATURE:
<223> OTHER INFORMATION: VL

<400> SEQUENCE: 88

```
Asp Ile Gln Leu Thr Gln Ser Pro Ser Phe Leu Ser Ala Ser Val Gly
1               5                   10                  15
Asp Arg Val Ser Ile Thr Cys Lys Ala Ser Gln Asp Val Gly Thr Ala
            20                  25                  30
Val Ala Trp Tyr Gln Gln Lys Pro Gly Lys Ala Pro Lys Leu Leu Ile
        35                  40                  45
Tyr Trp Ala Ser Thr Arg His Thr Gly Val Pro Asp Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Tyr Ser Ser Tyr Pro Leu
                85                  90                  95
Thr Phe Gly Gln Gly Thr Lys Val Glu Ile Lys
            100                 105
```

<210> SEQ ID NO 89
<211> LENGTH: 363
<212> TYPE: DNA
<213> ORGANISM: Artificial Sequence
<220> FEATURE:
<223> OTHER INFORMATION: VH

<400> SEQUENCE: 89

```
caggtgcagc tggtgcagtc tggggctgag gtgaaaaagc caggcgcttc cgtcaaagtt    60
tcctgcaagg catctggtta ctctttaca agctattgga tgcactgggt gaagcaggcc    120
cccggacaag ggctcgagtg gattggcatg atcgatcctt ccgatagtga aacacgcttg    180
```

```
aatcagaaat tcaaggacaa ggccagtatg accagggata ctagcacaag cactgtatat    240
atggagctta gctcactgag atcagaagac acggccgtgt actactgtgc gagacggttt    300
tactatggct ccgactggta tttcgacgtc tggggccagg gaaccctggt caccgtctcc    360
tca                                                                  363
```

<210> SEQ ID NO 90
<211> LENGTH: 321
<212> TYPE: DNA
<213> ORGANISM: Artificial Sequence
<220> FEATURE:
<223> OTHER INFORMATION: VL

<400> SEQUENCE: 90

```
gatattcaac tcacccagag tccatccttc ctgtctgcct cagtgggcga cagagtgtca     60
atcacatgca aggcaagcca ggatgttggc actgctgtgg cttggtatca gcaaaaacca    120
ggtaaggccc ccaaactgct tatttactgg gcatcaaccc ggcacacggg tgtccccgac    180
aggttcagcg gcagtggatc tgggacagag tttacccctga ctatcagctc cctgcagcct    240
gaagactttg ccacttatta ctgtcagcag tactctagct atcctctcac cttcggtcag    300
ggcactaaag tagaaatcaa a                                              321
```

<210> SEQ ID NO 91
<211> LENGTH: 121
<212> TYPE: PRT
<213> ORGANISM: Artificial Sequence
<220> FEATURE:
<223> OTHER INFORMATION: VH

<400> SEQUENCE: 91

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Lys Gln Ala Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Lys Ala Ser Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
        115                 120
```

<210> SEQ ID NO 92
<211> LENGTH: 107
<212> TYPE: PRT
<213> ORGANISM: Artificial Sequence
<220> FEATURE:
<223> OTHER INFORMATION: VL

<400> SEQUENCE: 92

```
Asp Ile Gln Leu Thr Gln Ser Pro Ser Phe Leu Ser Ala Ser Val Gly
1               5                   10                  15

Asp Arg Val Ser Ile Thr Cys Lys Ala Ser Gln Asp Val Gly Thr Ala
            20                  25                  30
```

Val Ala Trp Tyr Gln Gln Lys Pro Gly Lys Ala Pro Lys Leu Leu Ile
            35                  40                  45

Tyr Trp Ala Ser Thr Arg His Thr Gly Val Pro Asp Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys
                100                 105

<210> SEQ ID NO 93
<211> LENGTH: 363
<212> TYPE: DNA
<213> ORGANISM: Artificial Sequence
<220> FEATURE:
<223> OTHER INFORMATION: VH

<400> SEQUENCE: 93
caggtgcagc tggtgcagtc tggcgctgag gtgaagaaac ctggggcctc agtgaaggtt    60
tcctgtaaag caagtggata ctctttcacc agctactgga tgcactgggt gaaacaggcc   120
cccggccaag gcttgagtg gattggtatg atcgatccat ccgacagcga actaggctc    180 aaccagaagt tcaaggataa agcgtccttg acagtagata catccacgag cacagtttat   240
atggagctgt ctagtctgcg gtctgaagac accgccgtgt attattgcgc tagacgcttt   300
tattacggct cggactggta ctttgacgtc tggggccagg gaaccctggt caccgtctcc   360
tca                                                                 363

<210> SEQ ID NO 94
<211> LENGTH: 321
<212> TYPE: DNA
<213> ORGANISM: Artificial Sequence
<220> FEATURE:
<223> OTHER INFORMATION: VL

<400> SEQUENCE: 94
gatattcaac tcacccagag tccatccttc ctgtctgcct cagtgggcga cagagtgtca    60
atcacatgca aggcaagcca ggatgttggc actgctgtgg cttggtatca gcaaaaacca   120
ggtaaggccc ccaaactgct tatttactgg gcatcaaccc ggcacacggg tgtccccgac   180
aggttcagcg gcagtggatc tgggacagag tttaccctga ctatcagctc cctgcagcct   240
gaagactttg ccacttatta ctgtcagcag tactctagct atcctctcac cttcggtcag   300
ggcactaaag tagaaatcaa a                                             321

<210> SEQ ID NO 95
<211> LENGTH: 121
<212> TYPE: PRT
<213> ORGANISM: Artificial Sequence
<220> FEATURE:
<223> OTHER INFORMATION: VH

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met 35                  40                  45
Gly Met Ile Asp Pro Ser Asp Ser Glu Thr Arg Leu Asn Gln Lys Phe
        50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
        115                 120

<210> SEQ ID NO 96
<211> LENGTH: 107
<212> TYPE: PRT
<213> ORGANISM: Artificial Sequence
<220> FEATURE:
<223> OTHER INFORMATION: VL

<400> SEQUENCE: 96

Asp Ile Gln Leu Thr Gln Ser Pro Ser Phe Leu Ser Ala Ser Val Gly
 1               5                  10                  15

Asp Arg Val Ser Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Glu Phe Thr Leu Thr Ile Ser Ser Leu Gln Pro
 65                  70                  75                  80

Glu Asp Phe Ala Asp Tyr Phe Cys Gln Gln Tyr Ser Ser Tyr Pro Leu
                85                  90                  95

Thr Phe Gly Gln Gly Thr Lys Val Glu Ile Lys
            100                 105

<210> SEQ ID NO 97
<211> LENGTH: 363
<212> TYPE: DNA
<213> ORGANISM: Artificial Sequence
<220> FEATURE:
<223> OTHER INFORMATION: VH

<400> SEQUENCE: 97
caggtgcagc tggtgcagag tggagctgag gtaaaaaagc ccggcgccag tgtgaaggtt      60
agttgcaagg cctctggata caccttcaca agctattgga tgcactgggt gcgacaagct     120
cctgggcagg ggcttgagtg gatgggaatg atcgacccat ccgattcaga aactaggctc     180
aaccagaaat tcaaagatag agtgactatg accagggaca cctccacgag cacagtctac     240
atggaattgt caagcctgcg ctctgaggac acagccgtgt actattgtgc aagacggttt     300
tactatggta gcgattggta ctttgatgtt tggggccagg gaaccctggt caccgtctcc     360
tca                                                                   363

<210> SEQ ID NO 98
<211> LENGTH: 321
<212> TYPE: DNA
<213> ORGANISM: Artificial Sequence
<220> FEATURE:
<223> OTHER INFORMATION: VL

<400> SEQUENCE: 98

```
gacatccagt tgacccaatc accatccttt ctgtctgcct ctgtgggaga tagagtctcc      60
attacttgca aggccagtca ggatgtgggg accgctgttg cctggtacca gcaaaaaccc     120
ggaaaggcac ctaaactcct tatctactgg gcatccaccc ggcacacagg agtgccagac     180
aggtttagcg ggtcaggctc tggtacagag ttcactctga caatttctag cctgcagcct     240
gaagacttcg ctgattattt ctgtcagcag tatagcagtt accccctcac gttcggtcag     300
ggcactaaag tagaaatcaa a                                               321
```

<210> SEQ ID NO 99
<211> LENGTH: 121
<212> TYPE: PRT
<213> ORGANISM: Artificial Sequence
<220> FEATURE:
<223> OTHER INFORMATION: VH

<400> SEQUENCE: 99

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Arg Gln Ala Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
        115                 120
```

<210> SEQ ID NO 100
<211> LENGTH: 107
<212> TYPE: PRT
<213> ORGANISM: Artificial Sequence
<220> FEATURE:
<223> OTHER INFORMATION: VL

<400> SEQUENCE: 100

```
Asp Ile Gln Leu Thr Gln Ser Pro Ser Phe Leu Ser Ala Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Asp Tyr Phe Cys Gln Gln Tyr Ser Ser Tyr Pro Leu
                85                  90                  95

Thr Phe Gly Gln Gly Thr Lys Val Glu Ile Lys
            100                 105
```

<210> SEQ ID NO 101
<211> LENGTH: 363
<212> TYPE: DNA
<213> ORGANISM: Artificial Sequence
<220> FEATURE:
<223> OTHER INFORMATION: VH

<400> SEQUENCE: 101

```
caggtgcaac tcgtgcagtc tggagctgaa gtgaagaaac ccggggcctc agtgaaggtg      60
agttgcaaag catctgggta ctcatttacc agctattgga tgcactgggt gcggcaggcc     120
ccaggacaag gcctggagtg gattggcatg atcgaccctt ccgatagtga aacgaggctg     180
aaccagaagt ttaaagatcg cgtcaccatg accagggaca caagtacttc tacagtctac     240
atggagttga gcagcctgag atcagaggac acagccgttt actactgtgc tagacgattc     300
tattatggca gcgactggta tttcgatgta tggggccagg gaaccctggt caccgtctcc     360
tca                                                                   363
```

<210> SEQ ID NO 102
<211> LENGTH: 321
<212> TYPE: DNA
<213> ORGANISM: Artificial Sequence
<220> FEATURE:
<223> OTHER INFORMATION: VL

<400> SEQUENCE: 102

```
gacatccagt tgacccaatc accatccttt ctgtctgcct ctgtgggaga tagagtctcc      60
attacttgca aggccagtca ggatgtgggg accgctgttg cctggtacca gcaaaaaccc     120
ggaaaggcac ctaaactcct tatctactgg gcatccaccc ggcacacagg agtgccagac     180
aggtttagcg gtcaggctc tggtacagag ttcactctga caatttctag cctgcagcct     240
gaagacttcg ctgattattt ctgtcagcag tatagcagtt accccctcac gttcggtcag     300
ggcactaaag tagaaatcaa a                                              321
```

<210> SEQ ID NO 103
<211> LENGTH: 121
<212> TYPE: PRT
<213> ORGANISM: Artificial Sequence
<220> FEATURE:
<223> OTHER INFORMATION: VH

<400> SEQUENCE: 103

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Arg Gln Ala Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Lys Ala Ser Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
```

<210> SEQ ID NO 104
<211> LENGTH: 107
<212> TYPE: PRT
<213> ORGANISM: Artificial Sequence
<220> FEATURE:
<223> OTHER INFORMATION: VL

<400> SEQUENCE: 104

Asp Ile Gln Leu Thr Gln Ser Pro Ser Phe Leu Ser Ala Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Asp Tyr Phe Cys Gln Gln Tyr Ser Ser Tyr Pro Leu
                85                  90                  95

Thr Phe Gly Gln Gly Thr Lys Val Glu Ile Lys
            100                 105

<210> SEQ ID NO 105
<211> LENGTH: 363
<212> TYPE: DNA
<213> ORGANISM: Artificial Sequence
<220> FEATURE:
<223> OTHER INFORMATION: VH

<400> SEQUENCE: 105
caggtgcaac tggtgcagtc tggtgctgag gtgaagaaac caggcgcttc agtcaaggta    60
agctgcaaag caagtggata ctccttcacc tcttattgga tgcactgggt tagacaggcc   120
cctggtcaag cctcgagtg gattggcatg atcgacccct ctgacagcga aactaggctg   180
aatcagaaat ttaaggacaa ggcctccatg acacgggata catccacaag caccgtttac   240
atggaactga gctcgctgag aagtgaggac actgccgtgt attactgtgc gagacgcttt   300
tattacgggt cagattggta cttcgatgtg tggggccagg gaaccctggt caccgtctcc   360
tca                                                                 363

<210> SEQ ID NO 106
<211> LENGTH: 321
<212> TYPE: DNA
<213> ORGANISM: Artificial Sequence
<220> FEATURE:
<223> OTHER INFORMATION: VL

<400> SEQUENCE: 106
gacatccagt tgacccaatc accatccttt ctgtctgcct ctgtgggaga tagagtctcc    60
attacttgca aggccagtca ggatgtgggg accgctgttg cctggtacca gcaaaaaccc   120
ggaaaggcac ctaaactcct tatctactgg gcatccaccc ggcacacagg agtgccagac   180
aggtttagcg ggtcaggctc tggtacagag ttcactctga caatttctag cctgcagcct   240
gaagacttcg ctgattattt ctgtcagcag tatagcagtt accccctcac gttcggtcag   300
ggcactaaag tagaaatcaa a                                             321

<210> SEQ ID NO 107
<211> LENGTH: 121
<212> TYPE: PRT
<213> ORGANISM: Artificial Sequence
<220> FEATURE:
<223> OTHER INFORMATION: VH

<400> SEQUENCE: 107

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Lys Gln Ala Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Lys Ala Ser Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
        115                 120
```

<210> SEQ ID NO 108
<211> LENGTH: 107
<212> TYPE: PRT
<213> ORGANISM: Artificial Sequence
<220> FEATURE:
<223> OTHER INFORMATION: VL

<400> SEQUENCE: 108

```
Asp Ile Gln Leu Thr Gln Ser Pro Ser Phe Leu Ser Ala Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Asp Tyr Phe Cys Gln Gln Tyr Ser Ser Tyr Pro Leu
                85                  90                  95

Thr Phe Gly Gln Gly Thr Lys Val Glu Ile Lys
            100                 105
```

<210> SEQ ID NO 109
<211> LENGTH: 363
<212> TYPE: DNA
<213> ORGANISM: Artificial Sequence
<220> FEATURE:
<223> OTHER INFORMATION: VH

<400> SEQUENCE: 109

```
caggtgcagc tggtgcagtc tggggctgag gtgaaaaagc caggcgcttc cgtcaaagtt      60
tcctgcaagg catctggtta ctcttttaca agctattgga tgcactgggt gaagcaggcc     120
```

```
cccggacaag ggctcgagtg gattggcatg atcgatcctt ccgatagtga aacacgcttg      180
aatcagaaat tcaaggacaa ggccagtatg accagggata ctagcacaag cactgtatat      240
atggagctta gctcactgag atcagaagac acggccgtgt actactgtgc gagacggttt      300
tactatggct ccgactggta tttcgacgtc tggggccagg aaccctggt caccgtctcc       360 tca                                                                    363
```

<210> SEQ ID NO 110
<211> LENGTH: 321
<212> TYPE: DNA
<213> ORGANISM: Artificial Sequence
<220> FEATURE:
<223> OTHER INFORMATION: VL

<400> SEQUENCE: 110

```
gacatccagt tgacccaatc accatccttt ctgtctgcct ctgtgggaga tagagtctcc       60
attacttgca aggccagtca ggatgtgggg accgctgttg cctggtacca gcaaaaaccc      120
ggaaaggcac ctaaactcct tatctactgg gcatccaccc ggcacacagg agtgccagac      180
aggtttagcg ggtcaggctc tggtacagag ttcactctga caatttctag cctgcagcct      240
gaagacttcg ctgattattt ctgtcagcag tatagcagtt accccctcac gttcggtcag      300
ggcactaaag tagaaatcaa a                                                321
```

<210> SEQ ID NO 111
<211> LENGTH: 121
<212> TYPE: PRT
<213> ORGANISM: Artificial Sequence
<220> FEATURE:
<223> OTHER INFORMATION: VH

<400> SEQUENCE: 111

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Lys Gln Ala Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Lys Ala Ser Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Phe Tyr Tyr Gly Ser Asp Trp Tyr Phe Asp Val Trp Gly
            100                 105                 110

Gln Gly Thr Leu Val Thr Val Ser Ser
        115                 120
```

<210> SEQ ID NO 112
<211> LENGTH: 107
<212> TYPE: PRT
<213> ORGANISM: Artificial Sequence
<220> FEATURE:
<223> OTHER INFORMATION: VL

<400> SEQUENCE: 112

```
Asp Ile Gln Leu Thr Gln Ser Pro Ser Phe Leu Ser Ala Ser Val Gly
1               5                   10                  15
```

```
Asp Arg Val Ser Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Asp Tyr Phe Cys Gln Gln Tyr Ser Ser Tyr Pro Leu
                85                  90                  95

Thr Phe Gly Gln Gly Thr Lys Val Glu Ile Lys
            100                 105
```

<210> SEQ ID NO 113
<211> LENGTH: 363
<212> TYPE: DNA
<213> ORGANISM: Artificial Sequence
<220> FEATURE:
<223> OTHER INFORMATION: VH

<400> SEQUENCE: 113

```
caggtgcagc tggtgcagtc tggcgctgag gtgaagaaac ctggggcctc agtgaaggtt      60
tcctgtaaag caagtggata ctctttcacc agctactgga tgcactgggt gaaacaggcc     120
cccggccaag gcttgagtg gattggtatg atcgatccat ccgacagcga aactaggctc      180
aaccagaagt tcaaggataa agcgtccttg acagtagata catccacgag cacagtttat     240
atggagctgt ctagtctgcg gtctgaagac accgccgtgt attattgcgc tagacgcttt     300
tattacggct cggactggta ctttgacgtc tggggccagg gaaccctggt caccgtctcc     360
tca                                                                    363
```

<210> SEQ ID NO 114
<211> LENGTH: 321
<212> TYPE: DNA
<213> ORGANISM: Artificial Sequence
<220> FEATURE:
<223> OTHER INFORMATION: VL

<400> SEQUENCE: 114

```
gacatccagt tgacccaatc accatccttt ctgtctgcct ctgtgggaga tagagtctcc      60
attacttgca aggccagtca ggatgtgggg accgctgttg cctggtacca gcaaaaaccc     120
ggaaaggcac ctaaactcct tatctactgg gcatccaccc ggcacacagg agtgccagac     180
aggtttagcg ggtcaggctc tggtacagag ttcactctga caatttctag cctgcagcct     240
gaagacttcg ctgattattt ctgtcagcag tatagcagtt accccctcac gttcggtcag     300
ggcactaaag tagaaatcaa a                                                321
```

<210> SEQ ID NO 115
<211> LENGTH: 18
<212> TYPE: PRT
<213> ORGANISM: Artificial Sequence
<220> FEATURE:
<223> OTHER INFORMATION: epitope

<400> SEQUENCE: 115

```
Gln Arg Thr Trp Lys Glu Tyr Lys Val Gly Phe Gly Asn Pro Ser Gly
1               5                   10                  15

Glu Tyr
```

```
<210> SEQ ID NO 116
<211> LENGTH: 11
<212> TYPE: PRT
<213> ORGANISM: Artificial Sequence
<220> FEATURE:
<223> OTHER INFORMATION: epitope

<400> SEQUENCE: 116

Lys Ser Gly His Thr Thr Asn Gly Ile Tyr Thr
1               5                   10

<210> SEQ ID NO 117
<211> LENGTH: 7
<212> TYPE: PRT
<213> ORGANISM: Artificial Sequence
<220> FEATURE:
<223> OTHER INFORMATION: epitope

<400> SEQUENCE: 117

Glu Ala Gly Gly Gly Gly Trp
1               5
```

ANTI-ANGIOPOIETIN-2 ANTIBODIES THAT INDUCE TIE2 ACTIVATION

CROSS REFERENCE TO RELATED APPLICATIONS

This application is a continuation of International Patent Application No. PCT/KR2019/001983, filed Feb. 19, 2019, which claims priority from Korean Patent Application No. 10-2019-0018769, filed Feb. 18, 2019 and U.S. Provisional Application No. 62/633,038, filed Feb. 20, 2018, the contents of each of which are incorporated herein by reference in their entirety.

SEQUENCE LISTING

This application contains a Sequence Listing in computer readable form entitled "2020-09-10_01262-0002-00US_Seq_List_ST25.txt," created Sep. 10, 2020, having a size of 85,471 bytes, which is incorporated by reference herein.

FIELD OF THE INVENTION

The present invention includes an anti-Ang2 antibodies or an antigen-binding fragment thereof, which bind specifically to angiopoietin-2 (Ang2) known as a ligand that controls blood vessel formation and maintenance, a pharmaceutical composition containing the same, a nucleic acid encoding the same, a vector including the nucleic acid, an host cell transformed with the vector, and a method for producing the antibody or antigen-binding fragment thereof.

BACKGROUND ART

Angiogenesis occurs dynamically by a variety of regulatory factors during the development, growth, maintenance, and homeostasis of an organism. Blood vessels newly formed in this process act as transport channels for various biomaterials such as nutrients, oxygen, and hormones in the surrounding cells. Functionally and structurally abnormal blood vessels are the direct or indirect cause for the initiation and progression of various diseases. Tumor blood vessels aggravate hypoxia due to their defective function and structure, resulting in tumor progression and metastasis to other tissues, and also in the poor delivery of anticancer drugs into the core of the tumor mass. Defective blood vessels are also found in other various diseases and conditions, in addition to cancer. Examples thereof include various ocular diseases (e.g., diabetic macular edema, wet age-related macular degeneration), viral infections, and acute inflammatory responses such as sepsis. Thus, if a therapeutic agent capable of normalizing pathologic blood vessels is available, it can be applied to the treatment of various patients with vascular abnormalities.

The angiopoietin family plays an important role in the formation and maintenance of blood vessels, and is comprised of four angiopoietins (Ang1, Ang2, Ang3, and Ang4). Angiopoietin-1 (Ang1) binds to the Tie2 receptor present on the surface of vascular endothelial cells to phosphorylate and activate Tie2 receptor, resulting in stabilization of blood vessels. On the other hand, angiopoietin-2 (Ang2) binds to the Tie2 receptor, but acts as an antagonist to induce inactivation of the Tie2 receptor, resulting in destabilization of blood vessels and leakage of blood vessels. It was reported that the expression level of Ang2 is highly increased in the blood of cancer patients, ocular diseases, viral and bacterial infections and inflammatory diseases (Saharinen P et al., 2017, Nature Review Drug Discovery). However, Ang2 is also known to act as an agonist to induce activation of the Tie2 receptor in several processes, including lymphatic tube formation and maintenance, and thus it is believed that Ang2 performs various functions depending on the context.

Ang2-binding antibodies have been reported in several literatures (e.g., U.S. Pat. Nos. 7,658,924, and 8,987,420). It is known that most of the Ang2 antibodies reported so far inhibit the binding of Ang2 to Tie2 and thus inhibiting the formation of new blood vessel through such Ang2 neutralization efficacy. Currently, various Ang2 antibodies are being clinically tested in various cancer patients, but their anti-cancer efficacy is known to be insufficient. For example, Phase 3 clinical trials conducted by Amgen showed that the anti-cancer efficacy of the Ang2 antibody in ovarian cancer patients was insignificant (Marth C et al., 2017, Eur. J. Cancer).

In addition to antibodies, recombinant proteins that bind directly to the Tie2 receptor to induce phosphorylation and activation of Tie2 have also been reported. Examples thereof include COMP-Ang1 (Cho et al., 2004, PNAS) and Vasculotide (David S et al., 2011, Am J Physiol Lung Cell Mol Physiol) peptide consisting of five angiopoietin-1 protein fragments. However, it is considered that these proteins have a very short half-life and unstable physicochemical properties. In addition, there is a phosphatase called VE-PTP that removes a phosphate group from phosphorylated Tie2 to inactivate the Tie2, and a low molecular compound (AKB-9778) was also developed, which indirectly maintains Tie2 activity by inhibiting the activity of the enzyme VE-PTP (Goel S, 2013, J Natl Cancer Inst). However, this compound has the disadvantage of activating other receptors besides Tie2 (Frye M, 2015, J Exp. Med, Hayashi M, 2013, Nature Communication, Mellberg S et al., 2009, FASEB J.).

SUMMARY OF THE INVENTION

The present invention is directed to an antibody or antigen-binding fragment thereof that specifically binds human Angiopoietin-2 and induces Tie2 activation, wherein the antibody or antigen-binding fragment thereof binds to amino acids 289-299 of SEQ ID NO: 1, amino acids 316-322 of SEQ ID NO: 1, or amino acids 336-353 of SEQ ID NO: 1, as determined by hydrogen/deuterium exchange method.

The antibody or antigen-binding fragment thereof may bind to human and mouse Ang2. The antibody may be polyclonal or monoclonal. The antigen-binding fragment may be scFv or Fab. The antibody or fragment thereof may be humanized.

In another aspect, the invention is directed to an antibody or antigen-binding fragment that includes:

(a) the complementarity determining regions (CDRs) of a heavy chain variable region having the HCDR1 amino acid sequence of SEQ ID NO: 3, the HCDR2 amino acid sequence of SEQ ID NO: 4, and the HCDR3 amino acid sequence of SEQ ID NO: 5; and (b) the CDRs of a light chain variable region comprising the LCDR1 amino acid sequence of SEQ ID NO: 6, the LCDR2 amino acid sequence of SEQ ID NO: 7, and the LCDR3 amino acid sequence of SEQ ID NO: 8.

In another aspect, the invention is directed to an antibody or antigen-binding fragment that includes:

(a) the complementarity determining regions (CDRs) of a heavy chain variable region having the HCDR1 amino acid sequence of SEQ ID NO: 13, the HCDR2 amino acid sequence of SEQ ID NO: 14, and the HCDR3 amino acid sequence of SEQ ID NO: 15; and (b) the CDRs of a light chain variable region comprising the LCDR1 amino acid sequence of SEQ ID NO: 16, the LCDR2 amino acid sequence of SEQ ID NO: 17, and the LCDR3 amino acid sequence of SEQ ID NO: 18.

In one aspect, the invention is directed to an antibody or antigen-binding fragment thereof that comprises the complementary determining regions (CDRs) of an antibody produced from a cell line deposited with accession number KCLRF-BP-00417 or KCLRF-BP-00418.

In yet another aspect, the invention is directed to a pharmaceutical composition comprising a pharmaceutically effective amount of the antibody or antigen-binding fragment thereof described above, in association with a pharmaceutically acceptable carrier. The pharmaceutical composition may further include a small molecule inhibitor used in chemotherapy or a vascular endothelial growth factor (VEGF) antagonist. In one aspect, the VEGF antagonist may be an anti-VEGF antibody, a VEGF inhibiting fusion protein, or a small molecule kinase inhibitor.

In yet another aspect, the invention is directed to a method for inhibiting tumor growth in a patient, comprising administering to the patient a pharmaceutical composition comprising an antibody or antigen-binding fragment described above. The method may further include administering a small molecule inhibitor used in chemotherapy or a vascular endothelial growth factor (VEGF) antagonist simultaneously or step-wise with the administration of the inventive antibody or fragment thereof. The VEGF antagonist may be an anti-VEGF antibody, a VEGF inhibiting fusion protein, or a small molecule kinase inhibitor.

In yet another aspect, the invention is directed to a method for suppressing choroidal neovascularization, inhibiting ocular vascular leakage, or simultaneously triggering regeneration of choriocapillary in an ocular disease patient, the method comprising administering to the patient the pharmaceutical composition described above. The method may further include administering a small molecule inhibitor used in chemotherapy or a vascular endothelial growth factor (VEGF) antagonist simultaneously or step-wise with the administration of the inventive antibody or fragment thereof. The VEGF antagonist may be an anti-VEGF antibody, a VEGF inhibiting fusion protein, or a small molecule kinase inhibitor. The ocular disease is wet age-related macular degeneration (wAMD), diabetic macular edema (DME), or diabetic retinopathy (DR).

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIGS. 10A-10C. Tumor vessel normalization effect by humanized 2C8H11 antibody. PDGFβ$^+$ pericyte coverage (FIGS. 10A and 10B) on tumor and CD31$^+$ BVs (FIGS. 10A and 10C) in intratumoral region were compared in LLC subcutaneous tumor model. Scale bar, 100 μm. n=5 for each group. Values are mean±SD. *p<0.05 versus Fc; #p<0.05 versus Fc+Cpt.

FIGS. 11A-11C. Hypoxia reduction and perfusion increase in tumor blood vessels by humanized 2C8H11 antibody. Lectin perfusion of tumor vessels (FIGS. 11A and 11B) and Hypoxyprobe$^+$ hypoxic area (FIGS. 11A and 11C) were analyzed and compared in LLC tumor. Hypoxyprobe$^+$ area is presented as a percentage per total sectional area. Scale bar, 100 μm. n=5 for each group. Values are mean±SD. *p<0.05 versus Fc; #p<0.05 versus Fc+Cpt.

FIGS. 13A-13D. CNV regression and vascular leakage suppression by intravitreous injection of 2C8H11 antibody in laser-induced CNV model. The intravitreal administration of antibodies was performed at 7 days after laser photocoagulation (FIG. 13A-13B). CD31$^+$ CNV volumes (FIG. 13C) were measured and leaky areas around CNV were calculated as the total measured hyper-fluorescent areas in FA images divided by the total measured CNV areas in ICGA images at 6 and/or 14 days after laser photocoagulation (FIG. 13D). Scale bar, 100 n=11 for each group. Values are mean±SD. ***p<0.001 by one-way ANOVA followed by Student-Newman-Keuls post-test; ###p<0.001 by paired Student's t-test.

FIGS. 14A-14D. CNV regression and choriocapillary regeneration by intravitreous injection of 2C8H11 antibody. The intravitreous administration of antibodies was performed at 7 days after laser photocoagulation (FIGS. 14A-14B). The CNV volumes (area demarcated by the white dotted boundary) (FIG. 14C) and the avascular space (area demarcated by the yellow dotted boundary) (FIG. 14D) surrounding the CNV were measured by OCTA imaging of eyes at 6, 14, 21 and 35 days after laser photocoagulation. n=11 for each group. Values are mean±SD. *p<0.05, **p<0.005 vs. Fc by one-way ANOVA followed by Student-Newman-Keuls post-test.

DETAILED DESCRIPTION OF THE INVENTION

Figure 1:
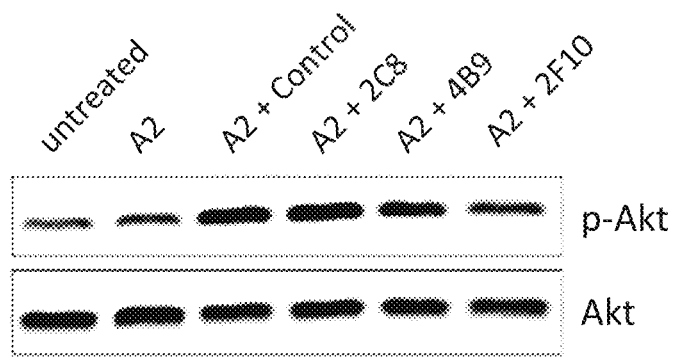
FIG. 1. Akt phosphorylation induced by anti-Ang2 antibodies. HUVECs were serum-starved for 6 hrs and incubated with COMP-Ang1 (CA1, 0.5 µg/ml) or anti-Ang2 antibodies (control, 2C8, 4B9, 2F10 and 4E2 respectively) in the absence or presence of human Ang2 (1 µg/ml) for 30 min. Cell lysates were subjected to SDS-PAGE/Western blotting and blots were probed with anti-phospho-Akt (S473) or anti-Akt antibody.

Unless defined otherwise, all technical and scientific terms used herein have the same meaning as those appreciated by those skilled in the field to which the present disclosure pertains. In general, nomenclature used herein is well-known in the art and is ordinarily used.

In the present application, "a" and "an" are used to refer to both single and a plurality of objects.

In one aspect, the present invention is directed to an antibody or antigen-binding fragment thereof that specifically binds human Angiopoietin-2 and induces Tie2 activation, wherein the antibody or antigen-binding fragment thereof binds to amino acids of SEQ ID NO: 115, amino acids of SEQ ID NO: 116, or amino acids of SEQ ID NO: 117.

The amino acids of SEQ ID NO: 115 is corresponding to the amino acids 336-353 of SEQ ID NO: 1, the amino acids of SEQ ID NO: 116 is corresponding to the amino acids 289-299 of SEQ ID NO: 1, and the amino acids of SEQ ID NO: 117 is corresponding to the amino acids 316-322 of SEQ ID NO: 1.

As herein used, the term "antibody specifically binding to Ang2" refers to antibody that binds to Ang2 resulting in inhibition of the biological activity of Ang2, and is used interchangeably with "anti-Ang2 antibody", "Ang2-binding antibody". The "antibody" used herein is an immunoglobulin molecule which is immunologically reactive to a specific antigen, and means a protein molecule acting as a receptor that specifically recognizes an antigen, and may include all of a polyclonal antibody, a monoclonal antibody (single clone antibody), a whole antibody, and an antibody fragment. Further, the antibody may include a chimeric antibody (e.g., humanized murine antibody) and a bivalent or bispecific molecule (e.g., bispecific antibody), a diabody, a triabody, and a tetrabody.

The whole antibody has a structure having two full length light chains and two full length heavy chains, and each light chain may be linked to a heavy chain via a disulfide bond. The whole antibody includes IgA, IgD, IgE, IgM, and IgG, and the IgG is a subtype, and includes IgG1, IgG2, IgG3, and IgG4.

In the present disclosure, the antibody or antigen-binding fragment thereof may bind to human and mouse Ang2.

The antibody fragment means a fragment retaining an antigen-binding function, and includes Fab, Fab', F(ab')$_2$, scFv, and Fv, etc.

The Fab has a structure of variable regions of a light chain and a heavy chain and a constant region of the light chain and a first constant region (CH1 domain) of the heavy chain, and has one antigen-binding site. The Fab' is different from the Fab in that the Fab' has a hinge region including one or more cysteine residues at C terminal of a heavy chain CH1 domain. The F(ab')$_2$ antibody is produced by achieving the disulfide bonding of the cysteine residue in the hinge region of the Fab'.

The Fv (variable fragment) refers to the minimum antibody fragment only having the heavy chain variable region and the light chain variable region. In double-stranded Fv (dsFv), the heavy chain variable region and the light chain variable region are linked by the disulfide bond. In the single chain Fv (scFv), the heavy chain variable region and the light chain variable region generally are linked by a covalent bond using a peptide linker. These antibody fragment may be obtained by using a proteolytic enzyme (for example, the Fab may be obtained by restriction-cutting the whole antibody with papain, and F(ab')2 fragment may be obtained by cutting with pepsin), and may be constructed by a recombinant DNA technology (for example, amplification by PCR (Polymerase Chain Reaction) method using DNA encoding the heavy chain of the antibody or the variable region thereof and DNA encoding the light chain or the variable region thereof as a template and using a primer pair, and amplification with combination of the DNA encoding the peptide linker of the primer pair allowing both ends thereof to link to the heavy chain or the variable region thereof and the light chain or the variable region thereof, respectively).

In the present disclosure, the antibody or antigen-binding fragment thereof may be humanized. Preferably, the anti-Ang2 antibody according to the present invention may be a fully human antibody selected from a human antibody library, but is not limited thereto.

The antibody or antigen-binding fragment thereof according to the present invention is characterized by containing a heavy chain variable region including a heavy chain CDR1 having an amino acid sequence of SEQ ID NO: 3, a heavy chain CDR2 having an amino acid sequence of SEQ ID NO: 4, a heavy chain CDR3 having an amino acid sequence of SEQ ID NO: 5; and a light chain variable region including a light chain CDR1 having an amino acid sequence of SEQ ID NO: 6, a light chain CDR2 having an amino acid sequence of SEQ ID NO: 7, a light chain CDR3 having an amino acid sequence of SEQ ID NO: 8.

The antibody or antigen-binding fragment thereof according to the present invention is characterized by containing a heavy chain variable region including a heavy chain CDR1 having an amino acid sequence of SEQ ID NO: 13, a heavy chain CDR2 having an amino acid sequence of SEQ ID NO: 14, a heavy chain CDR3 having an amino acid sequence of SEQ ID NO: 15; and a light chain variable region including a light chain CDR1 having an amino acid sequence of SEQ ID NO: 16, a light chain CDR2 having an amino acid sequence of SEQ ID NO: 17, a light chain CDR3 having an amino acid sequence of SEQ ID NO: 18.

In the present invention, the antibody or antigen-binding fragment thereof is characterized by containing the heavy chain variable region including the amino acid sequence of SEQ ID NOs: 9, 19, 43, 47, 51, 55, 59, 63, 67, 71, 75, 79, 83, 87, 91, 95, 99, 103, 107 or 111; and the light chain variable region including the amino acid sequence of SEQ ID NOs: 11, 21, 44, 48, 52, 56, 60, 64, 68, 72, 76, 80, 84, 88, 92, 96, 100, 104, 108 or 112, but is not limited thereto.

The amino acid sequence of the antibody may be substituted by conservative substitution. The "conservative substitution" refers to modification of polypeptide including substitution of at least one amino acid with an amino acid having similar biochemical properties to corresponding polypeptide without causing loss of biological or biochemical function. "Conservative amino acid substitution" refers to a substitution in which an amino acid residue is replaced with an amino acid residue having similar side chains. Classes of the amino acid residues having similar side chains are defined in the art. These classes include amino acids having basic side chains (e.g., lysine, arginine, histidine), amino acids having acidic side chains (e.g., aspartic acid, glutamic acid), amino acids having uncharged polar side chains (e.g., glycine, asparagine, glutamine, serine, threonine, tyrosine, cysteine), amino acids having non-polar side chains (e.g., alanine, valine, leucine, isoleucine, proline, phenylalanine, methionine, tryptophan), amino acids having beta-branched side chains (e.g., threonine, valine, isoleucine), and amino acids having aromatic side chains (e.g., tyrosine, phenylalanine, tryptophan, histidine). It is anticipated that the antibody of the present invention is able to still retain an activity while having the conservative amino acid substitution.

In the present invention, the antibody or antigen-binding fragment thereof is characterized by containing the complementary determining regions (CDRs) of an antibody produced from a cell line deposited with accession number KCLRF-BP-00417 or KCLRF-BP-00418.

The inventive anti-Ang2 antibody sequences may vary from the sequences provided in the present application. For example, amino sequences may vary from those set out above in that (a) the variable regions may be segregated away from the constant domains of the light chains, (b) the amino acids may vary from those set out above while not drastically affecting the chemical properties of the residues thereby (so-called conservative substitutions), (c) the amino acids may vary from those set out above by a given percentage, e.g., 80%, 85%, 90%, 91%, 92%, 93%, 94%, 95%, 96%, 97%, 98% or 99% homology. Alternatively, the nucleic acids encoding the antibodies may (a) be segregated away from the constant domains of the light chains, (b) vary from those set out above while not changing the residues coded thereby, or (c) may vary from those set out above by a given percentage, e.g., 70%, 75%, 80%, 85%, 90%, 91%, 92%, 93%, 94%, 95%, 96%, 97%, 98% or 99% homology.

In making conservative changes in amino acid sequence, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is also understood in the art that the substitution of like amino acids can be made effectively on the basis of hydrophilicity. For instance, the greatest local average hydrophilicity of a protein, as governed by the hydrophilicity of its adjacent amino acids, correlates with a biological property of the protein. It is understood that an amino acid can be substituted for another having a similar hydrophilicity and produce a biologically or immunologically modified protein. In such changes, the substitution of amino acids whose hydrophilicity values are within +/−2 is preferred, those that are within +/−1 are particularly preferred, and those within +/−0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

In another aspect, the present invention relates to a pharmaceutical composition containing the antibody or antigen-binding fragment thereof as an active ingredient.

The pharmaceutical composition is characterized by containing a pharmaceutically effective amount of the antibody or an antigen-binding fragment thereof according to the invention and a pharmaceutically acceptable carrier.

The pharmaceutical composition may further include a small molecule inhibitor used in chemotherapy or a vascular endothelial growth factor (VEGF) antagonist. The VEGF antagonist may be an anti-VEGF antibody, a VEGF inhibiting fusion protein, or a small molecule kinase inhibitor.

In another aspect, the present invention relates to a pharmaceutical composition for preventing or treating ocular disease containing the antibody or antigen-binding fragment thereof as an active ingredient.

In another aspect, the present invention relates to a method for suppressing choroidal neovascularization, inhibiting ocular vascular leakage, or simultaneously triggering regeneration of choriocapillary in an ocular disease patient, the method comprising administering to the patient the pharmaceutical composition described above.

The pharmaceutical composition for preventing or treating ocular disease may further include a small molecule inhibitor used in chemotherapy or a vascular endothelial growth factor (VEGF) antagonist. The VEGF antagonist may be an anti-VEGF antibody, a VEGF inhibiting fusion protein, or a small molecule kinase inhibitor.

The method may further include administering a small molecule inhibitor used in chemotherapy or a vascular endothelial growth factor (VEGF) antagonist simultaneously or step-wise with the administration of the inventive antibody or fragment thereof. The VEGF antagonist may be an anti-VEGF antibody, a VEGF inhibiting fusion protein, or a small molecule kinase inhibitor.

The anti-Ang2 antibody or antigen-binding fragment thereof has a function of inhibiting abnormal angiogenesis by inhibiting the function of Ang2, and thus has an effect of preventing or treating ocular diseases accompanied by vascular abnormalities.

As herein used, the term "preventing" refers to any action that inhibits or slows the progression of ocular diseases by administration of a composition according to the present invention, and the term "treating" refers to inhibiting, alleviating, or eliminating the development of ocular diseases.

In the present invention, the ocular disease is wet age-related macular degeneration (wAMD), diabetic macular edema (DME), or diabetic retinopathy (DR), but is not limited thereto.

As herein used, the term "macular degeneration" refers to a condition in which neovascularization abnormally grows, so causes macula damage and affects vision. Macular degeneration occurs mainly in over 50 years of age and is divided into non-exudative (dry type) or exudative (wet type). In particular, in the case of wet AMD, blindness can be caused. The cause of the AMD has not yet been clarified, but it is known that risk factors are age; and environmental factors including smoking, hypertension, obesity, genetic predisposition, excessive UV exposure, low serum antioxidant concentrations and the like.

As herein used, the term "macular edema" refers to the swelling of the macula of the retina, and the swelling occurs due to fluid leakage from the retinal blood vessels. Blood leaks from the weak blood vessel wall, enters the localized area of the retinal macula which is the color-sensing nerve ending and in which the retinal conic is abundant. The image is then faded to the right of the center or center of the center area. Visual acuity decreases gradually over several months. As herein used, the term "diabetic retinopathy" refers to a complication of the eye in which visual acuity is reduced due to disturbance of microcirculation of the retina due to peripheral circulatory disorder caused by diabetes. Initially, it can cause light problems of visual acuity, but eventually it can cause blindness. Diabetic retinopathy can occur in anyone with Type 1 diabetes or Type 2 diabetes.

The present invention provides a pharmaceutical composition including a therapeutically effective amount of anti-Ang2 antibody and a pharmaceutically acceptable carrier. The "pharmaceutically acceptable carrier" is a material that is able to be added in the active ingredient to help formulation or stabilization of the preparation, and it does not cause significant adverse toxicological effects to patients.

The carrier refers to a carrier or diluent that does not inhibit biological activity and properties of an administered compound without stimulating the patients. The pharmaceutically acceptable carrier in the composition to be formulated as a liquid solution is sterilized and is suitable for a living body. Saline, sterile water, Ringer's solution, buffered saline, albumin injection solution, dextrose solution, maltodextrin solution, glycerol, ethanol may be used as the carrier, or at least one component thereof may be mixed to be used, and other conventional additives such as an antioxidant, buffer, a bacteriostatic agent, etc., may be added as needed. In addition, the composition may be prepared into formulations for injection, such as an aqueous solution, suspension, emulsion, etc., pill, a capsule, a granule or a tablet by further adding diluent, dispersant, surfactant, binder and lubricant thereto. Other carriers are described in, for example, [Remington's Pharmaceutical Sciences (E. W. Martin)]. The composition may contain the therapeutically effective amount of at least one anti-Ang2 antibody.

The pharmaceutically acceptable carrier includes sterile aqueous solution or dispersion and sterile powder for preparing extemporaneous sterile injectable solution or dispersion. The use of such media and agents for pharmaceutical active materials is known in the art. The composition is preferably formulated for parenteral injection. The composition may be formulated as a solution, a micro-emulsion, a liposome, or other ordered structures suitable for high drug concentration. The carrier may be, for example, a solvent or dispersion medium containing water, ethanol, polyol (for example, glycerol, propylene glycol and liquid polyethylene glycol, etc.) and suitable mixtures thereof. In some cases, the composition may include, isotonic agent, for example, sugar, polyalcohols such as mannitol, sorbitol, or sodium chloride. The sterile injectable solution may be prepared by incorporating a required amount of active compound into an appropriate solvent with one kind of the above-described components or a combination thereof, followed by sterile micro filtration as needed. In general, the dispersion is prepared by incorporating the active compound into a sterile vehicle containing basic dispersion medium and other required components from the above-described components. The sterile powder for preparing the sterile injectable solution is obtained by vacuum drying and freeze-drying (lyophilization) active ingredient powder and any additional desirable component powder from previously sterile-filtered solution.

The pharmaceutical composition may be administered orally or parenterally in the dosage and frequency that may vary depending on severity of suffering patients. The composition may be administered to a patient as a bolus or by continuous infusion as needed. For example, the bolus administration of the antibody of the present invention which is presented as a Fab fragment may have an amount of 0.0025 to 100 mg/kg body weight, 0.025 to 0.25 mg/kg, 0.010 to 0.10 mg/kg or 0.10 to 0.50 mg/kg. For the continuous infusion, the antibody of the present invention which is presented as the Fab fragment may be administered at 0.001 to 100 mg/kg kg/min, 0.0125 to 1.25 mg/kg/min, 0.010 to 0.75 mg/kg/min, 0.010 to 1.0 mg/kg/min or 0.10 to 0.50 mg/kg/min for 1 to 24 hours, 1 to 12 hours, 2 to 12 hours, 6 to 12 hours, 2 to 8 hours, or 1 to 2 hours. When the antibody of the present invention which is presented as a full-length antibody (having a complete constant region is administered, an administration amount may be about 1 to 10 mg/kg body weight, 2 to 8 mg/kg, or 5 to 6 mg/kg. The full-length antibody is typically administered via injection that lasts for 30 minutes to 35 minutes. An administration frequency depends on the severity of the condition. The frequency may be 3 times every week to once in a week or in two weeks.

In addition, the composition may be administered to a patient via a subcutaneous injection. For example, the anti-Ang2 antibody having an administration amount of 10 to 100 mg may be weekly, biweekly, or monthly administered to a patient through subcutaneous injection.

As used herein, the "therapeutically effective amount" means an amount sufficient to treat diseases at a reasonable benefit/risk ratio applicable for medical treatment, and an amount of a combination of the anti-Ang2 antibody. The exact amount may vary depending on a number of factors that include components and physical characteristics of a therapeutic composition, intended patient population, individual patient considerations, etc., but are not limited thereto, and may be easily determined by those skilled in the art. When completely considering these factors, it is important to administer the minimum amount sufficient to obtain the maximum effect without the side effect, and this dosage may be easily determined by an expert in the field.

The dosage of the pharmaceutical composition of the present invention is not specifically limited, but is changed according to various factors including a health state and weight, severity of the disease of a patient, and a drug type, an administration route, and administration time. The composition may be administered in routes that are typically allowed in mammals including rat, mouse, cattle, human, etc., for example, orally, rectally, intravenously, subcutaneously, intrauterinely or intracerebrovascularly in a single dose amount or multidose per day.

In another aspect, the present invention relates to a pharmaceutical composition for preventing or treating cancer containing the antibody or antigen-binding fragment thereof as an active ingredient.

In another aspect, the present invention relates to a method for inhibiting tumor growth and treating cancer in a patient, comprising administering to the patient a pharmaceutical composition comprising the antibody or antigen-binding fragment described above. The method may further include administering a small molecule inhibitor used in chemotherapy or a vascular endothelial growth factor (VEGF) antagonist simultaneously or step-wise with the administration of the inventive antibody or fragment thereof. The VEGF antagonist may be an anti-VEGF antibody, a VEGF inhibiting fusion protein, or a small molecule kinase inhibitor.

As herein used, the term "cancer" or "tumor" typically refers to or describes a physiological condition of mammals characterized by cell growth/proliferation that is not controlled.

The cancer that can be treated with the composition of the present invention is not particularly limited, and includes both solid cancer and blood cancer. Examples of such cancers include squamous cell carcinoma, small cell lung cancer, non-small cell lung cancer, adenocarcinoma of the lung, squamous cell carcinoma of the lung, peritoneal cancer, skin cancer, skin or intraocular melanoma, rectal cancer, anal cancer, esophageal cancer, small intestine cancer, endocrine cancer, parathyroid cancer, adrenal cancer, soft tissue sarcoma, urethral cancer, chronic or acute leukemia, lymphoma, hepatocellular carcinoma, gastrointestinal cancer, pancreatic cancer, glioma, cervical cancer, ovarian cancer, liver cancer, bladder cancer, liver tumors, breast cancer, colon cancer, endometrial or uterine cancer, salivary gland cancer, kidney cancer, prostate cancer, vulva cancer, thyroid cancer, head and neck cancer, brain cancer, osteosarcoma and the like, but are not limited to.

The composition for preventing or treating cancer comprises the anti-Ang2 antibody and the constitution thereof is the same as the composition included in the composition for preventing or treating eye disease, so the description of each constitution applies equally to a composition for preventing or treating cancer.

Present application also contemplates using anti-Ang2 antibodies described herein in conjunction with chemo- or radiotherapeutic intervention, or other treatments. It also may prove effective, in particular, to combine anti-Ang2 antibodies with other therapies that target different aspects of Ang2 function.

In another embodiment, the inventive antibodies may be linked to at least one agent to form an antibody conjugate in order to increase the efficacy of antibody molecules as diagnostic or therapeutic agents.

In another aspect of the present invention, the present invention relates to a nucleic acid encoding the antibody or antigen-binding fragment thereof.

The nucleic acid used herein may be present in a cell, a cell lysate, or may also be present in a partially purified form or a substantially pure form. The nucleic acid is "isolated" or "is substantially pure" when it is purified from other cell components or other contaminants, for example, other cell nucleic acid or protein by standard techniques including alkaline/SDS treatment, CsCl banding, column chromatography, agarose gel electrophoresis, and other techniques well-known in the art. The nucleic acid of the present invention may be, for example, DNA or RNA, and may include an intron sequence, or may not include the intron sequence.

In still another aspect of the present invention, the present invention relates to a recombinant expression vector including the nucleic acid.

For expression of the antibody or fragments thereof, DNA encoding the light chain and the heavy chain having a partial length or a full length may be obtained by standard molecular biology techniques (for example, PCR amplification or cDNA cloning using a hybridoma that expresses a target antibody), and the DNA may be "operably bound" to transcription and translation control sequences to be inserted into the expression vector.

Term "operably bound" used herein may indicate that an antibody gene is ligated into the vector so that the transcription and translation control sequences in the vector have an intended function to control transcription and translation of the antibody gene. The expression vector and an expression control sequence are selected so as to have compatibility with a host cell for expression to be used. The light chain gene of the antibody and the heavy chain gene of the antibody are inserted into a separate vector, or both genes are inserted into the same expression vector. The antibody is inserted into the expression vector by a standard method (for example, ligation of an antibody gene fragment and a complementary restriction enzyme site on a vector or when the restriction enzyme site is not present at all, blunt end ligation). In some cases, the recombinant expression vector may encode a signal peptide that facilitates secretion of the antibody chain from the host cell. The antibody chain gene may be cloned into the vector so that the signal peptide is bound to an amino terminal of the antibody chain genes according to a frame. The signal peptide may be an immunoglobulin signal peptide or a heterologous signal peptide (i.e. signal peptide derived from proteins except for immunoglobulin). In addition, the recombinant expression vector has a regulatory sequence that controls the expression of the antibody chain genes in the host cell. The "regulatory sequence" may include a promoter, an enhancer and other expression control element (for example, polyadenylation signal) controlling the transcription or translation of the antibody chain gene. Those skilled in the art is able to recognize that design of the expression vector may vary by changing the regulatory sequences according to factors such as selection of the host cell to be transformed, an expression level of the protein, etc.

In still another aspect, the present invention relates to a cell transformed with the recombinant expression vector.

The cell used to produce the antibody of the present disclosure may be a prokaryote, yeast or higher eukaryotic cell, but is not limited thereto.

In particular, strains of the genus *Bacillus* such as *Escherichia coli, Bacillus subtilis* and *Bacillus tuligensis, Streptomyces, Pseudomonas* (for example, *Pseudomonas putida*), and prokaryotic host cells such as *Proteus mirabilis* and *Staphylococcus* (for example, *Staphylococcus carnosus*) can be used.

The interest in animal cells is the largest and examples of useful host cell lines include, but are not limited to, COS-7, BHK, CHO, CHOK1, DXB-11, DG-44, CHO/–DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, or HT1080.

The nucleic acid or the vector is transfected into the host cell. For the "transfection", various kinds of generally used techniques such as electrophoresis, calcium phosphate precipitation, DEAE-dextran transfection, lipofection, etc., may be used to introduce an exogenous nucleic acid (DNA or RNA) into a prokaryotic host cell or an eukaryotic host cell. The antibody according to the present invention may be expressed in an eukaryotic cell, preferably, in a mammalian host cell, in consideration of applicability into a mammalian cell. The mammalian host cells suitable for expression of the antibody may include a Chinese hamster ovary (CHO) cell (for example, including a dhfr– CHO cell used together with a DHFR selection marker), an NSO myeloma cell, a COS cell, or a SP2 cell, etc., as examples.

In another aspect, the present invention relates to a method for producing the anti-Ang2 antibody or antigen-binding fragment thereof, including culturing the host cells and expressing the antibody or antigen-binding fragment thereof.

When the recombinant expression vector encoding the antibody gene is introduced into the mammalian host cell, the antibody may be produced by culturing the host cell for a sufficient period of time so that the antibody is expressed in the host cell, or more preferably, for a sufficient period of time so that the antibody is secreted into a culture medium in which the host cell is cultured.

In some cases, the expressed antibody may be separated from the host cell and purified for uniformity. The separation or the purification of the antibody may be performed by a separation method, a purification method generally used for protein, for example, chromatography. The chromatography may include, for example, affinity chromatography, ion exchange chromatography or hydrophobic chromatography including protein A column and protein G column. In addition to the chromatography, the antibody may be separated and purified by additionally combining with filtration, ultrafiltration, salting out, dialysis, etc.

EXAMPLES

Hereinafter, the present invention will be described in more detail with reference to the following Examples. However, the following examples are only for exemplifying the present invention and it will be obvious to those skilled in the art that the scope of the present invention is not construed to be limited to these examples.

Example 1: Preparation of Mouse Monoclonal Anti-Ang2 Antibody 1-1: Mouse Immunization with Human Ang2

To be used as an antigen, the receptor binding domain (RBD) of human Ang2 (hAng2, SEQ ID NO: 2) was cloned into a vector containing CMV promotor and transiently expressed by transfecting into HEK293F cell line. After 5 days of incubation, the expressed recombinant human Ang2-RBD was purified by affinity column. Five-week-old BALB/c mice were immunized with purified human Ang2-RBD (100 µg/injection) mixed with an adjuvant twice weekly for 6 weeks. Anti-Ang2 antibody titers in the sera of immunized mice were examined by hAng2 ELISA. When the antibody titer (1:5,000 dilution) suitably increased (OD>1.0), the spleens were extracted from the immunized mice, and B lymphocytes were isolated therefrom and fused with cultured myeloma cells (SP2/0). The fused cells were cultured in a HAT medium containing hypoxanthine, aminopterin and thymidine, and hybridoma cells comprised only of a fusion of myeloma cells and B lymphocytes were selected therefrom and cultured. Survived hydridoma cells were seeded in 96-well plates and the culture supernatants were tested by hAng2 ELISA. Hybridoma pools showing a positive signal were selected for clonal selection through limiting dilution. Finally, about 50 monoclonal hybridoma lines were established. Among them, several Ang2-binding antibodies showed Tie2-activating activity. Candidate antibodies were selected based on Tie2 activating level and high affinity to human Ang2, later processed for humanization.

TABLE 1

Human Angiopoietin-2 full-length (hAng2) and receptor-binding domain (RBD) sequences Human Angiopoietin-2 full-length (SEQ ID NO: 1)

| | |
|---|---|
| MWQIVFFTLSCDLVLAAAYNNFRKSMDSIGKKQYQVQHGSCSYTFLL | 50 |
| PEMDNCRSSSSPYVSNAVQRDAPLEYDDSVQRLQVLENIMENNTQWL | 100 |
| MKLENYIQDNMKKEMVEIQQNAVQNQTAVMIEIGTNLLNQTAEQTRK | 150 |
| LTDVEAQVLNQTTRLELQLLEHSLSTNKLEKQILDQTSEINKLQDKN | 200 |
| SFLEKKVLAMEDKHIIQLQSIKEEKDQLQVLVSKQNSIIEELEKKIV | 250 |
| TATVNNSVLQKQQHDLMETVNNLLTMMSTSNSAKDPTVAKEEQISFR | 300 |
| DCAEVFKSGHTTNGIYTLTFPNSTEEIKAYCDMEAGGGGWTIIQRRE | 350 |
| DGSVDFQRTWKEYKVGFGNPSGEYWLGNEFVSQLTNQQRYVLKIHLK | 400 |
| DWEGNEAYSLYEHFYLSSEELNYRIHLKGLTGTAGKISSISQPGNDF | 450 |
| STKDGDNDKCICKCSQMLTGGWWFDACGPSNLNGMYYPQRQNTNKFN | 496 |
| GIKWYYWKGSGYSLKATTMMIRPADF | |

Human Angiopoietin-2 receptor-binding domain (RBD) (SEQ ID NO: 2)

| | |
|---|---|
| EEQISFRDCAEVFKSGHTTNGIYTLTFPNSTEEIKAYCDMEAGGGGV | 50 |
| VTIIQRREDGSVDFQRTWKEYKVGFGNPSGEYWLGNEFVSQLTNQQR | 100 |
| YVLKIHLKDWEGNEAYSLYEHFYLSSEELNYRIHLKGLTGTAGKISS | 150 |
| ISQPGNDFSTKDGDNDKCICKCSQMLTGGVWVFDACGPSNLNGMYYP | 200 |
| QRQNTNKFNGIKVVYYWKGSGYSLKATTMMIRPADF | 221 |

1-2: Production and Purification of Mouse Monoclonal Anti-Ang2 Antibodies

In order to produce the anti-Ang2 antibody selected based on the ELISA positive reaction, hybridoma cells were cultured in 10% FBS-containing DMEM (Dulbecco's Modified Eagle's Medium) in a T75 (75 cm² area) flask. When the confluency of the cells reached about 90%, the cells were washed with PBS, incubated with 50 ml of serum-free medium (SFM, Gibco) and cultured at 37° C. for 3 days. Then, the culture medium in which the antibody was secreted from each monoclonal hybridoma was collected, centrifuged to remove the cells, and the culture supernatant was collected and filtered. The antibody was then purified using an AKTA purification device (GE Healthcare) equipped with a Protein G affinity column (GE Healthcare). The purified antibody was concentrated by substituting the supernatant with PBS using a centrifugal filter unit (Amicon).

1-3: Identification and Screening of Tie2 Receptor Activating Anti-Ang2 Antibodies To investigate whether the mouse anti-Ang2 antibodies induce the downstream signaling of the Tie2 receptor in endothelial cells, HUVECs (Lonza) were treated with a combination of hAng2 protein and anti-Ang2 antibody, and then the level of Akt phosphorylation, the main downstream signaling protein of Tie2 receptor, was analyzed by immunoblotting. As a negative control group, the full-length hAng2 (R & D systems) alone was treated into the cells.

Specifically, HUVECs (1×10⁵ cells/ml) were cultured in EGM-2 medium (Lonza) at 37° C. in a 60 mm culture dish. Cells (90% confluency) were incubated with serum-free EBM-2 medium for 4 hrs for serum starvation. The serum-starved HUVECs were treated with a mixture of anti-Ang2 antibody and hAng2 protein (1 μg/ml, R&D system) and further incubated for 30 min. The cells were washed with cold PBS, treated with lysis buffer, and lysed at 4° C. for 20 min. Then, the cell lysates were prepared by centrifugation at 13000 rpm for 15 min. 5×SDS sample buffer was added to the cell lysate and the cell lysate was boiled at 95° C. for 5 min. Then, the cell lysate was subjected to SDS PAGE and proteins were transferred to a nitrocellulose membrane (GE).

To investigate Akt phosphorylation, the blot was blocked with 5% skim milk-containing TBS-T for 1 hr at room temperature (RT), and incubated with anti-phospho-Akt antibody (S473) at 4° C. for about 8 hrs. The amount of phospho-Akt was visualized by an enhanced chemiluminescence (ECL). Then, the membrane was incubated in a stripping buffer (Thermo) for 15 min, and then reprobed with an anti-Akt antibody to determine the amount of total Akt.

Akt phosphorylation at S473 was strongly induced in several groups treated with a combination of hAng2 and anti-Ang2 antibody such as 2C8, 4B9, 2F10 and 4E2, respectively (FIG. 1).

1-4: Affinity Measurement of Anti-Ang2 Antibodies Against hAng2 by Octet Analysis The affinity of mouse monoclonal antibody against hAng2 was measured using Octet system (ForteBio). Specifically, buffer and samples were measured in total 200 μl/well using Black 96-well plates (96 well F-type black plates, Greiner). The biosensor used for affinity measurements was hydrated for 10 min before measurement with AR2G tip (ForteBio Octet). After the hydration, hAng2 was diluted in 10 mM sodium acetate, pH 6.0 buffer at a concentration of 10 μg/ml, fixed on AR2G biosensor, and blocked with 1M ethanolamine. The mouse monoclonal anti-Ang2 antibodies were diluted to 50, 25, 12.5, 6.25, 3.125, and 0 nM with 1× kinetic buffer, and subjected to association for 300 seconds and dissociation for 900 seconds. For affinity measurement ($K_D$), the association rate (K-on) and dissociation rate (K-off) were analyzed by binding curve (global) and fitted to 1:1 binding model using Octet data analysis v9.0.0.10 program. The $K_D$ values were shown in the following Table 2. The affinities to hAng2 of mouse anti-Ang2 antibodies are shown in Table 2.

TABLE 2

Affinities to hAng2 of mouse anti-Ang2 antibodies

| Antibody | Kon (1/Ms) | Koff (1/s) | $K_D$ (M) |
|---|---|---|---|
| 2C8 | 7.78E+04 | 3.54E-06 | 4.55E-11 |
| 2F10 | 1.24E+05 | 1.71E-05 | 1.38E-10 |
| 4B9 | 1.37E+05 | 5.04E-07 | 3.68E-12 |
| 4E2 | 2.83E+04 | 1.34E-04 | 4.74E-09 |

Example 2: DNA Gene Sequence Analysis of Mouse Anti-Ang2 Antibodies

The DNA nucleotide sequence of the antibody (derived from hybridoma cells) selected in Example 1-3 was analyzed. Specifically, hybridoma cells (2×10⁶ cells/ml) were cultured in 10% FBS-containing DMEM and then total RNA was obtained using RNeasy mini kit (Qiagen). Next, RNA concentration was measured, and cDNA was synthesized through reverse transcription (RT) reaction. To amplify the heavy and light chain variable region gene sequences of the monoclonal antibodies produced in each hybridoma cell, PCR was carried out using Mouse Ig-Primer set (Novagen)

under the following conditions using above cDNA as a template: 94° C. 5 min; [1 min at 94° C., 1 min at 50° C., 2 min at 72° C.]×35 cycles; 6 min at 72° C., cooling to 4° C. The PCR product obtained from each reaction was cloned into a TA vector, and subjected to DNA sequencing, thereby obtaining the nucleotide sequences encoding the CDR, heavy-chain variable region and light-chain variable region of each antibody (Tables 3 to 10).

TABLE 3

CDR sequence of mouse anti-Ang2 antibody 4B9

| Antibody | CDR Sequence | | |
|---|---|---|---|
| 4B9 | Heavy Chain CDR Sequence | | |
| | CDRH1-KABAT | CDRH2-KABAT | CDRH3-KABAT |
| | DYYMY (SEQ ID NO: 3) | TISVGGSFTYY PDSVKG (SEQ ID NO: 4) | DWGLRPWFVY (SEQ ID NO: 5) |
| | Light Chain CDR Sequence | | |
| | CDRL1-KABAT | CDRL2-KABAT | CDRL3-KABAT |
| | KASQDVSTAVA (SEQ ID NO: 6) | WASTRHT (SEQ ID NO: 7) | QQHYSTPPT (SEQ ID NO: 8) |

TABLE 4

Variable region sequence of mouse anti-Ang2 antibody 4B9

Antibody Variable Region Sequence

4B9
Heavy Chain Variable Region Sequence

EVQLVESGGGLVKPGGSLKLSCAASGFTFSDYYMYVVVRQTPEK
RLEVVVATISVGGSFTYYPDSVKGRFTISRDNAKNNLYLQMSSL
KSEDTAMYYCARDWGLRPWFVYWGQGTLVTVSA (SEQ ID
NO: 9)

GAAGTGCAGCTGGTGGAGTCTGGGGGAGGCTTAGTGAAGCCTGG
AGGGTCCCTGAAACTCTCCTGTGCAGCCTCTGGATTCACTTTCA
GTGACTATTACATGTATTGGGTTCGCCAGACTCCGGAAAAGAGG
CTGGAGTGGGTCGCAACCATTAGTGTTGGTGGTAGTTTCACCTA
CTATCCAGACAGTGTGAAGGGGCGATTCACCATCTCCAGAGACA
ATGCCAAGAACAACCTGTACCTGCAAATGAGCAGTCTGAAGTCT
GAGGACACAGCCATGTATTACTGTGCAAGAGACTGGGGATTACG
ACCCTGGTTTGTTTACTGGGGCCAAGGGACTCTGGTCACTGTCT
CTGCA (SEQ ID NO: 10)

Light Chain Variable Region Sequence

DIVMTQSHKFMSTSVGDRVSITCKASQDVSTAVAVVYQQKPGQS
PKLLIYWASTRHTGVPDRFTGSGSGTDYTLTISSVQAEDLALYY
CQQHYSTPPTFGSGTKLEIK (SEQ ID NO: 11)

GACATTGTGATGACCCAGTCTCACAAATTCATGTCCACATCAGT
AGGAGACAGGGTCAGCATCACCTGCAAGGCCAGTCAGGATGTGA
GTACTGCTGTAGCCTGGTATCAACAAAAACCAGGGCAATCTCCT
AAACTACTGATTTACTGGGCATCCACCCGGCACACTGGAGTCCC
TGATCGCTTCACAGGCAGTGGATCTGGGACAGATTATACTCTCA
CCATCAGCAGTGTGCAGGCTGAAGACCTGGCACTTTATTACTGT
CAGCAACATTATAGCACTCCTCCCACGTTCGGCTCGGGGACAAA
GTTGGAAATAAAA (SEQ ID NO: 12)

TABLE 5

CDR sequence of mouse anti-Ang2 antibody 2C8

| Antibody | CDR Sequence | | |
|---|---|---|---|
| 2C8 | Heavy Chain CDR Sequence | | |
| | CDRH1-KABAT | CDRH2-KABAT | CDRH3-KABAT |
| | SYWMH (SEQ ID NO: 13) | MIDPSDSETRL NQKFKD (SEQ ID NO: 14) | RFYYGSDVVYF DV (SEQ ID NO: 15) |
| | Light Chain CDR Sequence | | |
| | CDRL1-KABAT | CDRL2-KABAT | CDRL3-KABAT |
| | KASQDVGTAVA (SEQ ID NO: 16) | WASTRHT (SEQ ID NO: 17) | QQYSSYPLT (SEQ ID NO: 18) |

TABLE 6

Variable region sequence of mouse anti-Ang2 antibody 2C8

Antibody Variable Region Sequence

2C8
Heavy Chain Variable Region Sequence

QVQLQQSGPQLVRPGASVKISCKASGYSFTSYWMHVVVKQRPGQ
GLEWIGMIDPSDSETRLNQKFKDKASLTVDKSSSTAYMQLSSPT
SGDSAVYYCARRFYYGSDWYFDVWGAGSTVTVSS (SEQ ID
NO: 19)

CAGGTGCAACTGCAGCAGTCTGGGCCTCAGCTGGTTAGGCCTGG
GGCTTCAGTGAAGATATCCTGCAAGGCTTCTGGTTACTCATTCA
CCAGCTACTGGATGCACTGGGTGAAGCAGAGGCCTGGACAAGGT
CTTGAGTGGATTGGCATGATTGATCCTTCCGATAGTGAAACTAG
GTTAAATCAGAAGTTCAAGGACAAGGCCTCATTGACTGTAGACA
AATCCTCCAGCACAGCCTACATGCAACTCAGCAGCCCGACATCT
GGGGACTCTGCGGTCTATTACTGTGCAAGACGTTTTTACTACGG
GTCGGACTGGTACTTCGATGTCTGGGGCGCAGGGTCCACGGTCA
CCGTCTCCTCA (SEQ ID NO: 20)

Light Chain Variable Region Sequence

DIVMTQSHKFMSTSVGDRVSITCKASQDVGTAVAVVYQQKPGQS
PKLLIYWASTRHTGVPDRFTGSGSGTDFTLTISNVQSEDLADYF
CQQYSSYPLTFGSGTKLEIK (SEQ ID NO: 21)

GACATTGTGATGACCCAGTCTCACAAATTCATGTCCACATCAGT
AGGAGACAGGGTCAGCATCACCTGCAAGGCCAGTCAGGATGTGG
GTACTGCTGTAGCCTGGTATCAACAGAAACCAGGTCAATCTCCT
AAACTACTGATTTACTGGGCATCCACCCGGCACACTGGAGTCCC
TGATCGCTTCACAGGCAGTGGATCTGGGACAGATTTCACTCTCA
CCATTGACAATGTGCAGTCTGAAGACTTGGCAGATTATTTCTGT
CAGCAATATAGCAGCTATCCTCTCACGTTCGGCTCGGGGACAAA
GTTGGAAATAAAA (SEQ ID NO: 22)

TABLE 7

CDR sequence of mouse anti-Ang2 antibody 2F10

| Antibody | CDR Sequence | | |
|---|---|---|---|
| 2F10 | | | |
| | Heavy Chain CDR Sequence | | |
| | CDRH1-KABAT | CDRH2-KABAT | CDRH3-KABAT |
| | DYYMY (SEQ ID NO: 23) | TINDGGSYTYY PDSVKG (SEQ ID NO: 24) | DWGLRPWFVY (SEQ ID NO: 25) |
| | Light Chain CDR Sequence | | |
| | CDRL1-KABAT | CDRL2-KABAT | CDRL3-KABAT |
| | KASQDVSTAVA (SEQ ID NO: 26) | WASTRHT (SEQ ID NO: 27) | QQHYTTPPT (SEQ ID NO: 28) |

TABLE 8

Variable region sequence of mouse anti-Ang2 antibody 2F10

| Antibody | Variable Region Sequence |
|---|---|
| 2F10 | |
| | Heavy Chain Variable Region Sequence |
| | QVQLVESGGGLVKPGGSLKLSCAASGFTFSDYYMYWIRQ TPEKRLEVVVATINDGGSYTYYPDSVKGRFTISRDNAKN NLYLQMSSLKSEDTAMYYCARDWGLRPWFVYWGQGTLVT VSA (SEQ ID NO: 29) |
| | GAAGTGCAGCTGGTGGAGTCTGGGGGAGGCTTAGTGAAG CCTGGAGGGTCCCTGAAACTCTCCTGTGCAGCCTCTGGA TTCACTTTCAGTGACTATTACATGTATTGGATTCGCCAG ACTCCGGAAAAGAGGCTGGAGTGGGTCGCAACCATTAAT GATGGTGGTAGTTACACCTACTATCCAGACAGTGTGAAG GGGCGATTCACCATCTCCAGAGACAATGCCAAGAACAAC CTGTACCTGCAAATGAGCAGTCTGAAGTCTGAGGACACA GCCATGTATTACTGTGCAAGAGACTGGGGATTACGACCC TGGTTTGTTTACTGGGGCCAAGGGACTCTGGTCACTGTC TCTGCA (SEQ ID NO: 30) |
| | Light Chain Variable Region Sequence |
| | DIVMTQSHKFMSTSVGDRVSITCKASQDVSTAVAVVYQQ KPGQSPKLLIYWASTRHTGVPDRFTGSGSGTDYTLTISS VQAEDLALYYCQQHYTTPPTFGSGTKLEIK (SEQ ID NO: 31) |
| | GACATTGTGATGACCCAGTCTCACAAATTCATGTCCACA TCAGTAGGAGACAGGGTCAGCATCACCTGCAAGGCCAGT CAGGATGTGAGTACTGCTGTAGCCTGGTATCAACAAAAA CCAGGGCAATCTCCTAAACTACTGATTTACTGGGCATCC ACCCGGCACACTGGAGTCCCTGATCGCTTCACAGGCAGT GGATCTGGGACAGATTATACTCTCACCATCAGCAGTGTG CAGGCTGAAGACCTGGCACTTTATTACTGTCAGCAACAT TATACCACTCCTCCCACGTTCGGCTCGGGGACAAAGTTG GAAATAAAA (SEQ ID NO: 32) |

TABLE 9

CDR sequence of mouse anti-Ang2 antibody 4E2

| Antibody | CDR Sequence | | |
|---|---|---|---|
| 4E2 | | | |
| | Heavy Chain CDR Sequence | | |
| | CDRH1-KABAT | CDRH2-KABAT | CDRH3-KABAT |
| | GYNMN (SEQ ID NO: 33) | NIDPYYGGTSY NQKFKG (SEQ ID NO: 34) | YGNYVDY (SEQ ID NO: 35) |
| | Light Chain CDR Sequence | | |
| | CDRL1-KABAT | CDRL2-KABAT | CDRL3-KABAT |
| | KASQDVSTAVA (SEQ ID NO: 36) | WASTRHT (SEQ ID NO: 37) | QQHYNTPPT (SEQ ID NO: 38) |

TABLE 10

Variable region sequence of mouse anti-Ang2 antibody 4E2

| Antibody | Variable Region Sequence |
|---|---|
| 4E2 | |
| | Heavy Chain Variable Region Sequence |
| | EVQLQQSGPELEKPGASVKISCKASGYSFTGYNMNVVVK QSNGKSLEWIGNIDPYYGGTSYNQKFKGKATLTVDKSSS TAYMQLKSLTSEDSAVYYCVRYGNYVDYWGQGTTLTVSS (SEQ ID NO: 39) |
| | CAGCTGCAGCAGTCTGGACCTGAGCTGGAGAAGCCTGGC GCTTCAGTGAAGATATCCTGCAAGGCTTCTGGTTACTCA TTCACTGGCTACAACATGAACTGGGTGAAGCAGAGCAAT GGAAAGAGCCTTGAGTGGATTGGAAATATTGATCCTTAC TATGGTGGTACTAGCTACAACCAGAAGTTCAAGGGCAAG GCCACATTGACTGTAGACAAATCCTCCAGCACAGCCTAC ATGCAGCTCAAGAGCCTGACATCTGAGGACTCTGCAGTC TATTACTGTGTAAGGTATGGTAACTACGTGGACTACTGG GGCCAAGGCACCACTCTCACAGTCTCCTCA (SEQ ID NO: 40) |
| | Light Chain Variable Region Sequence |
| | DIVMTQSHKFMSTSVGDRVSITCKASQDVSTAVAVVYQQ KPGQSPKLLIYWASTRHTGVPDRFTGSGSGTDYTLTISS VQAEDLALYYCQQHYNTPPTFGSGTKLEIK (SEQ ID NO: 41) |
| | GACATTGTGATGACCCAGTCCCACAAATTCATGTCCACA TCAGTAGGAGACAGGGTCAGCATCACCTGCAAGGCCAGT CAGGATGTGAGTACTGCTGTAGCCTGGTATCAACAAAAA CCAGGGCAATCTCCTAAACTACTGATTTACTGGGCATCC ACCCGGCACACTGGAGTCCCTGATCGCTTCACAGGCAGT GGATCTGGGACAGATTATACTCTCACCATCAGCAGTGTG CAGGCTGAAGACCTGGCACTTTATTACTGTCAGCAACAT TATAACACTCCTCCCACGTTCGGCTCGGGGACAAAGTTG GAAATAAAA (SEQ ID NO: 42) |

Example 3: Epitope Mapping of Mouse Anti-Ang2 Antibody Against hAng2

The antigenic determinants (epitopes) of hAng2 recognized by mouse monoclonal antibodies, 2C8 and 4B9, were analyzed by HDX-MS (Hydrogen/deuterium exchange-mass spectrometry) technique. HDX-MS analysis methods are described in the following articles; Houde D, Engen J R (2013) Methods Mol. Biol. 988: 269-89 and Houde et al. (2011) J. Pharm. Sci. 100 (6), 2071.

Recombinant hAng2-RBD protein was used to analyze the epitopes of antibodies 2C8 and 4B9. Before deuterium labeling reaction, hAng2-RBD/antibody mixtures were incubated for more than 3 hrs to be maintained to the maximum binding (100%) under 15× diluted deuterium labeling buffer ($K_D$=25 nM). The prepared hAng2-RBD/antibody complexes were diluted 15 times with deuterium labeling buffer, labeled at various time, and then quenched with the same volume of quenching buffer. The labeling reaction time was 0 min (undeuterium), 0.33 min, 10 min, 60 min and 240 min. However, in undeuterium condition, the deuterium labeling buffer was replaced with equilibrium buffer and the reaction was immediately stopped with quenching buffer. For mass sprectrometry, the deuterium labeled hAng2-RBD/antibody samples were loaded on a pepsin column and peptide digestion was proceeded. Mass spectrometry analysis showed that 13 peptides at the N-terminal of hAng2-RBD and peptic peptides corresponding to 25-40 amino acids were not detected at all, and 83.7% coverage data was obtained from a total of 45 peptic peptides.

The deuterium uptake difference between hAng2-RBD alone and the hAng2-RBD-antibody complex conditions was comparatively analyzed, and a region showing a distinct decrease in the deuterium uptake is either a peptide to which the antibody binds directly, or a structurally changed region. When the deuterium uptake difference between hAng2-RBD alone and the hAng2-RBD-antibody complex was 0.5-1 Da or more, it was considered significant.

Figure 2:
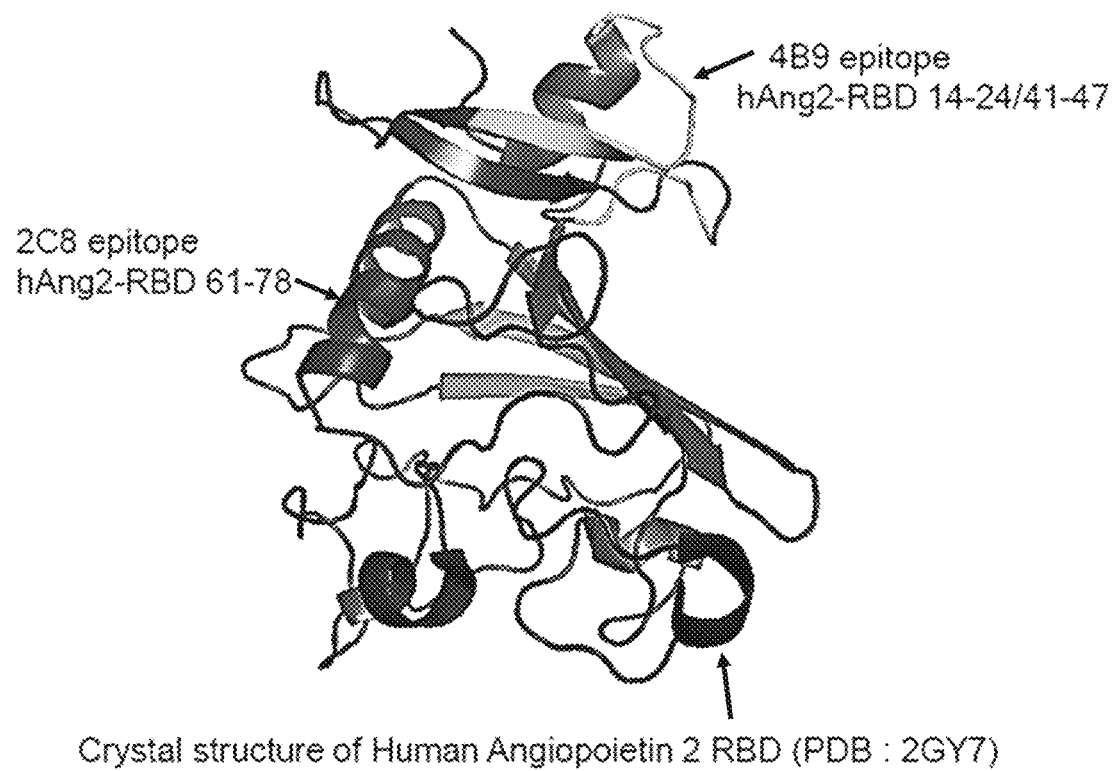
FIG. 2. Schematic showing epitopes of anti-Ang2 antibodies, which were analyzed by hydrogen/deuterium exchange-mass spectrometry. Recombinant hAng2-RBD alone or hAng2-RBD/Ang2-antibody complex was labeled with deuterium. The labeled proteins were digested in pepsin column and were analyzed by mass spectrometry. The deuterium uptake of hAng2-RBD alone and hAng2-RBD/Ang-2 antibody complex was analyzed and the difference in deuterium uptake was compared. A peptide with mass difference over 0.5-1 Da in deuterium uptake was determined to be a specific epitope which mediate the binding to anti-Ang2 antibodies. 2C8 epitope and 4B9 epitope were visualized in the image of Ang2-RBD crystal structure (PDB:2GY7) which was generated using PyMol software.

Analysis of the deuterium uptake difference indicated that the epitope to which antibody 2C8 binds is residues 61 to 78 of SEQ ID NO: 2—QRTWKEYKVGFGNPSGEY (SEQ ID NO: 115) of hAng2-RBD (Table 11), and the epitope to which antibody 4B9 binds is residues 14 to 24 of SEQ ID NO: 2 —KSGHTTNGIYT (SEQ ID NO: 116) and residues 41 to 47 of SEQ ID NO: 2 —EAGGGGW (SEQ ID NO: 117) (Table 12). In the case of antibody 4B9, it cannot be ruled out that an undetermined region (residues 25 to 40 of SEQ ID NO: 2) can be included in the scope of the epitope. The epitope analysis results for each antibody are shown in different colors on the 3D structure of hAng2-RBD, which was generated using PyMol software (FIG. 2).

TABLE 11

Epitope mapping analysis for 2C8 binding to hAng2 by HDX-MS
2C8 binding to hAng2-RBD

| Residues (SEQ ID NO: 2) | Exposure Time (min) | Relative Uptake (Da) hAng2-RBD alone | hAng2-RBD + 2C8 | Δ |
|---|---|---|---|---|
| 52-60 | 0.00 | 0.79 | 0.64 | 0.15 |
| 52-60 | 0.33 | 1.36 | 1.14 | 0.21 |
| 52-60 | 10.00 | 1.92 | 1.51 | 0.41 |
| 52-60 | 60.00 | 2.10 | 1.96 | 0.14 |
| 52-60 | 240.00 | 2.35 | 2.28 | 0.08 |
| 61-77 | 0.00 | 1.23 | 1.15 | 0.08 |
| 61-77* | 0.33 | 2.93 | 1.75 | 1.18 |
| 61-77* | 10.00 | 4.71 | 2.93 | 1.78 |
| 61-77* | 60.00 | 5.16 | 3.80 | 1.36 |
| 61-77* | 240.00 | 5.53 | 4.22 | 1.31 |
| 61-78 | 0.00 | 1.27 | 1.21 | 0.06 |
| 61-78* | 0.33 | 3.01 | 1.87 | 1.15 |
| 61-78* | 10.00 | 4.77 | 2.97 | 1.80 |
| 61-78* | 60.00 | 5.22 | 3.90 | 1.33 |
| 61-78* | 240.00 | 5.59 | 4.25 | 1.34 |
| 67-77 | 0.00 | 0.85 | 0.96 | −0.12 |
| 67-77* | 0.33 | 2.13 | 1.24 | 0.89 |
| 67-77* | 10.00 | 3.09 | 1.51 | 1.58 |
| 67-77* | 60.00 | 3.26 | 2.05 | 1.21 |
| 67-77* | 240.00 | 3.53 | 2.46 | 1.07 |
| 67-78 | 0.00 | 1.12 | 0.82 | 0.30 |
| 67-78* | 0.33 | 2.39 | 1.44 | 0.95 |
| 67-78* | 10.00 | 3.30 | 1.64 | 1.66 |
| 67-78* | 60.00 | 3.48 | 2.15 | 1.33 |
| 67-78* | 240.00 | 3.72 | 2.68 | 1.04 |
| 78-84 | 0.00 | 0.59 | 0.59 | 0.00 |
| 78-84 | 0.33 | 0.69 | 0.70 | −0.01 |
| 78-84 | 10.00 | 0.71 | 0.69 | 0.01 |
| 78-84 | 60.00 | 0.83 | 0.73 | 0.11 |
| 78-84 | 240.00 | 1.07 | 0.72 | 0.36 |

TABLE 12

Epitope mapping analysis for 4139 binding to hAng2 by HDX-MS
4B9 binding to hAng2-RBD

| Residues (SEQ ID NO: 2) | Exposure Time (min) | Relative Uptake (Da) hAng2-RBD alone | hAng2-RBD + 4B9 | Δ |
|---|---|---|---|---|
| 14-23 | 0.00 | 0.80 | 0.55 | 0.25 |
| 14-23* | 0.33 | 1.31 | 0.97 | 0.34 |
| 14-23* | 10.00 | 2.21 | 1.38 | 0.83 |
| 14-23* | 60.00 | 2.27 | 1.49 | 0.78 |
| 14-23* | 240.00 | 2.26 | 1.66 | 0.60 |
| 14-24 | 0.00 | 0.77 | 0.76 | 0.01 |
| 14-24* | 0.33 | 1.59 | 1.27 | 0.33 |
| 14-24* | 10.00 | 3.25 | 1.75 | 1.50 |
| 14-24* | 60.00 | 3.40 | 2.05 | 1.35 |
| 14-24* | 240.00 | 3.41 | 2.61 | 0.80 |
| 41-47 | 0.00 | 0.30 | 0.16 | 0.15 |
| 41-47* | 0.33 | 1.22 | 0.20 | 1.02 |
| 41-47* | 10.00 | 1.35 | 0.43 | 0.92 |
| 41-47* | 60.00 | 1.69 | 0.54 | 1.15 |
| 41-47* | 240.00 | 1.80 | 0.61 | 1.18 |
| 47-60 | 0.00 | 1.01 | 0.96 | 0.05 |
| 47-60 | 0.33 | 1.81 | 1.94 | −0.13 |
| 47-60 | 10.00 | 2.47 | 2.53 | −0.06 |
| 47-60 | 60.00 | 2.68 | 2.69 | −0.01 |
| 47-60 | 240.00 | 2.95 | 3.06 | −0.11 |

Example 4: Humanization of Mouse Anti-Ang2 Antibody and Full-Length Igg Conversion To eliminate the immunogenicity of mouse anti-Ang2 antibodies 2C8 and 4B9 when administered into human, the antibodies were humanized as follows.

4-1: Heavy Chain Humanization

The human antibody heavy chain variable gene showing 64% homology to the heavy chain sequence of antibody 2C8 was IGHV1-46-01. Based on these analysis, the CDR region of the 2C8 antibody was transplanted into the human antibody heavy chain variable gene IGHV1-46-01. In this process, 5 humanized heavy chain antibody genes were designed (Table 13). Back mutations to mouse sequence were introduced in heavy chain genes of humanized 2C8, indicated as bold in protein sequence of Table 13.

The human antibody heavy chain variable gene showing 80% homology to the heavy chain sequence of antibody 4B9 was IGHV3-11-01. Based on the analysis, the CDR region of the 4B9 antibody was transplanted into the human antibody heavy chain variable gene IGHV3-11-01. As the result, 3 humanized heavy chain antibody genes were designed in this process (Table 13). Back mutations to mouse sequence were introduced in heavy chain genes of humanized 4B9, indicated as bold in protein sequence of Table 13.

4-2: Light Chain Humanization

The human antibody light chain variable gene showing homology of 67% to the light chain sequence of antibody 2C8 was IGKV1-9-01. Based on these analyses, the CDR region of 2C8 antibody was transplanted into the human antibody light chain variable gene IGKV1-9-01. 3 humanized light chain antibody genes were designed in this process (Table 13). Back mutations to mouse sequence were introduced in light chain genes of humanized 2C8, indicated as bold in protein sequence of Table 13.

The human antibody light chain variable gene showing 70% homology to the light chain sequence of antibody 4B9 was IGKV1-39-01. Based on these analyses, the CDR region of 4B9 antibody was transplanted into the human antibody light chain variable gene IGKV1-39-01. 1 humanized light chain antibody gene was designed in this process (Table 13).

4-3: Humanized Gene Synthesis and Cloning to Human Full-Length IgG Antibody

The humanized variable regions of antibodies in Table 15 were incorporated into the heavy chain and the light chain vector of the human IgG1 antibody. Coding nucleotides corresponding to the humanized heavy chain variable region of the antibodies (VH) were synthesized by Bioneer, Inc. so as to consist of 'EcoRI-signal sequence-VH-NheI-CH-XhoI'. Coding nucleotides corresponding the humanized light chain variable region of the antibodies (VL) were synthesized by Bioneer, Inc. so as to consist of 'EcoRI-signal sequence-VL-BsiWI-CL-XhoI'. The polynucleotides encoding the heavy chain were respectively cloned into a vector of pOptiVEC™-TOPO TA Cloning Kit included in OptiCHO™ Antibody Express Kit (Invitrogen), and the polynucleotides encoding the light chain were respectively cloned into a vector of pcDNA™3.3-TOPO TA Cloning Kit (Invitrogen), using EcoRI and XhoI to establish vectors for expressing full-length human IgG antibodies. For construction of human IgG4 class antibody of 2C8H11 and 4B9H11, each named 2C8H11G4 and 4B9H11G4, the constant regions (CH1-hinge-CH2-CH3) of 2C8H11 heavy chain gene and 4B9 heavy chain gene were replaced by the polynucleotide encoding IgG4 class heavy chain constant region.

TABLE 13

Humanized anti-Ang2 antibodies originated from mouse 4B9 and 2C8 antibodies

| Antibody | Antibody Sequence (VH) | Antibody Sequence (VL) |
|---|---|---|
| 4B9H11 | (Protein Sequence)<br>QVQLVESGGGLVKPGGSLR<br>SLCAASGFTFSDYYMYWIR<br>QAPGKGLEWVSTISVGGSF<br>TYYPDSVKGRFTISRDNAK<br>NSLYLQMNSLRAEDTAVYY<br>CARDWGLRPWFVYWGQGTL<br>VTVSS (SEQ ID NO: 43) | (Protein Sequence)<br>DIQMTQSPSSLSASVGDRVT<br>ITCKASQDVSTAVAWYQQKP<br>GKAPKLLIYWASTRHTGVPS<br>RFSGSGSGTDFTLTISSLQP<br>EDFATYYCQQHYSTPPTFGQ<br>GTKVEIK (SEQ ID NO: 44) |
| | (Coding Nucleotide Sequence)<br>CAGGTACAGCTCGTGGAGT<br>CTGGTGGAGGCTTGGTGAA<br>ACCTGGAGGGTCCCTGAGA<br>CTTAGCTGTGCAGCTTCCG<br>GCTTCACATTTTCAGACTA<br>TTATATGTATTGGATCAGA<br>CAGGCTCCCGGGAAGGGCT<br>TGGAGTGGGTTTCAACCAT<br>TAGTGTTGGCGGATCTTTT<br>ACTTACTACCCAGACAGTG<br>TGAAGGGGAGATTCACAAT<br>CTCCAGGGATAACGCGAAA<br>AACAGCCTGTATCTCCAAA<br>TGAATAGCCTGAGAGCCGA<br>AGATACCGCCGTGTACTAC<br>TGCGCCAGAGACTGGGGAT<br>TACGGCCCTGGTTCGTGTA<br>CTGGGGCCAGGGAACCCTG<br>GTCACCGTCTCCTCA<br>(SEQ ID NO: 45) | (Coding Nucleotide Sequence)<br>GACATCCAGATGACACAGTC<br>CCCAAGCTCCCTGTCTGCAT<br>CTGTGGGAGACCGGGTGACC<br>ATCACTTGTAAGGCCTCACA<br>GGATGTTTCTACTGCTGTCG<br>CATGGTACCAGCAAAAGCCG<br>GGTAAAGCTCCCAAGCTTTT<br>GATATACTGGGCCAGCACCA<br>GGCACACAGGCGTGCCATCA<br>AGATTCAGTGGGTCCGGATC<br>CGGCACGGATTTTACACTCA<br>CTATTAGCTCACTGCAACCT<br>GAAGACTTTGCCACCTATTA<br>CTGCCAGCAGCATTATAGCA<br>CCCCTCCCACCTTCGGTCAG<br>GGCACTAAAGTAGAAATCAA<br>A (SEQ ID NO: 46) |
| 4B9H21 | (Protein Sequence)<br>QVQLVESGGGLVKPGGSLR<br>LSCAASGFTFSDYYMYWVR<br>QAPGKGLEWVSTISVGGSF<br>TYYPDSVKGRFTISRDNAK<br>NSLYLQMNSLRAEDTAVYY<br>CARDWGLRPWFVYWGQGTL<br>VTVSS (SEQ ID NO: 47) | (Protein Sequence)<br>DIQMTQSPSSLSASVGDRVT<br>ITCKASQDVSTAVAWYQQKP<br>GKAPKLLIYWASTRHTGVPS<br>RFSGSGSGTDFTLTISSLQP<br>EDFATYYCQQHYSTPPTFGQ<br>GTKVEIK (SEQ ID NO: 48) |
| | (Coding Nucleotide Sequence)<br>CAGGTCCAGCTGGTGGAAT<br>CCGGCGGAGGCTTGGTGAA<br>GCCTGGAGGCAGCCTAAGA<br>CTCTCCTGTGCAGCCTCTG<br>GCTTCACCTTCTCTGACTA<br>TTACATGTATTGGGTCCGC<br>CAGGCTCCAGGGAAAGGGC<br>TCGAGTGGGTTTCAACAAT<br>TAGTGTAGGTGGAAGCTTC<br>ACCTACTATCCTGACTCCG<br>TGAAAGGAAGATTTACGAT<br>CTCTAGGGATAATGCCAAG<br>AACTCACTGTACCTTCAGA<br>TGAACAGCCTGAGAGCGGA<br>GGACACAGCCGTGTACTAC<br>TGCGCTAGAGATTGGGGAT<br>TAAGACCCTGGTTTGTTTA<br>TTGGGGCCAGGGAACCCTG<br>GTCACCGTCTCCTCA<br>(SEQ ID NO: 49) | (Coding Nucleotide Sequence)<br>GACATCCAGATGACACAGTC<br>CCCAAGCTCCCTGTCTGCAT<br>CTGTGGGAGACCGGGTGACC<br>ATCACTTGTAAGGCCTCACA<br>GGATGTTTCTACTGCTGTCG<br>CATGGTACCAGCAAAAGCCG<br>GGTAAAGCTCCCAAGCTTTT<br>GATATACTGGGCCAGCACCA<br>GGCACACAGGCGTGCCATCA<br>AGATTCAGTGGGTCCGGATC<br>CGGCACGGATTTTACACTCA<br>CTATTAGCTCACTGCAACCT<br>GAAGACTTTGCCACCTATTA<br>CTGCCAGCAGCATTATAGCA<br>CCCCTCCCACCTTCGGTCAG<br>GGCACTAAAGTAGAAATCAA<br>A (SEQ ID NO: 50) |
| 4B9H31 | (Protein Sequence)<br>QVQLVESGGGLVKPGGSLR<br>LSCAASGFTFSDYYMYWVR<br>QAPGKGLEWVATISVGGSF<br>TYYPDSVKGRFTISRDNAK<br>NSLYLQMNSLRAEDTAVYY<br>CARDWGLRPWFVYWGQGTL<br>VTVSS (SEQ ID NO: 51) | (Protein Sequence)<br>DIQMTQSPSSLSASVGDRVT<br>ITCKASQDVSTAVAWYQQKP<br>GKAPKLLIYWASTRHTGVPS<br>RFSGSGSGTDFTLTISSLQP<br>EDFATYYCQQHYSTPPTFGQ<br>GTKVEIK (SEQ ID NO: 52) |
| | (Coding Nucleotide Sequence)<br>CAGGTGCAGCTGGTCGAAT<br>CTGGAGGAGGCTTGGTGAA<br>ACCTGGGGGGTCCCTGAGA<br>CTCTCCTTGTCAGCCTCCG<br>GCTTTACCTTTTCTGACTA<br>CTACATGTATTGGGTTCGC<br>CAGGCTCCCGGTAAGGGGT<br>TAGAGTGGGTGGCTACCAT<br>TAGTGTTGGCGGTTCATTT<br>ACTTATTACCCAGATAGTG | (Coding Nucleotide Sequence)<br>GACATCCAGATGACACAGTC<br>CCCAAGCTCCCTGTCTGCAT<br>CTGTGGGAGACCGGGTGACC<br>ATCACTTGTAAGGCCTCACA<br>GGATGTTTCTACTGCTGTCG<br>CATGGTACCAGCAAAAGCCG<br>GGTAAAGCTCCCAAGCTTTT<br>GATATACTGGGCCAGCACCA<br>GGCACACAGGCGTGCCATCA<br>AGATTCAGTGGGTCCGGATC |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| | TGAAAGGACGGTTCACCAT CAGCAGGGACAATGCAAAG AACTCACTCTATCTACAAA TGAATAGCCTGAGAGCCGA GGATACAGCGGTGTATTAC TGCGCCAGAGATTGGGGAC TTCGACCATGGTTCGTCTA CTGGGGCCAGGGAACCCTG GTCACCGTCTCCTCA (SEQ ID NO: 53) | CGGCACGGATTTTACACTCA CTATTAGCTCACTGCAACCT GAAGACTTTGCCACCTATTA CTGCCAGCAGCATTATAGCA CCCCTCCCACCTTCGGTCAG GGCACTAAAGTAGAAATCAA A (SEQ ID NO: 54) |
| 2C8H11 | (Protein Sequence) QVQLVQSGAEVKKPGASVK VSCKASGYTFTSYWMHWVR QAPGQGLEWMGMIDPSDSE TRLNQKFKDRVTMTRDTST STVYMELSSLRSEDTAVYY CARRFYYGSDWYFDVWGQG TLVTVSS (SEQ ID NO: 55) | (Protein Sequence) DIQLTQSPSFLSASVGDRVT ITCKASQDVGTAVAWYQQKP GKAPKLLIYWASTRHTGVPS RFSGSGSGTEFTLTISSLQP EDFATYYCQQYSSYPLTFGQ GTKVEIK (SEQ ID NO: 56) |
| | (Coding Nucleotide Sequence) CAGGTGCAGCTGGTGCAGA GTGGAGCTGAGGTAAAAAA GCCCGGCGCCAGTGTGAAG GTTAGTTGCAAGGCCTCTG GATACACCTTCACAAGCTA TTGGATGCACTGGGTCGCA CAAGCTCCTGGGCAGGGGC TTGAGTGGATGGGAATGAT CGACCCATCCGATTCAGAA ACTAGGCTCAACCAGAAAT TCAAAGATAGAGTGACTAT GACCAGGGACACCTCCACG AGCACAGTCTACATGGAAT TGTCAAGCCTGCGCTCTGA GGACACAGCCGTGTACTAT TGTGCAAGACGGTTTTACT ATGGTAGCGATTGGTACTT TGATGTTTGGGGCCAGGGA ACCCTGGTCACCGTCTCCT CA (SEQ ID NO: 57) | (Coding Nucleotide Sequence) GACATACAGTTGACCCAGTC TCCTTCCTTCCTGTCCGCCT CCGTGGGCGATAGAGTTACC ATTACTTGCAAAGCTAGTCA GGACGTGGGTACCGCAGTGG CCTGGTATCAGCAGAAACCA GGTAAAGCCCCTAAGCTCCT GATCTACTGGGCATCAACAC GGCACACAGGGGTCCCAAGC AGGTTTTCTGGCAGCGGATC AGGAACCGAATTTACACTGA CGATCCGTCTCTGCAGCCC GAGGATTTCGCTACTTACTA CTGTCAACAATATAGTAGCT ATCCCCTCACTTTCGGTCAG GGCACTAAAGTAGAAATCAA A (SEQ ID NO: 58) |
| 2C8H21 | (Protein Sequence) QVQLVQSGAEVKKPGASVK VSCKASGYSFTSYWMHWVR QAPGQGLEWIGMIDPSDSE TRLNQKFKDRVTMTRDTST STVYMELSSLRSEDTAVYY CARRFYYGSDWYFDVWGQG TLVTVSS (SEQ ID NO: 59) | (Protein Sequence) DIQLTQSPSFLSASVGDRVT ITCKASQDVGTAVAWYQQKP GKAPKLLIYWASTRHTGVPS RFSGSGSGTEFTLTISSLQP EDFATYYCQQYSSYPLTFGQ GTKVEIK (SEQ ID NO: 60) |
| | (Coding Nucleotide Sequence) CAGGTGCAACTCGTGCAGT CTGGAGCTGAAGTGAAGAA ACCCGGGGCCTCAGTGAAG GTGAGTTGCAAAGCATCTG GTACTCATTTACAGCTA TTGGATGCACTGGGTGCGG CAGGCCCCAGGACAAGGCC TGGAGTGGATTGGCATGAT CGACCCTTCCGATAGTGAA ACGAGGCTGAACCAGAAGT TTAAAGATCGCGTCACCAT GACCAGGGACACAAGTACT TCTACAGTCTACATGGAGT TGAGCAGCCTGAGATCAGA GGACACAGCCGTTTACTAC | (Coding Nucleotide Sequence) GACATACAGTTGACCCAGTC TCCTTCCTTCCTGTCCGCCT CCGTGGGCGATAGAGTTACC ATTACTTGCAAAGCTAGTCA GGACGTGGGTACCGCAGTGG CCTGGTATCAGCAGAAACCA GGTAAAGCCCCTAAGCTCCT GATCTACTGGGCATCAACAC GGCACACAGGGGTCCCAAGC AGGTTTTCTGGCAGCGGATC AGGAACCGAATTTACACTGA CGATCCGTCTCTGCAGCCC GAGGATTTCGCTACTTACTA CTGTCAACAATATAGTAGCT ATCCCCTCACTTTCGGTCAG |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| | TGTGCTAGACGATTCTATT ATGGCAGCGACTGGTATTT CGATGTATGGGGCCAGGGA ACCCTGGTCACCGTCTCCT CA (SEQ ID NO: 61) | GGCACTAAAGTAGAAATCAA A (SEQ ID NO: 62) |
| 2C8H31 | (Protein Sequence) QVQLVQSGAEVKKPGASVK VSCKASGYSFTSYWMHWVR QAPGQGLEWIGMIDPSDSE TRLNQKFKDKASMTRDTST STVYMELSSLRSEDTAVYY CARRFYYGSDWYFDVWGQG TLVTVSS (SEQ ID NO: 63) | (Protein Sequence) DIQLTQSPSFLSASVGDRVT ITCKASQDVGTAVAWYQQKP GKAPKLLIYWASTRHTGVPS RFSGSGSGTEFTLTISSLQP EDFATYYCQQYSSYPLTFGQ GTKVEIK (SEQ ID NO: 64) |
| | (Coding Nucleotide Sequence) CAGGTGCAACTGGTGCAGT CTGGTGCAGAGGTGAAGAA ACCAGGCGCTTCAGTCAAG GTAAGCTGCAAAGCAAGTG GATACTCCTTCACCTCTTA TTGGATGCACTGGGTTAGA CAGGCCCCTGGTCAAGGCC TCGAGTGGATTGGCATGAT CGACCCCTCTGACAGCGAA ACTAGGCTGAATCAGAAAT TAAGGACAAGGCCTCCAT GACACGGGATACATCCACA AGCACCGTTTACATGGAAC TGAGCTCGCTGAGAAGTGA GGACACTGCCGTGTATTAC TGTGCAGACGGCTTTTATT ACGGGTCAGATTGGTACTT CGATGTGTGGGGCCAGGGA ACCCTGGTCACCGTCTCCT CA(SEQ ID NO: 65) | (Coding Nucleotide Sequence) GACATACAGTTGACCCAGTC TCCTTCCTTCCTGTCCGCCT CCGTGGGCGATAGAGTTACC ATTACTTGCAAAGCTAGTCA GGACGTGGGTACCGCAGTGG CCTGGTATCAGCAGAAACCA GGTAAAGCCCCTAAGCTCCT GATCTACTGGGCATCAACAC GGCACACAGGGGTCCCAAGC AGGTTTTCTGGCAGCGGATC AGGAACCGAATTTACACTGA CGATCCGTCTCTGCAGCCC GAGGATTTCGCTACTTACTA CTGTCAACAATATAGTAGCT ATCCCCTCACTTTCGGTCAG GGCACTAAAGTAGAAATCAA A (SEQ ID NO: 66) |
| 2C8H41 | (Protein Sequence) QVQLVQSGAEVKKPGASVK VSCKASGYSFTSYWMHWVK QAPGQGLEWIGMIDPSDSE TRLNQKFKDKASMTRDTST STVYMELSSLRSEDTAVYY CARRFYYGSDWYFDVWGQG TLVTVSS (SEQ ID NO: 67) | (Protein Sequence) DIQLTQSPSFLSASVGDRVT ITCKASQDVGTAVAWYQQKP GKAPKLLIYWASTRHTGVPS RFSGSGSGTEFTLTISSLQP EDFATYYCQQYSSYPLTFGQ GTKVEIK (SEQ ID NO: 68) |
| | (Coding Nucleotide Sequence) CAGGTGCAGCTGGTGCAGT CTGGGGCTGAGGTGAAAAA GCCAGGCGCTTCCGTCAAA GTTTCCTGCAAGGCATCTG GTTACTCTTTTACAAGCTA TTGGATGCACTGGGTGAAG CAGGCCCCCGGACAAGGGC TCGAGTGGATTGGCATGAT CGATCCTTCCGATAGTGAA ACACGTTGAATCAGAAAT TCAAGGACAAGGCCAGTAT GACCAGGGATACTAGCACA AGCACTGTATATATGGAGC TTAGCTCACTGAGAAGTGA AGACACGCCGTGTACTAC TGTGCAGACGGTTTTACT ATGGCTCCGACTGGTATTT CGACGTCTGGGGCCAGGGA ACCCTGGTCACCGTCTCCT CA (SEQ ID NO: 69) | (Coding Nucleotide Sequence) GACATACAGTTGACCCAGTC TCCTTCCTTCCTGTCCGCCT CCGTGGGCGATAGAGTTACC ATTACTTGCAAAGCTAGTCA GGACGTGGGTACCGCAGTGG CCTGGTATCAGCAGAAACCA GGTAAAGCCCCTAAGCTCCT GATCTACTGGGCATCAACAC GGCACACAGGGGTCCCAAGC AGGTTTTCTGGCAGCGGATC AGGAACCGAATTTACACTGA CGATCCGTCTCTGCAGCCC GAGGATTTCGCTACTTACTA CTGTCAACAATATAGTAGCT ATCCCCTCACTTTCGGTCAG GGCACTAAAGTAGAAATCAA A (SEQ ID NO: 70) |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| 2C8H51 | (Protein Sequence)<br>QVQLVQSGAEVKKPGASVK VSCKASGYSFTSYWMHWVK QAPGQGLEWIGMIDPSDE TRLNQKFKDKASLTVDTST STVYMELSSLRSEDTAVYY CARRFYYGSDWYFDVWGQG TLVTVSS (SEQ ID NO: 71)<br><br>(Coding Nucleotide Sequence)<br>CAGGTGCAGCTGGTGCAGT CTGGCGCTGAGGTGAAGAA ACCTGGGGCCTCAGTGAAG GTTTCCTGTAAAGCAAGTG GATACTCTTTCACCAGCTA CTGGATGCACTGGGTGAAA CAGGCCCCGGCCAAGGGC TTGAGTGGATTGGTATGAT CGATCCATCCGACAGCGAA ACTAGGCTCAACCAGAAGT TCAAGGATAAAGCGTCCTT GACAGTAGATACATCCACG AGCACAGTTTATATGGAGC TGTCTAGTCTCCGGTCTGA AGACACCGCCGTGTATTAT TGCGCTAGACGCTTTTATT ACGGCTCGGACTGGTACTT TGACGTCTGGGGCCAGGGA ACCCTGGTCACCGTCTCCT CA (SEQ ID NO: 73) | (Protein Sequence)<br>DIQLTQSPSFLSASVGDRVT ITCKASQDVGTAVAWYQQKP GKAPKLLIYWASTRHTGVPS RFSGSGSGTEFTLTISSLQP EDFATYYCQQYSSYPLTFGQ GTKVEIK (SEQ ID NO: 72)<br><br>(Coding Nucleotide Sequence)<br>GACATACAGTTGACCCAGTC TCCTTCCTTCCTGTCCGCCT CCGTGGGCGATAGAGTTACC ATTACTTGCAAAGCTAGTCA GGACGTGGGTACCGCAGTGG CCTGGTATCAGCAGAAACCA GGTAAAGCCCCTAAGCTCCT GATCTACTGGGCATCAACAC GGCACACAGGGGTCCCAAGC AGGTTTTCTGGCAGCGGATC AGGAACCGAATTTACACTGA CGATCTCGTCTCTGCAGCCC GAGGATTTCGCTACTTACTA CTGTCAACAATATAGTAGTA ATCCCCTCACTTTCGGTCAG GGCACTAAAGTAGAAATCAA A (SEQ ID NO: 74) |
| 2C8H12 | (Protein Sequence)<br>QVQLVQSGAEVKKPGASVK VSCKASGYTFTSYWMHWVR QAPGQGLEWMGMIDPSDE TRLNQKFKDRVTMTRDTST STVYMELSSLRSEDTAVYY CARRFYYGSDWYFDVWGQG TLVTVSS (SEQ ID NO: 75)<br><br>(Coding Nucleotide Sequence)<br>CAGGTGCAGCTGGTGCAGA GTGGAGCTGAGGTAAAAAA GCCCGGCGCCAGTGTGAAG GATACACTTCACAAGCTA TTGGATGCACTGGGTGCGA CAAGCTCCTGGGCAGGGGC TTGAGTGGATGGGAATGAT CGACCCATCCGATTCAGAA ACTAGGCTCAACCAGAAAT TCAAAGATAGAGTGACTAT GACCAGGGACACCTCCACG AGCACAGTCTACATGGAAT TGTCAAGCCTGCGCTCTGA GGACAGCCGTGTACTAT TGTGCAAGACGGTTTTACT ATGGTAGCGATTGGTACTT TGATGTTTGGGGCCAGGGA ACCCTGGTCACCGTCTCCT CA (SEQ ID NO: 77) | (Protein Sequence)<br>DIQLTQSPSFLSASVGDRVS ITCKASQDVGTAVAWYQQKP GKAPKLLIYWASTRHTGVPD RFSGSGSGTEFTLTISSLQP EDFATYYCQQYSSYPLTFGQ GTKVEIK (SEQ ID NO: 76)<br><br>(Coding Nucleotide Sequence)<br>GATATTCAACTCACCCAGAG TCCATCCTTCCTGTCTGCCT CAGTGGGCGACAGAGTGTCA ATCACATGCAAGGCAAGCCA GGATGTTGGCACTGCTGTGG CTTGGTATCAGCAAAAACCA GGTAAGGCCCCCAAACTGCT TATTTACTGGGCATCAACCC GGCACACGGGTGTCCCCGAC AGGTTCAGCGGCAGTGGATC TGGGACAGAGTTTACCCTGA CTATCAGCTCCCTGCAGCCT GAAGACTTTGCCACTTATTA CTGTCAGCAGTACTCTAGCT ATCCTCTCACCTTCGGTCAG GGCACTAAAGTAGAAATCAA A (SEQ ID NO: 78) |
| 2C8H22 | (Protein Sequence)<br>QVQLVQSGAEVKKPGASVK VSCKASGYSFTSYWMHWVR QAPGQGLEWIGMIDPSDE TRLNQKFKDRVTMTRDTST STVYMELSSLRSEDTAVYY CARRFYYGSDWYFDVWGQG TLVTVSS (SEQ ID NO: 79)<br><br>(Coding Nucleotide Sequence)<br>CAGGTGCAACTCGTGCAGT CTGGAGCTGAAGTGAAGAA ACCCGGGGCCTCAGTGAAG GTGAGTTGCAAAGCATCTG GGTACTCATTTACCAGCTA TTGGATGCACTGGGTGCGG CAGGCCCCAGGACAAGGCC TGGAGTGGATTGGCATGAT CGACCCTTCCGATAGTGAA ACGAGGCTGAACCAGAAGT TTAAAGATCGCGTCACCAT TCTACAGTCTACATGAGT TGAGCAGCCTGAGATCAGA GGACACAGCCGTTTACTAC TGTGCTAGACGATTCTATT ATGGCAGCGACTGGTATTT CGATGTATGGGGCCAGGGA ACCCTGGTCACCGTCTCCT CA (SEQ ID NO: 81) | (Protein Sequence)<br>DIQLTQSPSFLSASVGDRVS ITCKASQDVGTAVAWYQQKP GKAPKLLIYWASTRHTGVPD RFSGSGSGTEFTLTISSLQP EDFATYYCQQYSSYPLTFGQ GTKVEIK (SEQ ID NO: 80)<br><br>(Coding Nucleotide Sequence)<br>GATATTCAACTCACCCAGAG TCCATCCTTCCTGTCTGCCT CAGTGGGCGACAGAGTGTCA ATCACATGCAAGGCAAGCCA GGATGTTGGCACTGCTGTGG CTTGGTATCAGCAAAAACCA GGTAAGGCCCCCAAACTGCT TATTTACTGGGCATCAACCC GGCACACGGGTGTCCCCGAC AGGTTCAGCGGCAGTGGATC TGGGACAGAGTTTACCCTGA CTATCAGCTCCCTGCAGCCT GAAGACTTTGCCACTTATTA CTGTCAGCAGTACTCTAGCT ATCCTCTCACCTTCGGTCAG GGCACTAAAGTAGAAATCAA A (SEQ ID NO: 82) |
| 2C8H32 | (Protein Sequence)<br>QVQLVQSGAEVKKPGASVK VSCKASGYSFTSYWMHWVR QAPGQGLEWIGMIDPSDE TRLNQKFKDKASMTRDTST STVYMELSSLRSEDTAVYY CARRFYYGSDWYFDVWGQG TLVTVSS (SEQ ID NO: 83)<br><br>(Coding Nucleotide Sequence)<br>CAGGTGCAACTGGTGCAGT CTGGTGCTGAGGTGAAGAA ACCAGGCGCTTCAGTCAAG GTAAGCTGCAAAGCAAGTG GATACTCCTTCACCTCTTA TTGGATGCACTGGGTTAGA CAGGCCCCTGGTCAAGGCC TCGAGTGGATTGGCATGAT CGACCCCTCTGACAGCGAA ACTAGGCTGAATCAGAAAT TTAAGGACAAGGCCTCCAT GACACGGGATACCTCTGCT AGCACCGTTTACATGGAAC TGAGCTCGCTGAGAAGTGA GGACACTGCCGTGTATTAC TGTGCGAGACGCTTTTATT ACGGTCAGATTGGTACTT CGATGTGTGGGGCCAGGGA ACCCTGGTCACCGTCTCCT CA (SEQ ID NO: 85) | (Protein Sequence)<br>DIQLTQSPSFLSASVGDRVS ITCKASQDVGTAVAWYQQKP GKAPKLLIYWASTRHTGVPD RFSGSGSGTEFTLTISSLQP EDFATYYCQQYSSYPLTFGQ GTKVEIK (SEQ ID NO: 84)<br><br>(Coding Nucleotide Sequence)<br>GATATTCAACTCACCCAGAG TCCATCCTTCCTGTCTGCCT CAGTGGGCGACAGAGTGTCA ATCACATGCAAGGCAAGCCA GGATGTTGGCACTGCTGTGG CTTGGTATCAGCAAAAACCA GGTAAGGCCCCCAAACTGCT TATTTACTGGGCATCAACCC GGCACACGGGTGTCCCCGAC AGGTTCAGCGGCAGTGGATC TGGGACAGAGTTTACCCTGA CTATCAGCTCCCTGCAGCCT GAAGACTTTGCCACTTATTA CTGTCAGCAGTACTCTAGCT ATCCTCTCACCTTCGGTCAG GGCACTAAAGTAGAAATCAA A (SEQ ID NO: 86) |
| 2C8H42 | (Protein Sequence)<br>QVQLVQSGAEVKKPGASVK VSCKASGYSFTSYWMHWVK QAPGQGLEWIGMIDPSDE TRLNQKFKDKASMTRDTST STVYMELSSLRSEDTAVYY CARRFYYGSDWYFDVWGQG TLVTVSS (SEQ ID NO: 87)<br><br>(Coding Nucleotide Sequence)<br>CAGGTGCAGCTGGTGCAGT | (Protein Sequence)<br>DIQLTQSPSFLSASVGDRVS ITCKASQDVGTAVAWYQQKP GKAPKLLIYWASTRHTGVPD RFSGSGSGTEFTLTISSLQP EDFATYYCQQYSSYPLTFGQ GTKVEIK (SEQ ID NO: 88)<br><br>(Coding Nucleotide Sequence)<br>GATATTCAACTCACCCAGAG |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| | CTGGGGCTGAGGTGAAAAA GCCAGGCGCTTCCGTCAAA GTTTCCTGCAAGGCATCTG GTTACTCTTTTACAAGCTA TTGGATGCACTGGGTGAAG CAGGCCCCCGGACAGGGC TCGAGTGGATTGGCATGAT CGATCCTTCCGATAGTGAA ACACGCTTGAATCAGAAAT TCAAGGACAAGGCCAGTAT GACCAGGGATACTAGCACA AGCACTGTATATATGGAGC TTAGCTCACTGAGATCAGA AGACACGGCCGTGTACTAC TGTGCGAGACGGTTTTATT ATGGCTCCGACTGGTATTT CGACGTCTGGGGCCAGGGA ACCCTGGTCACCGTCTCCT CA(SEQ ID NO: 89) | TCCATCCTTCCTGTCTGCCT CAGTGGGCGACAGAGTGTCA ATCACATGCAAGGCAAGCCA GGATGTTGGCACTGCTGTGG CTTGGTATCAGCAAAAACCA GGTAAGGCCCCCAAACTGCT TATTTACTGGGCATCAACCC GGCACACGGGTGTCCCCGAC AGGTTCAGCGGCAGTGGATC TGGGACAGAGTTTACCCTGA CTATCAGCTCCCTGCAGCCT GAAGACTTTGCCACTTATTA CTGTCAGCAGTACTCTAGCT ATCCTCTCACCTTCGGTCAG GGCACTAAAGTAGAAATCAA A (SEQ ID NO: 90) |
| 2C8H52 | (Protein Sequence) QVQLVQSGAEVKKPGASVK VSCKASGYSFTSYWMHWVK QAPGQGLEWIGMIDPSDSE TRLNQKFKDKASLTVDTST STVYMELSSLRSEDTAVYY CARRFYYGSDWYFDVWGQG TLVTVSS (SEQ ID NO: 91) | (Protein Sequence) DIQLTQSPSPSFLSASVGDRVS ITCKASQDVGTAVAWYQQKP GKAPKLLIYWASTRHTGVPD RFSGSGSGTEFTLTISSLQP EDFATYYCQQYSSYPLTFGQ GTKVEIK (SEQ ID NO: 92) |
| | (Coding Nucleotide Sequence) CAGGTGCAGCTGGTGCAGT CTGGCGCTGAGGTGAAGAA ACCTGGGGCCTCAGTGAAG GTTTCCTGTAAAGCAAGTG GATACTCTTTCACCAGCTA CTGGATGCACTGGGTGAAA CAGGCCCCCGGCCAAGGGC TTGAGTGGATTGGTATGAT CGATCCATCCGACAGCGAA ACTAGGCTCAACCAGAAGT TCAAGGATAAAGCGTCCTT GACAGTAGATACATCCACT AGCACAGTTTATATGGAGC TGTCTAGTCTGCGGTCTGA AGACACCGCCGTGTATTAT TGCGCTAGACGCTTTTATT ACGGCTCGGACTGGTACTT TGACGTCTGGGGCCAGGGA ACCCTGGTCACCGTCTCCT CA (SEQ ID NO: 93) | (Coding Nucleotide Sequence) GATATTCAACTCACCCAGAG TCCATCCTTCCTGTCTGCCT CAGTGGGCGACAGAGTGTCA ATCACATGCAAGGCAAGCCA GGATGTTGGCACTGCTGTGG CTTGGTATCAGCAAAAACCA GGTAAGGCCCCCAAACTGCT TATTTACTGGGCATCAACCC GGCACACGGGTGTCCCCGAC AGGTTCAGCGGCAGTGGATC TGGGACAGAGTTTACCCTGA CTATCAGCTCCCTGCAGCCT GAAGACTTTGCCACTTATTA CTGTCAGCAGTACTCTAGCT ATCCTCTCACCTTCGGTCAG GGCACTAAAGTAGAAATCAA A (SEQ ID NO: 94) |
| 2C8H13 | (Protein Sequence) QVQLVQSGAEVKKPGASVK VSCKASGYTFTSYWMHWVR QAPGQGLEWMGMIDPSDSE TRLNQKFKDRVTMTRDTST STVYMELSSLRSEDTAVYY CARRFYYGSDWYFDVWGQG TLVTVSS (SEQ ID NO: 95) | (Protein Sequence) DIQLTQSPSPSFLSASVGDRVS ITCKASQDVGTAVAWYQQKP GKAPKLLIYWASTRHTGVPD RFSGSGSGTEFTLTISSLQP EDFADYFCQQYSSYPLTFGQ GTKVEIK (SEQ ID NO: 96) |
| | (Coding Nucleotide Sequence) CAGGTGCAGCTGGTGCAGA GTGGAGCTGAGGTAAAAAA GCCCGGCGCCAGTGTGAAG GTTAGTTGCAAGGCCTCAG GATACACCTTCACAAGCTA TTGGATGCACTGGGTGCGA CAAGCTCCTGGGCAGGGGC TTGAGTGGATGGGAATGAT CGACCCATCCGATTCAGAA | (Coding Nucleotide Sequence) GACATCCAGTTGACCCAATC ACCATCCTTTCTGTCTGCCT CTGTGGGAGATAGAGTCTCC ATTACTTGCAAGGCCAGTCA GGATGTTGGGGACCGCTGTTG CCTGGTACCAGCAAAAACCC GGAAAGGCACCTAAACTCCT TATCTACTGGGCATCCACCC GGCACACAGGAGTGCCAGAC |
| | ACTAGGCTCAACCAGAAAT TCAAAGATAGAGTGACTAT GACCAGGGACACCTCCACG AGCACAGTCTACATGGAAT TGTCAAGCCTGCGCTCTGA GGACACAGCCGTGTACTAT TGTGCAAGACGGTTTTACT ATGGTAGCGATTGGTACTT TGATGTTGGGGCCAGGGA ACCCTGGTCACCGTCTCCT CA (SEQ ID NO: 97) | AGGTTTAGCGGGTCAGGCTC TGGTACAGAGTTCACTCTGA CAATTTCTAGCCTGCAGCCT GAAGACTTCGCTGATTATTT CTGTCAGCAGTATAGCAGTT ACCCCCTCACGTTCGGTCAG GGCACTAAAGTAGAAATCAA A (SEQ ID NO: 98) |
| 2C8H23 | (Protein Sequence) QVQLVQSGAEVKKPGASVK VSCKASGYSFTSYWMHWVR QAPGQGLEWIGMIDPSDSE TRLNQKFKDRVTMTRDTST STVYMELSSLRSEDTAVYY CARRFYYGSDWYFDVWGQG TLVTVSS (SEQ ID NO: 99) | (Protein Sequence) DIQLTQSPSPSFLSASVGDRVS ITCKASQDVGTAVAWYQQKP GKAPKLLIYWASTRHTGVPD RFSGSGSGTEFTLTISSLQP EDFADYFCQQYSSYPLTFGQ GTKVEIK (SEQ ID NO: 100) |
| | (Coding Nucleotide Sequence) CAGGTGCAACTCGTGCAGT CTGGAGCTGAAGTGAAGAA ACCCGGGGCCTCAGTGAAG GTGAGTTGCAAAGCATCTG GGTACTCATTTACCAGCTA TTGGATGCACTGGGTGCGG CAGGCCCCAGGACAAGGCC TGGAGTGGATTGGCATGAT CGACCCTTCCGATAGTGAA ACGAGGCTGAACCAGAAGT TTAAAGATCGCGTCACCAT GACCAGGGACACAAGTACT TCTACAGTCTACATGGAGT TGAGCAGCCTGAGATCAGA GGACACAGCCGTTTACTAC TGTGCTAGACGGTTTTATT ATGGCAGCGACTGGTATTT CGATGTATGGGGCCAGGGA ACCCTGGTCACCGTCTCCT CA (SEQ ID NO: 101) | (Coding Nucleotide Sequence) GACATCCAGTTGACCCAATC ACCATCCTTTCTGTCTGCCT CTGTGGGAGATAGAGTCTCC ATTACTTGCAAGGCCAGTCA GGATGTTGGGGACCGCTGTTG CCTGGTACCAGCAAAAACCC GGAAAGGCACCTAAACTCCT TATCTACTGGGCATCCACCC GGCACACAGGAGTGCCAGAC AGGTTTAGCGGGTCAGGCTC TGGTACAGAGTTCACTCTGA CAATTTCTAGCCTGCAGCCT GAAGACTTCGCTGATTATTT CTGTCAGCAGTATAGCAGTT ACCCCCTCACGTTCGGTCAG GGCACTAAAGTAGAAATCAA A (SEQ ID NO: 102) |
| 2C8H33 | (Protein Sequence) QVQLVQSGAEVKKPGASVK VSCKASGYSFTSYWMHWVR QAPGQGLEWIGMIDPSDSE TRLNQKFKDKASMTRDTST STVYMELSSLRSEDTAVYY CARRFYYGSDWYFDVWGQG TLVTVSS (SEQ ID NO: 103) | (Protein Sequence) DIQLTQSPSPSFLSASVGDRVS ITCKASQDVGTAVAWYQQKP GKAPKLLIYWASTRHTGVPD RFSGSGSGTEFTLTISSLQP EDFADYFCQQYSSYPLTFGQ GTKVEIK (SEQ ID NO: 104) |
| | (Coding Nucleotide Sequence) CAGGTGCAACTGGTGCAGT CTGGTGCTGAGGTGAAGAA ACCAGGCGCTTCAGTCAAG GTAAGCTGCAAAGCAAGTCA GATACTCCTTCACCTCTTA TTGGATGCACTGGGTTAGA CAGGCCCCTGGTCAAGGCC TCGAGTGGATTGGCATGAT CGACCCCTCTGACAGCGAA ACTAGGCTGAATCAGAAAT TTAAGGACAAGGCCTCCAT GACACGGGATACATCCACA AGCACCGTTTACATGGAAC TGAGCTCGCTGAGAAGTGA AGACACTGCCGTGTATTAC TGTGCGAGACGCTTTTATT ACGGGTCAGATTGGTACTT | (Coding Nucleotide Sequence) GACATCCAGTTGACCCAATC ACCATCCTTTCTGTCTGCCT CTGTGGGAGATAGAGTCTCC ATTACTTGCAAGGCCAGTCA GGATGTTGGGGACCGCTGTTG CCTGGTACCAGCAAAAACCC GGAAAGGCACCTAAACTCCT TATCTACTGGGCATCCACCC GGCACACAGGAGTGCCAGAC AGGTTTAGCGGGTCAGGCTC TGGTACAGAGTTCACTCTGA CAATTTCTAGCCTGCAGCCT GAAGACTTCGCTGATTATTT CTGTCAGCAGTATAGCAGTT ACCCCCTCACGTTCGGTCAG GGCACTAAAGTAGAAATCAA A (SEQ ID NO: 106) |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| | CGATGTGTGGGGCCAGGGA ACCCTGGTCACCGTCTCCT CA (SEQ ID NO: 105) | |
| 2C8H43 | (Protein Sequence) QVQLVQSGAEVKKPGASVK VSCKASGYSFTSYWMHWVK QAPGQGLEWIGMIDPSDSE TRLNQKFKDKASMTRDTST STVYMELSSLRSEDTAVYY CARRFYYGSDWYFDVWGQG TLVTVSS (SEQ ID NO: 107) | (Protein Sequence) DIQLTQSPSFLSASVGDRVS ITCKASQDVGTAVAWYQQKP GKAPKLLIYWASTRHTGVPD RFSGSGSGTEFTLTISSLQP EDFADYFCQQYSSYPLTFGQ GTKVEIK (SEQ ID NO: 108) |
| | (Coding Nucleotide Sequence) CAGGTGCAGCTGGTGCAGT CTGGGGCTGAGGTGAAAAA GCCAGGCGCTTCCGTCAAA GTTTCCTGCAAGGCATCTG GTTACTCTTTTACAAGCTA TTGGATGCACTGGGTGAAG CAGGCCCCCGGACAAGGGC TCGAGTGGATTGGCATGAT CGATCCTTCCGATAGTGAA ACACGCTTGAATCAGAAAT TCAAGGACAAGGCCAGTAT GACCAGGGATACTAGCACA AGCACTGTATATATGGAGC TTAGCTCACTGAGATCAGA AGACACGGCCGTGTACTAC TGTGCGAGACGGTTTTACT ATGGCTCCGACTGGTATTT CGACGTCTGGGGCCAGGGA ACCCTGGTCACCGTCTCCT CA (SEQ ID NO: 109) | (Coding Nucleotide Sequence) GACATCCAGTTGACCCAATC ACCATCCTTTCTGTCTGCCT CTGTGGGAGATAGAGTCTCC ATTACTTGCAAGGCCAGTCA GGATGTGGGGACCGCTGTTG CCTGGTACCAGCAAAAACCC GGAAAGGCACCTAAACTCCT TATCTACTGGGCATCCACCC GGCACACAGGAGTGCCAGAC AGGTTTAGCGGGTCAGGCTC TGGTACAGAGTTCACTCTGA CAATTTCTAGCCTGCAGCCT GAAGACTTCGCTGATTATTT CTGTCAGCAGTATAGCAGTT ACCCCCTCACGTTCGGTCAG GGCACTAAAGTAGAAATCAA A (SEQ ID NO: 110) |
| 2C8H53 | (Protein Sequence) QVQLVQSGAEVKKPGASVK VSCKASGYSFTSYWMHWVK QAPGQGLEWIGMIDPSDSE TRLNQKFKDKASLTVDTST STVYMELSSLRSEDTAVYY CARRFYYGSDWYFDVWGQG TLVTVSS (SEQ ID NO: 111) | (Protein Sequence) DIQLTQSPSFLSASVGDRVS ITCKASQDVGTAVAWYQQKP GKAPKLLIYWASTRHTGVPD RFSGSGSGTEFTLTISSLQP EDFADYFCQQYSSYPLTFGQ GTKVEIK (SEQ ID NO: 112) |
| | (Coding Nucleotide Sequence) CAGGTGCAGCTGGTGCAGT CTGGCGCTGAGGTGAAGAA ACCTGGGGCCTCAGTGAAG GTTTCCTGTAAAGCAAGTG GATACTCTTTCACCAGCTA CTGGATGCACTGGGTGAAA CAGGCCCCCGGCCAAGGGC TTGAGTGGATTGGTATGAT CGATCCATCCGACAGCGAA ACTAGGCTCAACCAGAAGT TCAAGGATAAAGCGTCCTT GACAGTAGATACATCCACG AGCACAGTTTATATGGAGC TGTCTAGTCTGCGGTCTGA AGACACCGCCGTGTATTAT TGCGCTAGACGCTTTTATT ACGGCTCGGACTGGTACTT TGACGTCTGGGGCCAGGGA ACCCTGGTCACCGTCTCCT CA (SEQ ID NO: 113) | (Coding Nucleotide Sequence) GACATCCAGTTGACCCAATC ACCATCCTTTCTGTCTGCCT CTGTGGGAGATAGAGTCTCC ATTACTTGCAAGGCCAGTCA GGATGTGGGGACCGCTGTTG CCTGGTACCAGCAAAAACCC GGAAAGGCACCTAAACTCCT TATCTACTGGGCATCCACCC GGCACACAGGAGTGCCAGAC AGGTTTAGCGGGTCAGGCTC TGGTACAGAGTTCACTCTGA CAATTTCTAGCCTGCAGCCT GAAGACTTCGCTGATTATTT CTGTCAGCAGTATAGCAGTT ACCCCCTCACGTTCGGTCAG GGCACTAAAGTAGAAATCAA A (SEQ ID NO: 114) |

4-4: Production and Purification of Humanized Anti-Ang2 Antibodies

To produce humanized anti-Ang2 antibodies, Expi293F (Gibco) cells capable of producing recombinant proteins with high efficiency were used. Expi293F cells ($2 \times 10^6$ cells/ml) were cultured in Erlenmeyer flask, and plasmids encoding heavy chain and light chain were co-transfected into Expi293F cells with the ExpiFectamine 293 transfection kit. Cells were cultured at 37° C. under 8% $CO_2$ for 5 days in a shaking incubator (orbital shaker, 125 rpm). The resulting culture medium was collected and centrifuged to remove the cells. The culture supernatant containing secreted antibodies was isolated and stored at 4° C. or immediately purified using an AKTA purification system (GE Healthcare) equipped with an affinity column (Protein A agarose column, GE Healthcare). The purified antibody was concentrated by passing it through a 0.2 μm protein centrifugal filter (Amicon) while the solution was replaced with PBS.

Example 5: Affinity Measurement of Humanized Anti-Ang2 Antibodies Against hAng2

The affinity of humanized anti-Ang2 antibody against hAng2 was measured using Octet system (ForteBio). Specifically, buffer and samples were measured in total 200 μl/well using Black 96-well plates (96 well F-type black plates, Greiner). The biosensor used for affinity measurements was hydrated for 10 min before measurement with AR2G tip (ForteBio Octet). After the hydration, humanized anti-Ang2 antibody was diluted in 10 mM sodium acetate, pH 6.0 buffer at a concentration of 10 μg/ml, fixed on AR2G biosensor, and blocked with 1M ethanolamine. The recombinant hAng2 was diluted to 50, 25, 12.5, 6.25, 3.125, and 0 nM with 1× kinetic buffer, and subjected to association for 300 sec and dissociation for 900 sec. For affinity measurement ($K_D$), association rate (K-on) and dissociation rate (K-off) were analyzed by binding curve (global) and fitted to 1:1 binding model using Octet data analysis v9.0.0.10 program. The $K_D$ values were shown in the following Table 14-15.

The affinities of humanized 4B9 antibodies to hAng2 were summarized in Table 14. The affinities of humanized 2C8 antibodies to hAng2 were in Table 15. In addition, IgG4 class 2C8H11G4 and 4B9H11G4 antibodies also showed subnanomolar high affinities to hAng2 antigen (Table 16).

TABLE 14

Affinities of humanized 4B9 antibodies to hAng2

| Antibody | Kon (1/Ms) | Kdis (1/s) | $K_D$ (M) |
|---|---|---|---|
| 4B9H11 | 9.29E+04 | 1.58E−06 | 1.71E−11 |
| 4B9H21 | 7.37E+04 | 8.94E−06 | 1.21E−10 |
| 4B9H31 | 9.39E+04 | 1.56E−05 | 1.67E−10 |

TABLE 15

Affinities of humanized 2C8 antibodies to hAng2

| Antibody | Kon (1/Ms) | Kdis (1/s) | $K_D$ (M) |
|---|---|---|---|
| 2C8H11 | 6.60E+04 | 1.40E−05 | 2.12E−10 |
| 2C8H21 | 1.11E+05 | 1.50E−05 | 1.35E−10 |
| 2C8H31 | 8.32E+04 | 2.21E−05 | 2.66E−10 |
| 2C8H41 | 6.70E+04 | 1.67E−05 | 2.49E−10 |
| 2C8H51 | 7.02E+04 | 9.61E−06 | 1.37E−10 |
| 2C8H12 | 9.52E+04 | 1.33E−05 | 1.39E−10 |
| 2C8H22 | 5.96E+04 | 6.84E−06 | 1.15E−10 |
| 2C8H32 | 7.57E+04 | 1.49E−05 | 1.97E−10 |
| 2C8H42 | 8.06E+04 | 3.07E−05 | 3.81E−10 |

TABLE 15-continued

Affinities of humanized 2C8 antibodies to hAng2

| Antibody | Kon (1/Ms) | Kdis (1/s) | $K_D$ (M) |
|---|---|---|---|
| 2C8H52 | 8.19E+04 | 1.99E−05 | 2.43E−10 |
| 2C8H13 | 1.13E+05 | 2.77E−05 | 2.46E−10 |
| 2C8H23 | 7.95E+04 | 2.28E−05 | 2.87E−10 |
| 2C8H33 | 8.96E+04 | 3.99E−06 | 4.45E−11 |
| 2C8H43 | 7.11E+04 | 2.65E−05 | 3.73E−10 |
| 2C8H53 | 8.09E+04 | 3.11E−05 | 3.84E−10 |

TABLE 16

Affinities of IgG4 class 2C8H11G4 and 4B9H11G4 antibodies to hAng2

| Antibody | Kon (1/Ms) | Kdis (1/s) | $K_D$ (M) |
|---|---|---|---|
| 2C8H11G4 | 4.15E+05 | 4.35E−06 | 1.05E−11 |
| 4B9H11G4 | 4.32E+05 | 3.46E−05 | 8.00E−11 |

Example 6: Analysis of In-Vitro Biological Property of the Selected Humanized Anti-Ang2 Antibodies 6-1: Akt Phosphorylation To investigate whether the humanized anti-Ang2 antibodies induce the downstream signaling of the Tie2 receptor in endothelial cells, HUVECs (Lonza) were treated with human Ang2 protein together with humanized anti-Ang2 antibody. Then, the level of Akt phosphorylation, the main downstream signaling protein of Tie2 receptor was measured by immunoblotting. To compare the degree of Akt activation, cells were treated with full-length hAng2 (R&D systems) alone or antibody alone in the experiment.

Specifically, HUVEC cells (1×10⁵ cells/nil) were cultured in EGM-2 (Lonza) at 37° C. in 60 mm culture dish. Cells of 90% confluency were incubated with EBM-2 (Lonza) for 4 hrs. The serum-starved HUVECs were treated with the mixture of anti-Ang2 antibody and hAng2 protein (1 µg/ml, R&D system), and further incubated for 30 min. The cells were washed with cold PBS, treated with lysis buffer, and lysed at 4° C. for 20 min. Then, the cell lysates were prepared by centrifugation at 13000 rpm for 15 min. 5×SDS sample buffer was added to the cell lysate and the mixture was boiled at 95° C. for 5 min. Then, the mixture was subjected to SDS-PAGE and subsequent Western blotting.

To investigate the phosphorylation of Akt, the membrane was blocked with 5% skim milk-containing TBST for 1 hr at RT, and incubated with anti-phospho-Akt antibody (S473) at 4° C. for about 8 hrs. The amount of phospho-Akt was visualized by enhanced chemiluminescence (ECL). Then, the membrane was incubated in a stripping buffer (Thermo) for 15 min, and then reprobed with an anti-Akt antibody to determine the amount of total Akt.

Figure 3A:
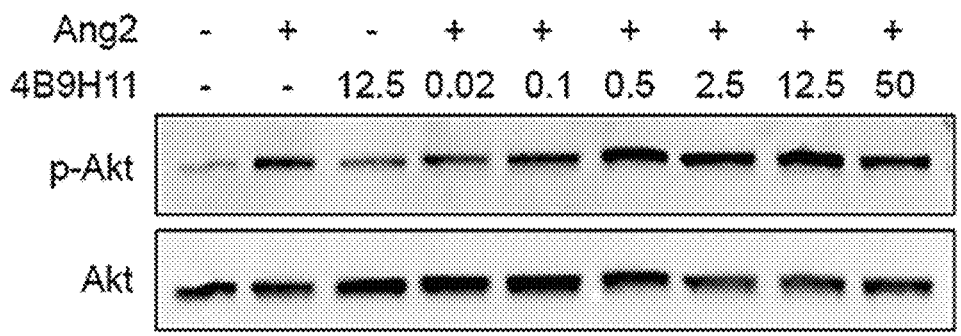
FIGS. 3A-3B. Dose-dependent phosphorylation of Akt (pAkt) by humanized anti-Ang2 antibodies, 4B9H11 (FIG. 3A) and 2C8H11 (FIG. 3B). Serum-starved HUVECs were incubated for 30 min with human Ang2, anti-Ang2 antibodies, or human Ang2 together with various concentrations of anti-Ang2 antibodies. The cell lysates were subjected to SDS-PAGE/Western blotting.
Figure 3B:
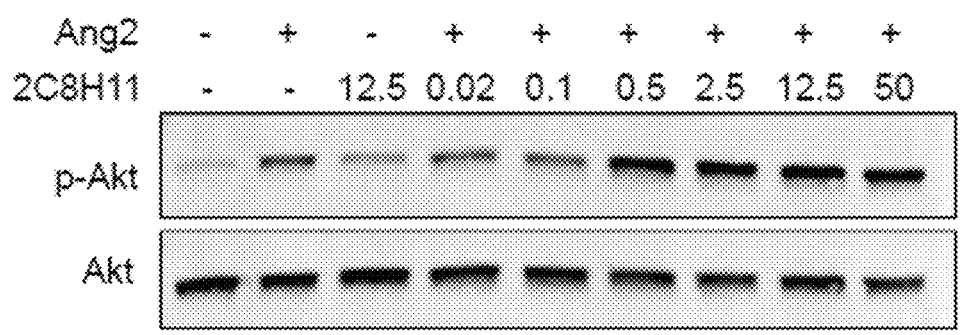

As shown in FIGS. 3A-3B, Akt phosphorylation increased markedly by the treatment of 0.5 µg/ml of anti-Ang2 antibody in the presence of hAng2, and was maintained until 50 µg/ml of antibody concentration in both 4B9H11- and 2C8H11-treated groups. These data indicate that the humanized anti-Ang2 antibodies are able to strongly induce the activation of Akt, the main downstream signaling molecule of Tie2 receptor in endothelial cells. Similar pattern was observed when humanized 4B9H11- or 2C8H11-IgG4 antibodies was tested.

6-2: Tie2 Phosphorylation Induced by Humanized Anti-Ang2 Antibodies

Ang2 binds to the Tie2 receptor and acts as a weak agonist or antagonist. The anti-Ang2 antibody developed in this invention binds to Ang2 to induce Ang2-antibody complexes, further causing clustering of Tie2 receptors and consequently enhancing activation of Tie2 receptor. Experiments were conducted to analyze the effect of anti-Ang2 antibody on Tie2 phosphorylation using HUVECs.

Specifically, HUVECs (Lonza) were cultured in EGM-2 (Lonza) at 37° C. and 5% $CO_2$ concentration in a 100 mm culture dish. At 80-90% confluency, the cells were changed to EBM-2 (Lonza) medium for 2 hrs~6 hrs for serum starvation. Humanized anti-Ang2 antibodies at various concentrations (0.02 µg/ml to 50 µg/ml) were mixed with hAng2 protein (1 µg/ml, R&D systems) for 30 min. Then, the mixtures were treated with the cultured cells and further incubated for 30 min. The cells were washed twice with cold PBS and then lysed in 1000 µl of lysis buffer (10 mM Tris-Cl pH 7.4, 150 mM NaCl, 5 mM EDTA, 10% glycerol, 1% Triton X-100, protease inhibitor, phosphatase inhibitor) and then lysed at 4° C. for 60 min. Cell extracts were prepared and centrifuged at 12,000 rpm for 10 min. The supernatant was quantitated by BCA assay.

To 0.5 mg of cell lysate, 1 µg of Tie2 antibody (R&D systems, AF313) was added and incubated overnight at 4° C. Then, Dynabeads™ Protein G (Life technologies) was added to react for 2 hrs and immunoprecipitation was performed. The beads were immobilized on one side of the tube using a magnet, washed three times with lysis buffer, and then incubated at 70° C. for 10 min with 2×SDS sample buffer containing reducing agent. The beads were removed from the sample and electrophoresed on a 4-15% SDS protein gel (Bio-Rad) and then transferred to a 0.45 µm PVDF membrane.

Figure 4A:
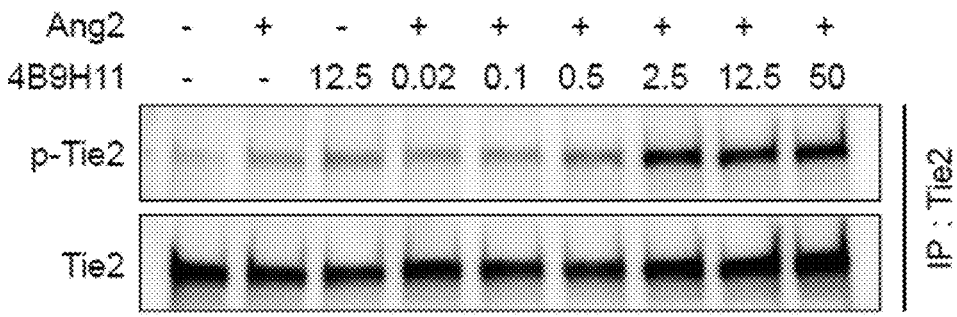
FIGS. 4A-4B. Dose-dependent Tie2 phosphorylation (pTie2) by humanized anti-Ang2 antibodies, 4B9H11 and 2C8H11. The capabilities of 4B9H11 (FIG. 4A) and 2C8H11 (FIG. 4B) antibodies to induce Tie2 phosphorylation were investigated by immunoprecipitation and Western analyses. Serum-starved HUVECs were incubated for 30 min with human Ang2, anti-Ang2 antibody alone, or human Ang2 together with various concentrations of anti-Ang2 antibodies. The cell lysates were subjected to immunoprecipitation with anti-Tie2 antibody, followed by SDS-PAGE/Western blotting analyses.
Figure 4B:
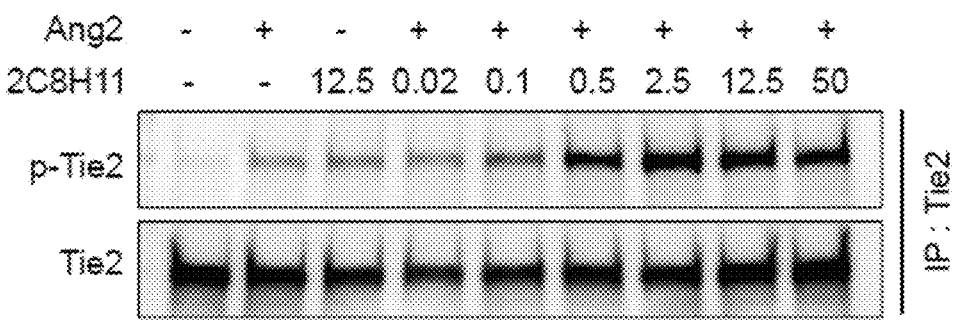

The membrane was blocked with TBS-T mixed with 5% (v/v) BSA for 1 hr at room temperature and incubated with anti-phospho tyrosine antibody (4G10, Millipore) for 8 hrs at 4° C., followed by the incubation of HRP-conjugated anti-mouse antibody and subsequent Western blotting. To measure the amount of immunoprecipitated Tie2, the membrane was reacted in a stripping buffer (Thermo) for 15 min, then blocked again and reprobed with anti-Tie2 antibody (R&D systems, AF313). As shown in FIGS. 4A-4B, when the anti-Ang2 antibody was added together with Ang2 to the HUVEC cells, the phosphorylation of Tie2 was strongly induced in a dose-dependent manner, like in FIGS. 3A-3B. Similar pattern was observed when humanized 4B9H11- or 2C8H11-IgG4 antibodies was tested. These data indicate that the humanized anti-Ang2 antibodies 2C8H11 and 4B9H11 directly induce the activation of Tie2 receptor in human endothelial cells.

6-3: Tie2 Clustering and FOXO1 Translocation in HUVECs

Tie2 clustering at cell-cell junction area and FOXO1 translocation from nucleus to cytosol by anti-Ang2 antibodies were examined in HUVECs by immunofluorescence. Specifically, HUVECs were seeded on 8 well slide chamber (Lab-TekII) and maintained in EGM-2 medium for 2~3 days. At 100% confluence, the cells were serum starved with EBM-2 medium for 4 hrs and then treated with 1 µg/ml anti-Ang2 antibodies together with 1 µg/ml of hAng2 for 30 min. Thereafter, the cells were fixed with 4% formaldehyde in PBS at room temperature (RT) for 10 min, permeabilized with 0.1% Triton X-100 in PBS, blocked with 1% BSA in PBS at RT for 60 min, and incubated with primary antibodies at RT for 1 hr. The primary antibodies for hTie2, FOXO1, and Human Fc were used. The cells were then incubated with secondary antibodies (Invitrogen) in the dark at RT for 1 hr and mounted with Vectashield mounting medium with DAPI (Vector Labs). Images were taken with a laser scanning confocal microscope (LSM880, Carl Zeiss).

Figure 5:
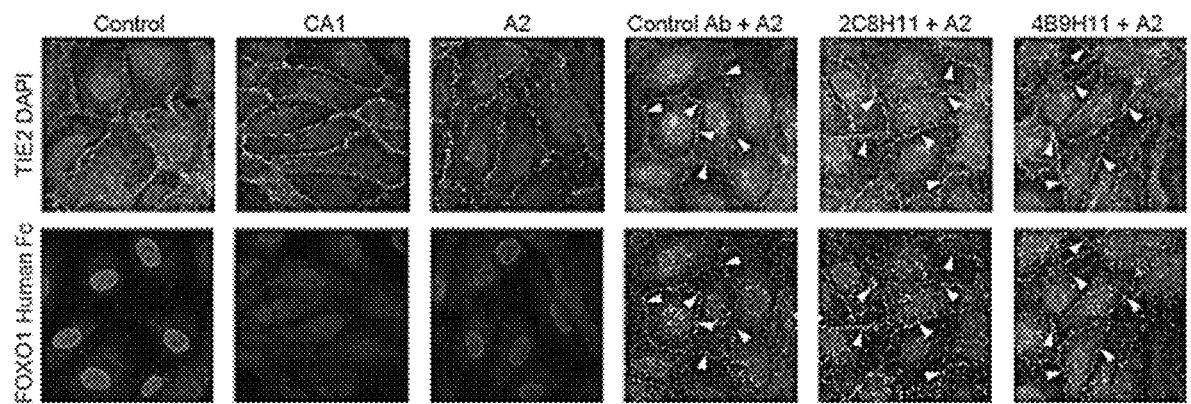
FIG. 5. Tie2 receptor clustering and FOXO1 translocation by humanized Ang2 antibodies. HUVECs were serum starved for 6 hrs and were incubated with COMP-Ang1 (CA1), Ang2 (A2), or Ang2 together with anti-Ang2 antibodies (Control Ab, 2C8H11 or 4B9H11) for 30 min. After fixation, HUVECs were stained with DAPI, anti-Tie2 antibody, anti-FOXO1 antibody and anti-human Fc to investigate Tie2 clustering at cell surface, FOXO1 translocation from nucleus, and the presence of humanized Ang2 antibodies in the cell-cell junction areas. Arrowheads indicate the clustered Tie2 and co-localized Ang2 antibodies at cell-cell contacts.

As shown in FIG. 5, the treatment of 2C8H11 or 4B9H11 with hAng2 induced Tie2 translocation/clustering to cell-cell contact just like Comp-Ang1 (CA1) or Control Ang2 antibody, which was known to induce Tie2 clustering and activation (Han et al., 2016, Science Translation Medicine). Consistent with a previous report showing FOXO1 localization in the cytoplasm after phosphorylation (Zhang et al, JBC 2002, 277, 45276-45284) while it was located in the nucleus under the basal, serum-starved condition, FOXO1 became markedly disappeared in nucleus with the treatment of 2C8H11+hAng2 or 4B9H11+hAng2, compared to serum-starved control (Red). Meanwhile, Ang2 treatment negligibly induced FOXO1 translocation form nucleus to cytosol. Interestingly, 2C8H11, 4B9H11 (Cyan) humanized antibodies were found to be co-localized with clustered Tie2 receptor at cell-cell contact and endocytosed Tie2 receptor in cytosol (FIG. 5), indicating that anti-Ang2 antibody form a tripartite complex with Tie2 receptor through binding to Ang2.

Figure 6:
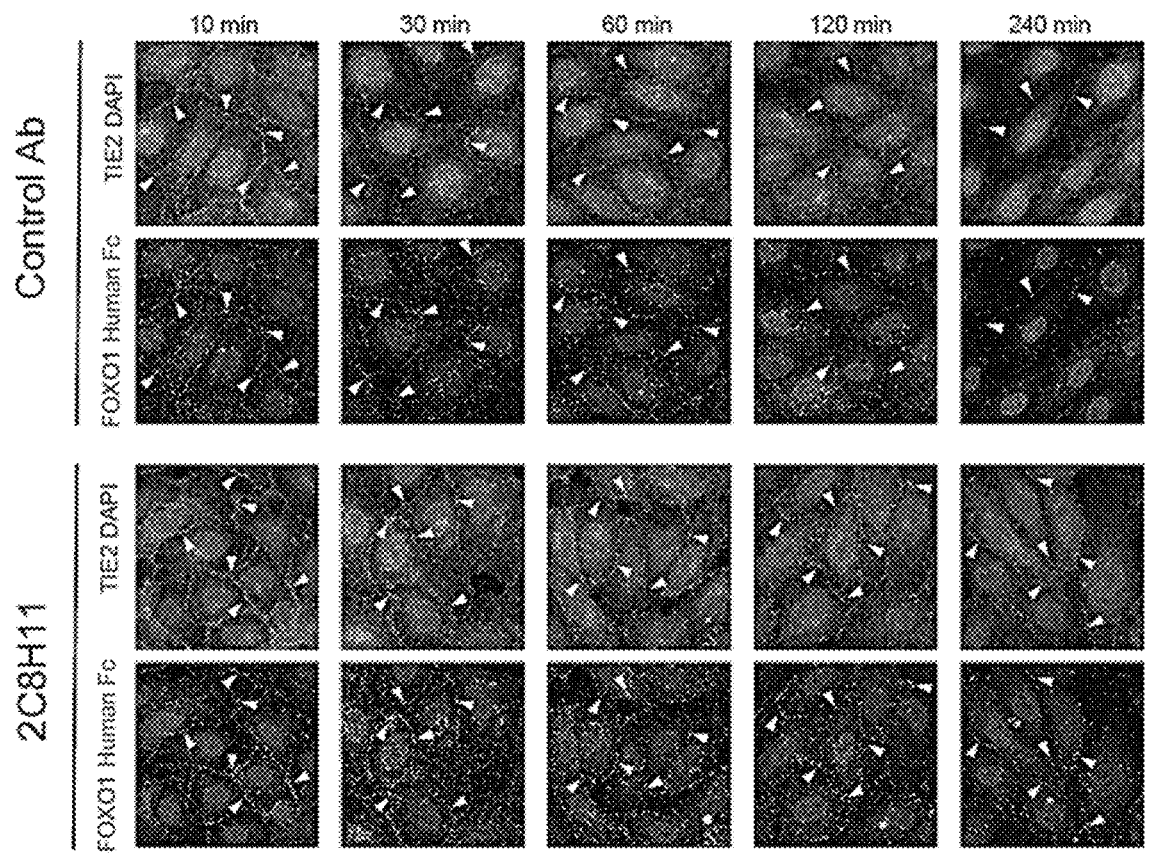
FIG. 6. Time-courses of Tie2 receptor clustering, FOXO1 translocation and localization of Ang2 antibodies in the cell-cell junctions in HUVECs. Serum-starved HUVECs were incubated with anti-Ang2 antibodies (control Ab or 2C8H11) for various time points, from 10 min to 240 min. After cell fixation, clustered Tie2 receptors at cell surface and endocytosed Tie2 receptors were investigated by staining with anti-Tie2 antibody. Humanized anti-Ang2 antibodies at cell surface and cytosol were probed with anti-human Fc antibody. Arrowheads indicate the clustered Tie2 and co-localized Ang2 antibodies at cell-cell contacts.

2C8H11-induced Tie2 clustering and FOXO1 translocation was examined in a time-course study (from 10 min to 240 min). As shown in FIG. 6, in the presence of hAng2, control Ang2 Ab induced Tie2 clustering at the cell-cell contact within 10 min, and triggered the endocytosis of clustered Tie2 receptors. After 30 min treatment of control Ang2 Ab+hAng2, Tie2 receptor at cell-cell contact was markedly diminished, and Tie2 receptor was mostly disappeared in 120 min and 240 min. When control Ang2 antibody was stained with anti-human Fc antibody, it showed a similar pattern just like that of Tie2 receptor. In contrast, in the case of 2C8H11 and hAng2, Tie2 clustering at cell-cell contact was sustained even after 240 min treatment. Consistently, co-localized 2C8H11 antibody with Tie2 at cell-cell contact was also maintained until 240 min (FIG. 6).

6-4: Inhibition of Vascular Permeability by Humanized Anti-Ang2 Antibodies

Figure 7:
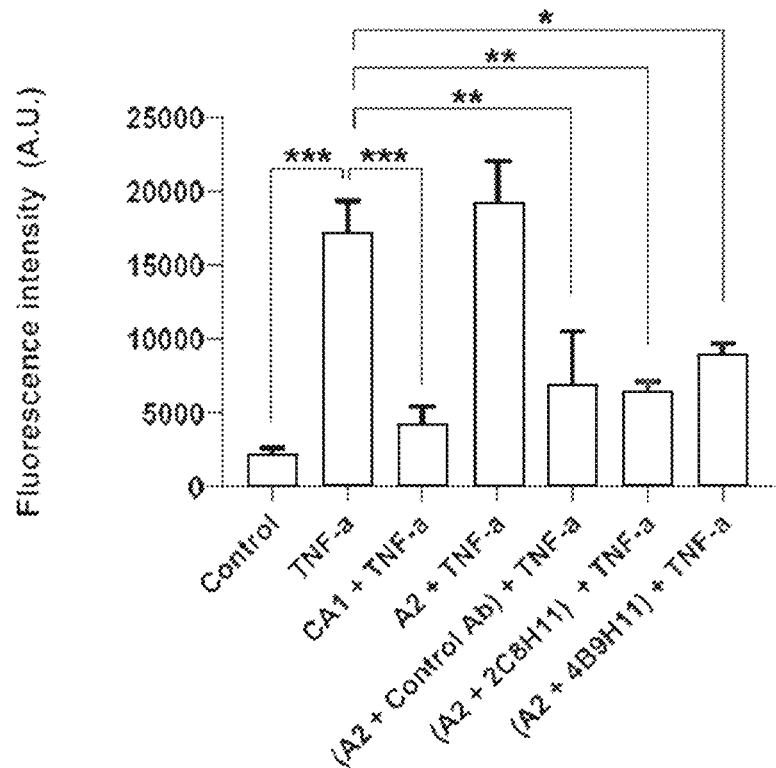
FIG. 7. Inhibition of vascular permeability by humanized anti-Ang2 antibodies. HUVECs were seeded on transwell chamber and grown for 3 days. At 100% confluency, HUVECs were pre-treated with COMP-Ang1 (CA1, 0.5 µg/ml), Ang2 (A2, 1 µg/ml), Ang2 together with Control Ab (A2+Control Ab, 1 µg/ml), 2C8H11 (A2+2C8H11, 1 µg/ml) or 4B9H11 (A2+4B9H11, 1 µg/ml) for 30 min and treated with TNF-α (100 ng/ml) for 22 hr into the upper chamber. Vascular permeability was assessed by measuring FITC fluorescence in the lower chamber after adding FITC-dextran for 20 min into the upper chamber. Values are mean±SD. *p<0.05, p<0.01, *p<0.001 by one-way ANOVA.

Vascular leakage assay was carried out in HUVECs using In Vitro Vascular Permeability Assay Kit (Millipore) according to the manufacturer's instruction. HUVECs were seeded into the insert of the transwell plate and cultured for 3 days for 100% confluence. The HUVECs were pre-incubated with Ang2 (1 µg/ml), Ang2 (1 µg/ml) together with Control, 2C8H11 or 4B9H11 antibody (1 µg/ml) for 30 min, and then TNF-α (100 ng/ml) was added, and the cells were incubated at 37° C. for 22 hr. FITC-dextran was added to the upper chamber and incubated for 20 min. Passage of FITC-dextran though the HUVEC monolayer was measured by a fluorescence reader at excitation and emission wavelengths of 485 and 535 nm, respectively. As shown in FIG. 7, pre-treatment of anti-Ang2 antibodies with Ang2 significantly inhibited the vascular leakage induced by vascular-leakage promoting factor TNF-a.

Example 7: Affinity Measurement of Humanized Anti-Ang2 Antibodies Against mAng2

Figure 8A:
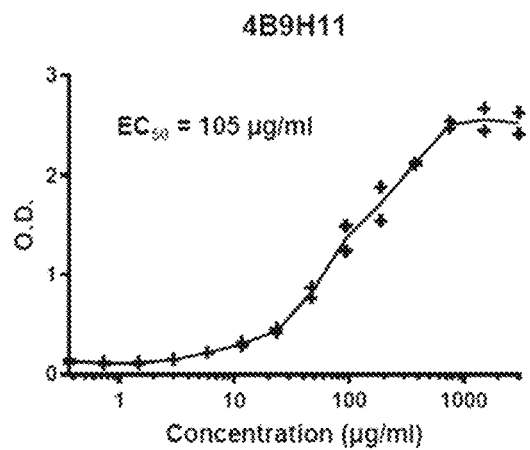
FIGS. 8A-8B. $EC_{50}$ values of anti-Ang2 antibodies against mouse Ang2 by ELISA. The binding affinities of humanized anti-Ang2 antibodies for mouse Ang2 (mAng2) were measured by analyzing $EC_{50}$ with ELISA. The recombinant mAng2 was coated and incubated with serially diluted anti-Ang2 antibodies, 4B9H11 and 2C8H11. Next, the plate was reacted with anti-human IgG (Fab)-HRP secondary antibody. The plate was treated with TMB solution and absorbance was measured at 450 nm for anti-Ang2 antibodies, 4B9H11 (FIG. 8A) and 2C8H11 (FIG. 8B). $EC_{50}$ value was analyzed using PerkinElmer's WorkOut 2.5 program.
Figure 8B:
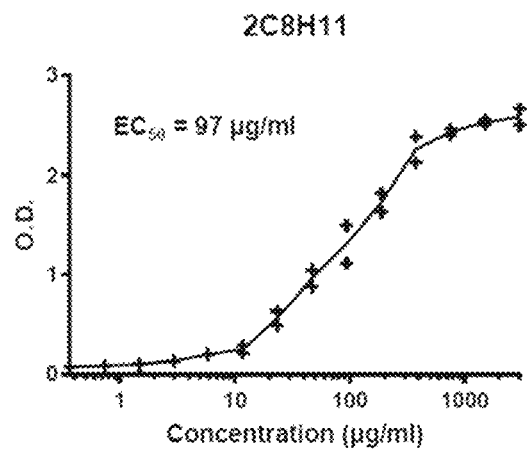

The affinity of humanized antibodies for mouse Ang2 (mAng2) was analyzed by ELISA. Specifically, mAng2 was diluted in 30 µl of a coating buffer (0.1 M sodium carbonate buffer) at 20 ng per well in a half 96-well plate (Corning 3690) and incubated overnight at 4° C. After washing with TBS-T solution for 3 times, the well plate was blocked with 3% skim milk at room temperature for 1 hr and then washed again. 2C8H11 and 4B9H11 were serially diluted from 3 mg/ml to 300 ng/ml. After loading 30 µl of the diluted ant-Ang2 antibodies into wells, the well plate was incubated at room temperature for 2 hrs. Next, 30 µl of a 1:3000 dilution of anti-human IgG (Fab)-HRP (Jackson) secondary antibody was added to each well and incubated at room temperature for 1 hr. After completion of all reactions, the plate was washed again with TB S-T and then treated with 30 µl of TMB solution per well. After developing for 5 min, the plate was treated with IN sulfuric acid to stop the reaction, and absorbance was measured at 450 nm. Based on the measured OD value, the $EC_{50}$ value was analyzed using PerkinElmer's WorkOut 2.5 program. $EC_{50}$ of 4B9H11 and 2C8H11 for mAng2 binding were 105 µg/ml and 97 µg/ml, respectively, (FIGS. 8A-8B).

Example 8: Evaluation of the Tumor Growth Inhibition Effect in LLC Subcutaneous Model 2C8H11 anti-Ang2 antibody was tested for its ability to inhibit tumor growth in LLC (Lewis Lung Carcinoma) cell line tumor model. Specifically, LLC cell line (ATCC) was cultured in DMEM (Gibco) supplemented with 10% FBS (Gibco). LLC cells ($1\times10^6$ in 100 µl of PBS) were subcutaneously injected into 6~8-week-old C57BL/6 mice (Jackson Laboratory) which were anesthetized with a mixture of Ketamine and Xylazine. When the volume of the tumors reached 50~100 mm$^3$, the mice were intraperitoneally administered with 10 mg/kg of 2C8H11 antibody every 2~3 days. Cisplatin (Cpt) was injected intraperitoneally once at a dose of 3 mg/kg in both monotherapy and combination therapy groups. The changes in tumor volume was tracked over the following days. Tumor volume (V) was measured using the formula:

$$V=(\text{width}^2\times\text{length})/2$$

Figure 9:
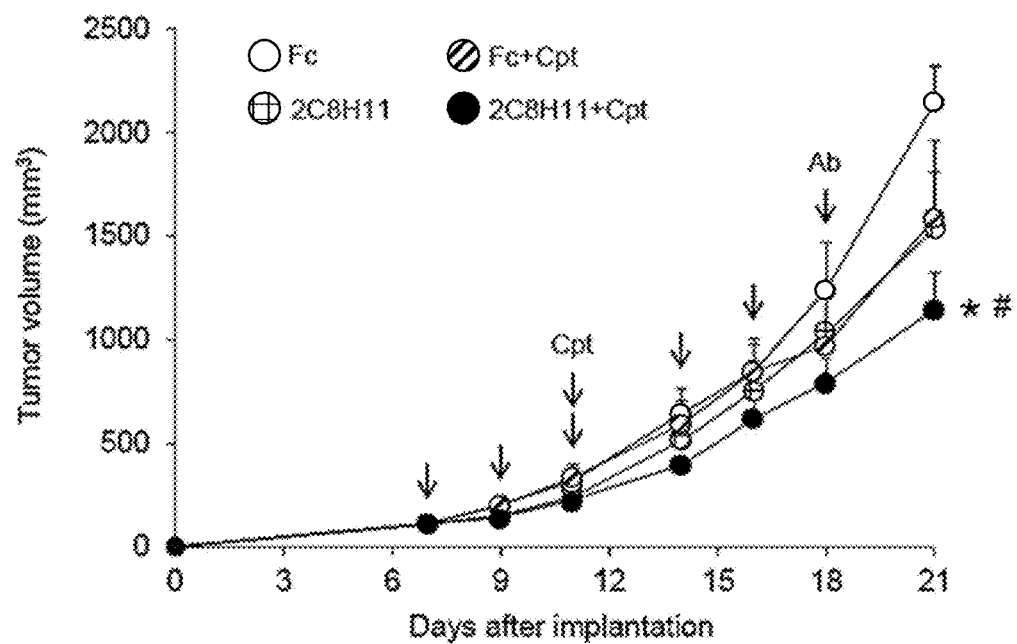
FIG. 9. Inhibition of tumor growth by humanized 2C8H11 antibodies and Cisplatin (Cpt) in LLC tumor model. LLC tumor growths were compared in mice treated as indicated, starting 7 days after tumor implantation. Black arrows indicate injections of antibodies, while red arrow indicate single injection of Cpt. n=7~9 for each group. Values are mean±SD. *p<0.05 versus Fc; #p<0.05 versus Fc+Cpt.

The experiment was performed in 4 groups: Fc (control group), Fc+Cpt group, 2C8H11 group, and 2C8H11+Cpt group. As shown in FIG. 9, 2C8H11 antibody inhibited tumor growth by 29% compared with Fc, which was similar to the tumor growth inhibition effect by Fc+Cpt injection. Meanwhile, combined treatment with 2C8H11 and Cpt delayed tumor growth by 47% compared with Fc. Thus, these results demonstrate that combined treatment with 2C8H11 with Cpt inhibited tumor growth most potently.

Example 9: The Tumor Vessel Normalization Effect of 2C8H11 Antibody

In order to investigate the changes in tumor vessels by 2C811 antibody, we obtained frozen sections of tumor samples and performed immunofluorescence analyses by staining with a blood vessel-specific marker, CD31, and pericyte-specific marker, PDGFRβ. In detail, the tumor samples were harvested from the mice from the experiment described in Example 8, which were fixed in 4% paraformaldehyde (PFA, Merck), dehydrated in 30% sucrose (Junsei), embedded in OCT compound (Leica), and sectioned using a cryostat (Leica). The resulting frozen sections were blocked for 1 hr using a Protein Blocking Buffer (DAKO). Then the sections were stained with hamster anti-CD31 antibody (1:200, Millipore) and rat anti-PDGFRβ antibody (1:200, eBioscience) in PBS at 4° C. for 8 hrs. After washing 3 times with PBS, the sections were stained with Alexa488-conjugated anti-hamster IgG antibody and Alexa594-conjugated anti-rat IgG antibody (1:1000, Jackson Immunoresearch) in PBS for 1 hr at room temperature. After another 3 washes with PBS, the sections were mounted in fluorescence mounting medium (DAKO) using a coverslip (Marienfeld). The stained sections were imaged using LSM880 confocal microscope (Zeiss).

Figure 10A:
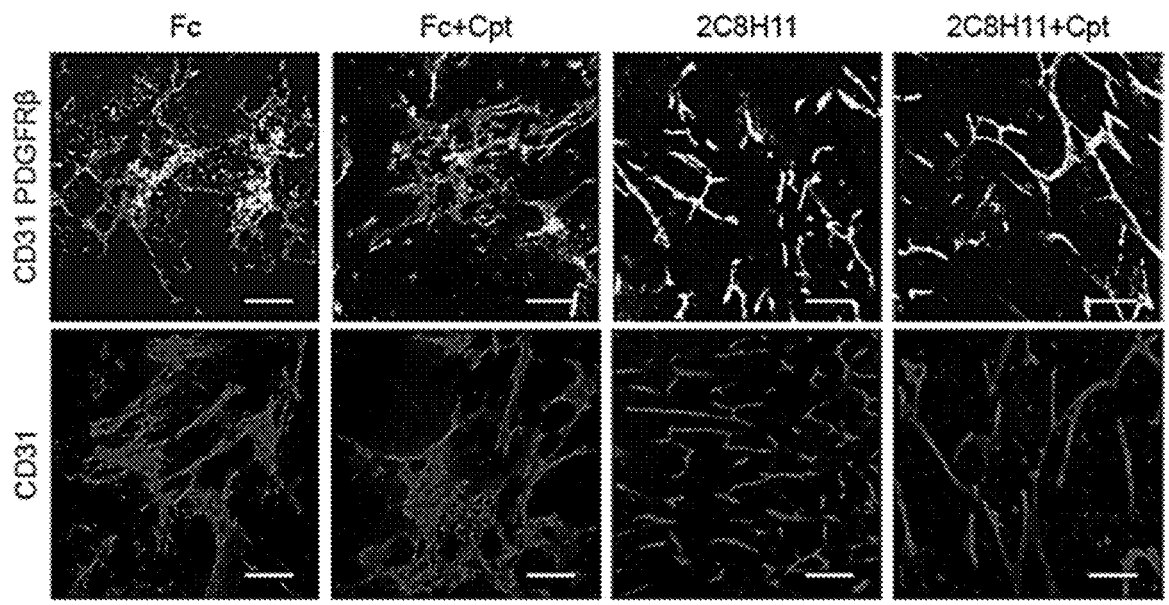

The results are shown in FIGS. 10A-10C. Compared with tumors treated with Fc or Fc+Cpt, tumor blood vessel (BV) density was reduced by 56% in either 2C8H11 or 2C8H11+Cpt treated tumors and the morphology of these vasculature was normalized so that it was similar to a normal blood vessel (FIG. 10B). Furthermore, the tumors treated with 2C8H11 or 2C8H11+Cpt had increased PDGFRβ$^+$ pericyte coverage (2.4-fold increase) (FIG. 10C), and the blood vessel and perivascular cells were more closely associated with each other. These results show that 2C8H11 antibody can reduce the blood vessel density within a tumor mass and normalize their morphology.

Example 10: Increased Functionality of Tumor Vessels by 2C8H11 Antibody

To analyze the functionality of tumor vessels after treatment with 2C8H11, vessel perfusability and hypoxia status were evaluated. Before harvesting tumor mass, the mice were intravenously injected with 100 μl of DyLight488-Lectin (Vector laboratory) and intraperitoneally injected with 60 mg/kg of Pimonidazole-HCl (Hypoxyprobe) dissolved in PBS for 30 min before sacrifice. The mice were perfusion-fixed with 4% PFA. We obtained frozen sections from the tumor mass, which were stained with hamster anti-CD31 antibody (1:200, Millipore) and 4.3.11.3 mouse Pacific blue-Mab (1:50, Hypoxyprobe) in PBS. The sections were imaged using LSM880 confocal microscope (Zeiss), and the obtained images were analyzed using ImageJ software (http://rsb.info.nih.gov/ij) to quantify Lectin$^+$ area/CD31$^+$ area and Hypoxyprobe$^+$ area.

Figure 11B:
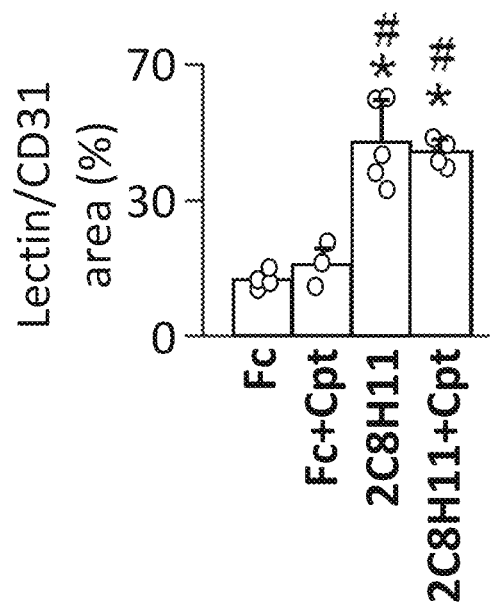
Figure 11C:
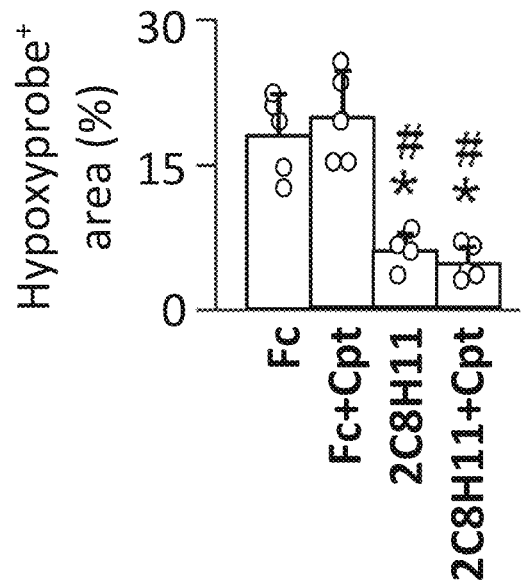

The results are shown in FIGS. 11A-11C. The tumors treated with 2C8H11 or 2C8H11+Cpt displayed normalized tumor vessels that had enhanced perfusion as judged by increased Lectin$^+$ area/CD31$^+$ area (approximately 3-fold increase in perfusion), compared with those treated with Fc or Fc+Cpt (FIG. 11B). Furthermore, hypoxia, as indicated by Hypoxyprobe$^+$ area, was decreased in tumors treated with 2C8H11 or 2C8H11+Cpt by 72%, when compared with tumors treated with Fc or Fc+Cpt (FIG. 11C). These results indicate that 2C8H11 antibody not only normalized the morphology of tumor vessels but also enhances their functionality by increasing vessel perfusability, which subsequently lead to decreased hypoxia.

Figure 12A:
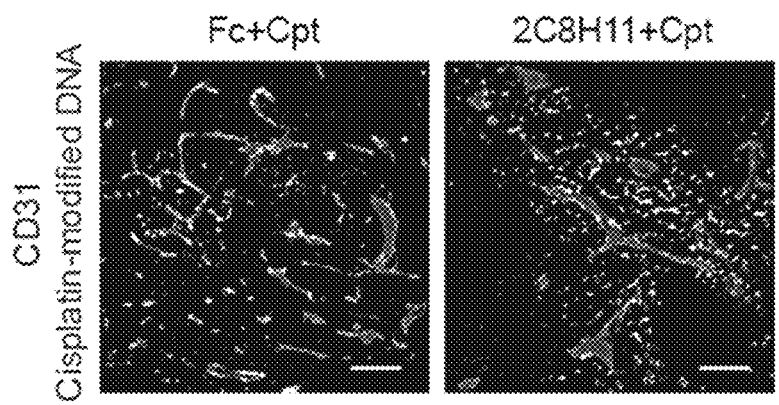
FIGS. 12A-12B. Enhanced Cpt drug delivery into the tumor core by humanized 2C8H11 antibody. Cpt$^+$ area was imaged in tumor harvested on day 21, using anti Cpt-modified DNA antibody (FIG. 12A). Cpt$^+$ area was measured as a percentage per total sectional area (FIG. 12B). Scale bar, 100 n=5 for each group. Values are mean±SD. #p<0.05 versus Fc+Cpt.
Figure 12B:
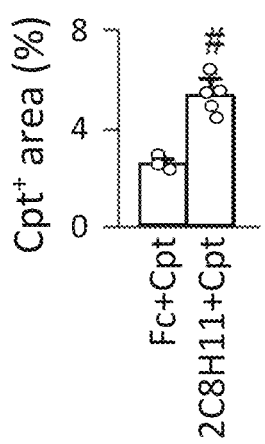

Example 11: Increased Anti-Cancer Drug Delivery into the Tumor Mass by 2C8H11 Antibody The drug, Cpt, inhibits tumor growth by inhibiting DNA synthesis, and has been widely used in human cancer patients. To evaluate whether the 2C8 antibody can increase the delivery of this drug into tumors by normalizing tumor vessels, the frozen sections of tumors were stained with anti-Cisplatin-modified DNA antibody (1:100, Abcam) and hamster anti-CD31 antibody (1:200, Millipore). As shown in FIGS. 12A and 12B, the levels of Cpt-modified DNA was significantly increased by 2.1 folds in the 2C8H11/Cpt-treated group, compared with Fc+Cpt treated group. This result shows that the delivery of Cpt to the tumor mass was enhanced due to the normalized tumor vessels by 2C8H11 antibody, which subsequently potently inhibits tumor growth.

Example 12: CNV Regression and Vascular Leakage Suppression Effect of 2C8H11 Antibody in Laser-Induced CNV Model 2C8H11 antibody was tested for its ability to inhibit choroidal neovascularization (CNV), the hallmark of wet age-related macular degeneration (AMD) using laser-induced CNV model. After dilation of pupils with 5 mg/ml phenylephrine and 5 mg/ml tropicamide eye drops (Santen Pharmaceutical) and instillation of 0.5% proparacaine hydrochloride eye drops (Alcon) for topical anesthesia, laser photocoagulator (Lumenis Inc.) with a slit lamp delivery system was used with a glass coverslip as a contact lens to visualize the retina. Sufficient laser energy (532 nm wavelength, 250 mW power, 100 ms duration, 50 μm spot size) was delivered in 4 locations for each eye (the 3, 6, 9 and 12 o'clock positions of the posterior pole). Only burns that produced a bubble at the time of laser photocoagulation, indicating the rupture of the Bruch's membrane, were included in this study. Spots containing hemorrhage at the laser site were excluded from the analysis. To recapitulate a clinical situation, 2C8H11 (5 μg) was administered intravitreally to the mice at 7 days after laser photocoagulation (FIG. 13A). As a control or as for comparison, Fc or VEGF-Trap (5 μg each) was administered in the same manner to the mice. To intravitreally administer indicated reagents, ~1 μl (5 mg/ml) containing 5 μg of each reagent was injected into the vitreal cavity using the Nanoliter 2000 micro-injector (World Precision Instruments) fitted with a glass capillary pipette. CD31$^+$ CNV volumes of the retinal pigment epithelium (RPE)-choroid-sclera flat mounts were calculated using the MATLAB image processing toolbox (MathWorks) at 14 days after laser photocoagulation. Anti-CD31 antibody (1:200, Millipore) was used for the detection of endothelial cells of CNV. VEGF-Trap effectively induced CNV regression by 64.4% compared with Fc, and 2C8H11 similarly induced CNV regression (65.3%) (FIG. 13B, C). Combined fluorescein angiography (FA) and indocyanine green angiography (ICGA) enabled us to measure vascular leakage at the neovessels around the laser injury site. Continuous-wave laser modules at 488 nm and 785 nm were used as excitation sources for fluorescein and ICG, respectively. A raster scanning pattern of excitation lasers was achieved by a scanner system consisting of a rotating polygonal mirror (MC-5; Lincoln Laser) and a galvanometer-based scanning mirror (6230H; Cambridge technology), and delivered to the back aperture of an imaging lens. A high numerical aperture (NA) objective lens (PlanApo λ, NA 0.75; Nikon) was used as the imaging lens to provide wide-field fundus fluorescence images. Fluorescence signals detected by photomultiplier tubes (R9110, Hamamatsu Photonics) were digitized by frame grabber and reconstructed to images with size of 512×512 pixels per frame in real time. To visualize late-phase (6 min) FA and ICGA images utilizing the angiography system, 10 mg of fluorescein sodium (Alcon) and 0.15 mg of ICG (Daiichi Pharmaceutical) were administered intraperitoneally and intravenously, respectively. The imaging procedure was performed under systemic anesthesia and pupil dilation to improve the quality of images. Leaky areas from CNV were calculated as the total measured hyperfluorescent areas in FA images divided by the total measured CNV areas in ICGA images using a Java-based imaging software (ImajeJ, National Institutes of Health). Compared with Fc, both VEGF-Trap (37.0%) and 2C8H11 (38.3%) similarly suppressed vascular leakage (FIG. 13B, D). Of note, the Fc-treated group showed no significant difference in vascular leakage between 6 and 14 days after laser photocoagulation, but VEGF-Trap and 2C8H11 markedly reduced vascular leakage (45.6% and 50.0%, respectively) (FIG. 13B, D). Thus, the magnitude of the suppression of CNV and vascular leakage was quantitatively indistinguishable between VEGF-Trap and 2C8H11 in the mouse model of laser-induced CNV.

Figure 14B:
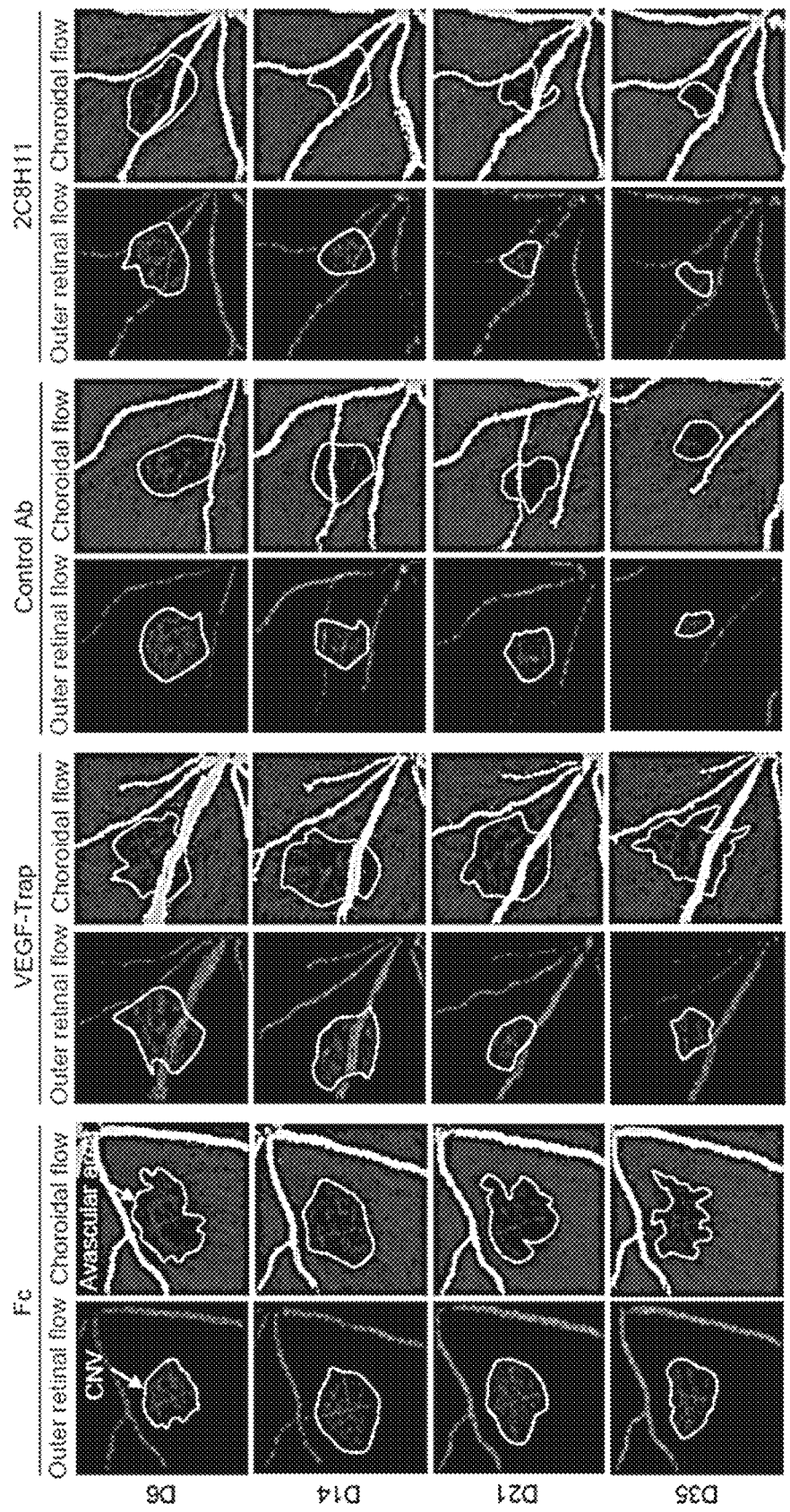
Figure 14C:
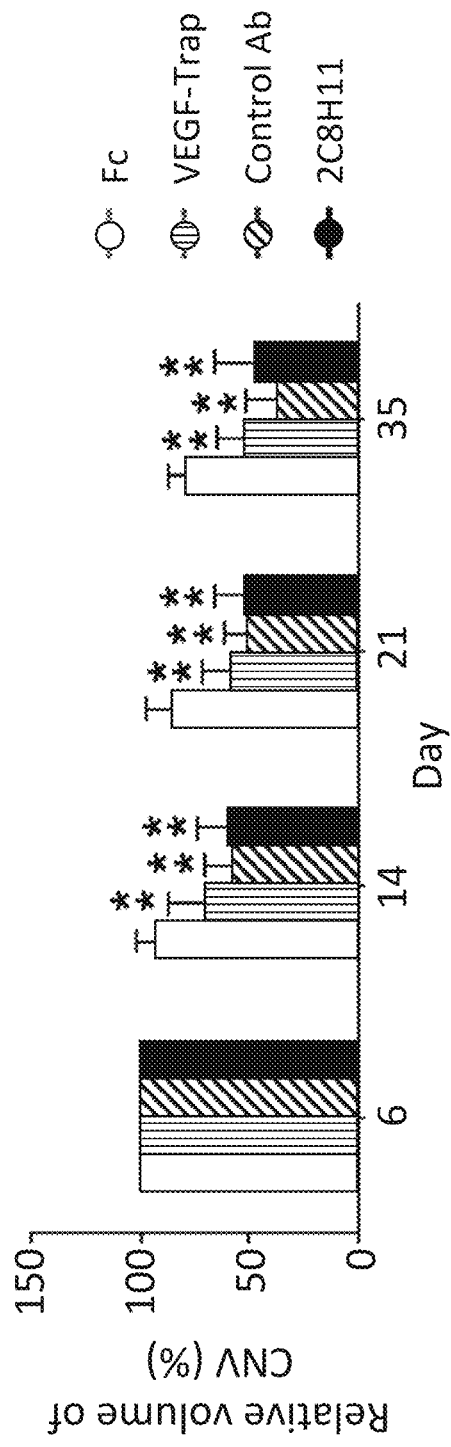
Figure 14D:
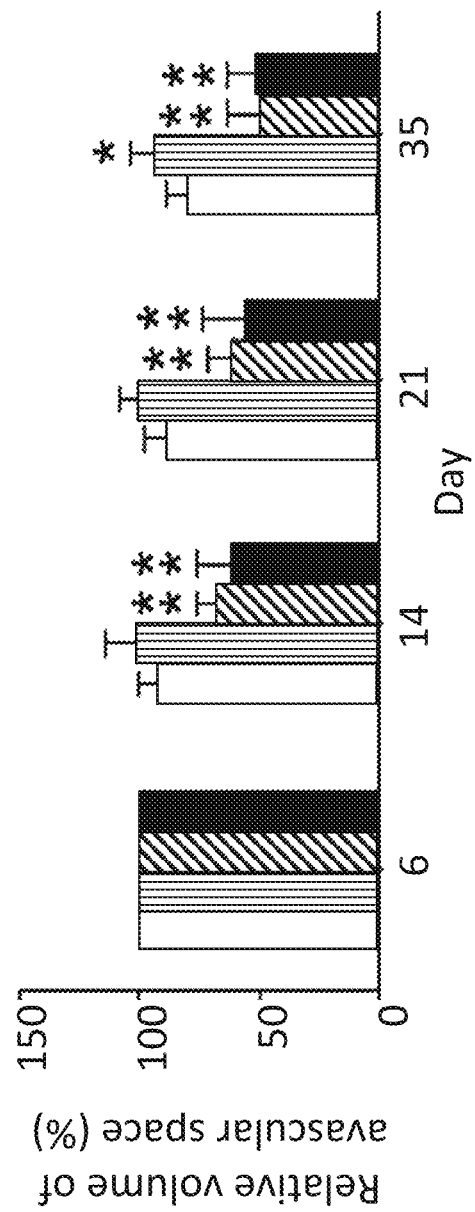

Example 13: CNV Regression and Choriocapillary Regeneration Effect of 2C8H11 Antibody To determine the effect of 2C8H11 in CNV regression and choriocapillary regeneration after establishment of CNV, Fc, VEGF-Trap, control antibody or 2C8H11 (5 µg each) was given intravitreally to the mice by the Nanoliter 2000 micro-injector (World Precision Instruments) at 7 days after laser photocoagulation. Intra-vital optical coherence tomography angiography (OCTA) was performed at 6, 14, 21, and 35 days after laser photocoagulation (FIG. 14A). The retinochoroidal layers were imaged using a prototype high-speed swept-source optical coherence tomography (OCT) system, utilizing a custom ring cavity wavelength-swept laser centered at 1048 nm with an A-scan rate of 230 kHz. OCT images were collected in a 1.7 mm×1.7 mm field of view within the retino-choroidal layer to monitor regeneration of choroidal vasculatures at the site of laser photocoagulation after intravitreal injection of reagents. To obtain cross-sectional OCT angiograms, which allows for selective visualization of blood vessels without the retinal and choroidal parenchyma, we compared repeatedly recorded B-scan images and detected pixel-by-pixel intensity decorrelation of those images mainly caused by movement of erythrocytes inside the vessels. Then, by using automatic layer flattening and segmentation algorithms, cross-sectional OCT angiograms were flattened to RPE, and en face OCT angiograms were generated by separate projection of each flattened cross-sectional OCT angiogram in three depth ranges: inner retinal, outer retinal and choroidal layers. The outer plexiform layer and Bruch's membrane were defined as the boundaries separating inner retinal, outer retinal, and choroidal layers. The density of retina and choroid vessel was automatically calculated as the proportion of measured area occupied by flowing blood vessels defined as pixels having decorrelation values above the threshold level. Avascular pixels were detected from the en face OCT angiogram representing choroidal layer by means of the image processing toolbox of MATLAB (Math Works). Then the total volume of the avascular space surrounding the laser injury site was calculated by summing the number of avascular pixels multiplied by the volume of one pixel. In order to analyze the changing complexion of avascular space volume, serially measured values in each eye were transformed into percentage change from baseline value. There was a slight reduction of the CNV volume in outer retinas treated with Fc, but those treated with VEGF-Trap and 2C8H11 showed markedly reduced CNV volume (FIG. 14B, C). Meanwhile, a slight reduction of the avascular space was observed in choroids treated with Fc. Intriguingly, choroids in 2C8H11-treated eyes showed serial and profound reduction of the avascular space by 30.1%, 36.4%, and 37.0% at 14, 21, and 35 days after laser photocoagulation, respectively (FIG. 14B, D). Similarly, choroids in control Ab-treated eyes showed reduction of the avascular space by 21.7%, 30.2%, and 38.0% at 14, 21, and 35 days after laser photocoagulation, respectively (FIG. 14B, D). However, choroids in VEGF-Trap-treated eyes showed increased avascular space by 11.4%, 16.0%, and 18.1% at D14, D21, and D35, respectively (FIG. 14B, D). Overall, these findings indicate that both 2C8H11 and control Ab promotes regeneration of the choriocapillaris, while VEGF-Trap leads to choriocapillary regression in the laser-induced CNV model.

Figure 15A:
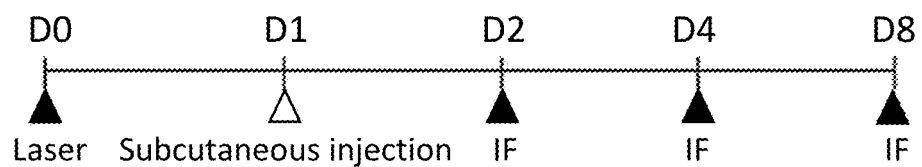
FIGS. 15A-15D. Co-localization of 2C8H11 antibody and CD31 in endothelial cells of CNV. The subcutaneous administration of 2C8H11 antibody was performed at 1 day after laser photocoagulation (FIG. 15A). The co-localization of 2C8H11 antibody and CD31 in endothelial cells of CNV was directly detected by anti-human IgG antibody at 2, 4, and 8 days after laser photocoagulation (FIGS. 15A-15D).
Figure 15B:
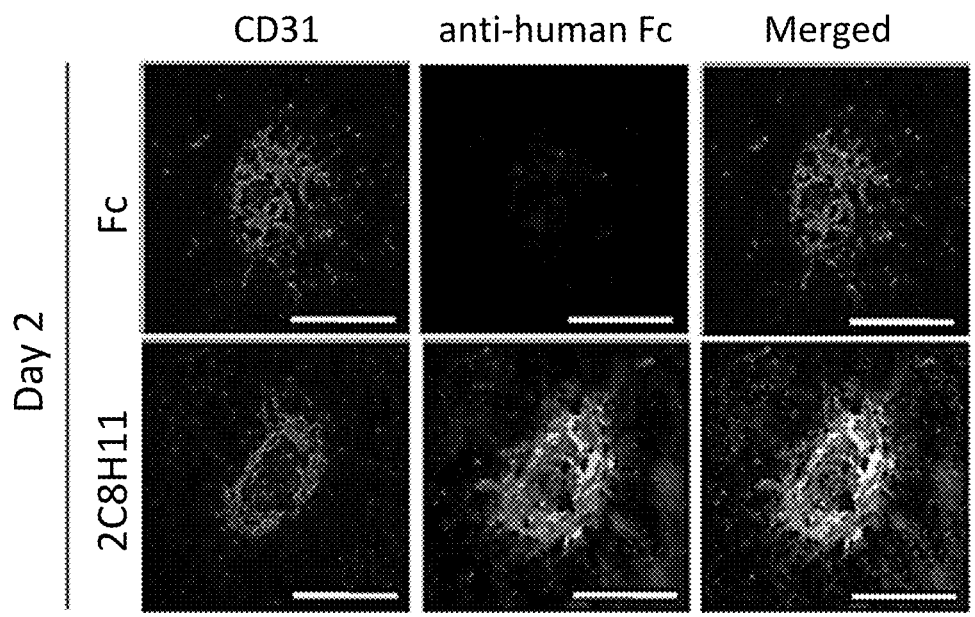
Figure 15C:
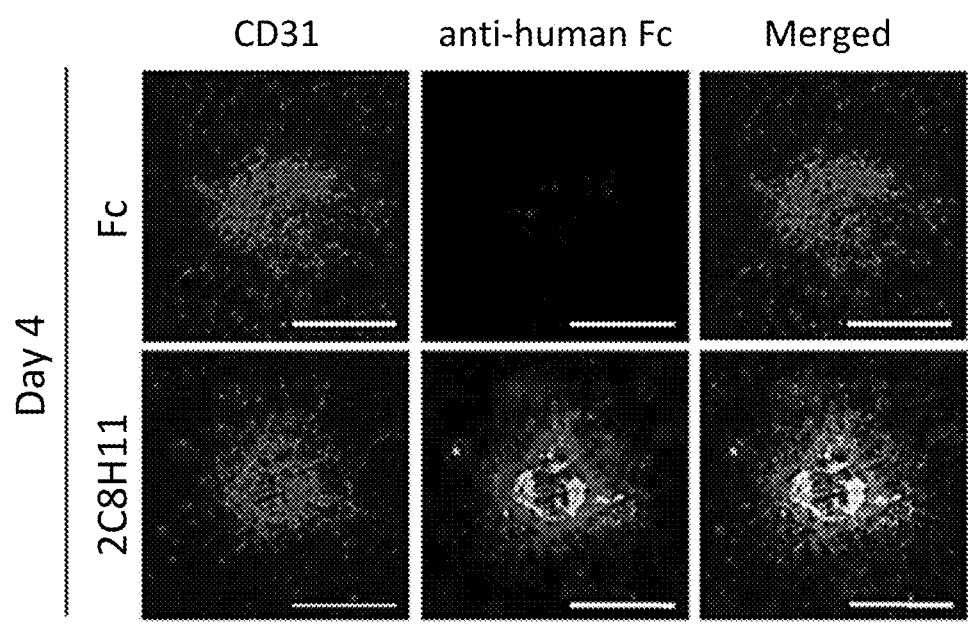
Figure 15D:
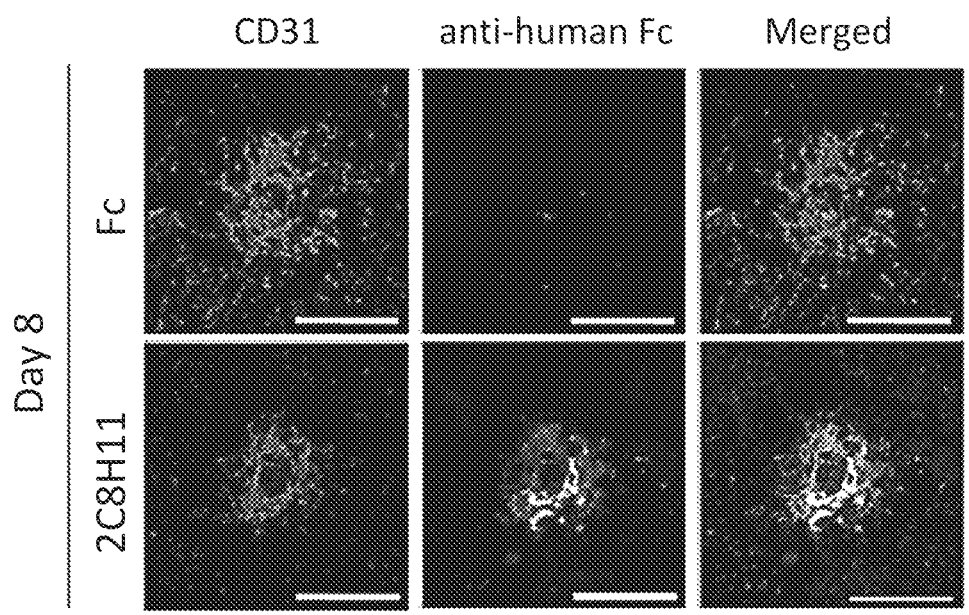

Example 14: Co-Localization of 2C8H11 Antibody and CD31 in Endothelial Cells of CNV To investigate whether subcutaneously injected 2C8H11 can also exert the therapeutic effects on CNV, we firstly evaluated co-localization 2C8H11 antibody and CD31 in endothelial cells of CNV. The subcutaneous administration of 2C8H11 antibody (25 mg/kg) was performed at 1 day after laser photocoagulation. As a control, Fc (25 mg/kg) was administered in the same manner to the mice. The co-localization of 2C8H11 antibody and anti-CD31 antibody (1:200, Millipore) in endothelial cells of CNV was directly detected by anti-human IgG antibody (1:1000, Jackson ImmunoResearch Laboratories) at 2, 4, and 8 days after laser photocoagulation (FIG. 15A). The administered 2C8H11 was highly detectable in the CD31$^+$ endothelial cells in CNV area (FIG. 15B-D).

Example 15: CNV Inhibition Effect of Subcutaneously Injected 2C8H11 Antibody

Figure 16A:
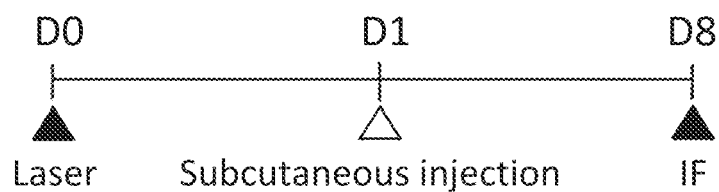
FIGS. 16A-16C. CNV inhibition effect of subcutaneously injected 2C8H11 antibody. The subcutaneous administration of 2C8H11 antibody was performed at 1 day after laser photocoagulation (FIG. 16A). CD31$^+$ CNV volumes were measured at 8 days after laser photocoagulation (FIGS. 16A-16C). Scale bar, 100 μm. n=10 for each group. Values are mean±SD. ***p<0.001 by unpaired Student's t-test.
Figure 16B:
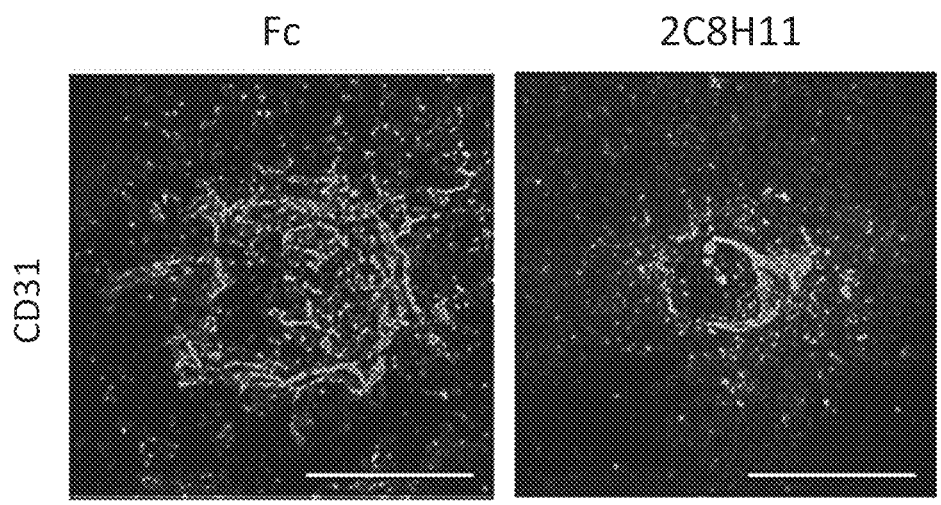
Figure 16C:
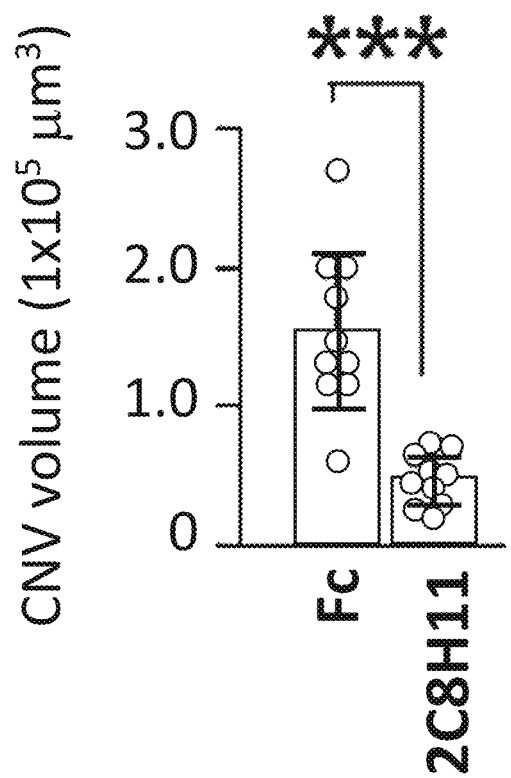

To determine the effect of subcutaneously injected 2C8H11 antibody in CNV inhibition, the subcutaneous administration of 2C8H11 antibody (25 mg/kg) was performed at 1 day after laser photocoagulation. As a control, Fc (25 mg/kg) was administered in a same manner to the mice. Anti-CD31 antibody (1:200, Millipore) was used for the detection of endothelial cells of CNV, and CD31$^+$ CNV volumes of the RPE-choroid-sclera flat mounts were calculated using the MATLAB image processing toolbox (MathWorks) at 8 days after laser photocoagulation (FIG. 16A). 2C8H11 effectively inhibited CNV formation by 69.9% compared with Fc (FIG. 16B, C), indicating that not only intravitreal injection but also subcutaneous injection of 2C8H11 have the inhibitory effect on CNV.

The microorganism of the present invention was named as 2C8 and deposited at the Korean Cell Line Bank (KCLB) at Cancer Research Institute, Seoul National University, College of Medicine, 28 Yongon-dong, Chongno-Gu, Seoul, 110-744, Korea on Jan. 30, 2018 (Accession No: KCLRF-BP-00417).

The microorganism of the present invention was named as 4B9 and deposited at the Korean Cell Line Bank (KCLB) at Cancer Research Institute, Seoul National University, College of Medicine, 28 Yongon-dong, Chongno-Gu, Seoul, 110-744, Korea on Jan. 30, 2018 (Accession No: KCLRF-BP-00418).

INDUSTRIAL APPLICABILITY

The present invention relates to an antibody that inhibits Ang2 and simultaneously activates Tie2 receptor resulting in promotes downstream signal transduction. It provides a method of inhibiting Ang2-induced angiogenesis and reducing vascular permeability. In addition, the antibody according to the present invention can be useful for diagnosis and treatment of abnormal angiogenesis-related diseases such as eye diseases or cancer and/or diseases caused by increased vascular permeability.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention will be defined by the accompanying claims and their equivalents.

The invention claimed is:

1. An antibody or antigen-binding fragment thereof that specifically binds human Angiopoietin-2 and induces Tie2 activation, wherein the antibody or antigen-binding fragment thereof comprises:
    (a) the complementarity determining regions (CDRs) of a heavy chain variable region comprising the HCDR1 amino acid sequence of SEQ ID NO: 13, the HCDR2 amino acid sequence of SEQ ID NO: 14, and the HCDR3 amino acid sequence of SEQ ID NO: 15; and
    (b) the CDRs of a light chain variable region comprising the LCDR1 amino acid sequence of SEQ ID NO: 16, the LCDR2 amino acid sequence of SEQ ID NO: 17, and the LCDR3 amino acid sequence of SEQ ID NO: 18, binds to amino acids of SEQ ID NO: 115, amino acids of SEQ ID NO: 116, or amino acids of SEQ ID NO: 117.

2. The antibody or antigen-binding fragment thereof of claim 1, wherein the antibody or antigen-binding fragment thereof binds to amino acids of SEQ ID NO: 115.

3. The antibody or antigen-binding fragment thereof of claim 1, wherein the antibody or antigen-binding fragment thereof binds to human and mouse Ang2.

4. The antibody or antigen-binding fragment thereof of claim 1, wherein the antibody is polyclonal or monoclonal.

5. The antibody or antigen-binding fragment thereof of claim 1, wherein the antigen-binding fragment is scFv or Fab.

6. The antibody or antigen-binding fragment thereof of claim 1, wherein the antibody is humanized.

7. The antibody or antigen-binding fragment thereof of claim 1, comprising:
    a heavy chain variable region selected from the group consisting of SEQ ID NOs: 19, 55, 59, 63, 67, 71, 75, 79, 83, 87, 91, 95, 99, 103, 107 or 111; and
    a light chain variable region selected from the group consisting of SEQ ID NOs: 21, 56, 60, 64, 68, 72, 76, 80, 84, 88, 92, 96, 100, 104, 108 or 112.

8. A pharmaceutical composition comprising the antibody or antigen-binding fragment thereof of claim 1 and a pharmaceutically acceptable carrier.

9. The pharmaceutical composition of claim 8, further comprising a small molecule inhibitor, wherein the small molecule inhibitor is a chemotherapy agent.

10. The pharmaceutical composition of claim 8, further comprising a vascular endothelial growth factor (VEGF) antagonist.

11. The pharmaceutical composition of claim 10, wherein the VEGF antagonist is an anti-VEGF antibody, a VEGF inhibiting fusion protein, or a small molecule kinase inhibitor.

12. A monoclonal antibody or antigen-binding fragment thereof that specifically binds human Angiopoietin-2 and induces Tie2 activation, wherein the antibody or antigen-binding fragment thereof comprises the complementary determining regions (CDRs) of an antibody produced from a cell line deposited with accession number KCLRF-BP-00417.

* * * * *

UNITED STATES PATENT AND TRADEMARK OFFICE
CERTIFICATE OF CORRECTION

PATENT NO. : 11,498,962 B2
APPLICATION NO. : 16/995707
DATED : November 15, 2022
INVENTOR(S) : Gou Young Koh et al.

Page 1 of 1

It is certified that error appears in the above-identified patent and that said Letters Patent is hereby corrected as shown below:

In the Claims

In Claim 1, Column 115, Lines 39-41, delete ", binds to amino acids of SEQ ID NO: 115, amino acids of SEQ ID NO: 116, or amino acids of SEQ ID NO: 117"

Signed and Sealed this
Seventh Day of February, 2023

Katherine Kelly Vidal
*Director of the United States Patent and Trademark Office*